United States Patent
Cook

(10) Patent No.: US 10,160,971 B2
(45) Date of Patent: Dec. 25, 2018

(54) METHODS OF MODULATING WARS2

(71) Applicants: NATIONAL UNIVERSITY OF SINGAPORE, Singapore (SG); SINGAPORE HEALTH SERVICES PTE LTD, Singapore (SG)

(72) Inventor: Stuart A. Cook, Singapore (SG)

(73) Assignees: National University of Singapore, Singapore (SG); Singapore Health Services PTE Ltd, Singapore (SG)

( * ) Notice: Subject to any disclaimer, the term of this patent is extended or adjusted under 35 U.S.C. 154(b) by 0 days.

(21) Appl. No.: 15/124,916

(22) PCT Filed: Mar. 13, 2015

(86) PCT No.: PCT/SG2015/000078
§ 371 (c)(1),
(2) Date: Sep. 9, 2016

(87) PCT Pub. No.: WO2015/137881
PCT Pub. Date: Sep. 17, 2015

(65) Prior Publication Data
US 2017/0022503 A1    Jan. 26, 2017

Related U.S. Application Data

(60) Provisional application No. 61/952,510, filed on Mar. 13, 2014.

(51) Int. Cl.
| | |
|---|---|
| *A61K 48/00* | (2006.01) |
| *C07H 21/02* | (2006.01) |
| *C07H 21/04* | (2006.01) |
| *C12N 15/113* | (2010.01) |
| *A61K 38/53* | (2006.01) |
| *G01N 33/50* | (2006.01) |
| *G01N 33/574* | (2006.01) |
| *A61K 31/422* | (2006.01) |
| *C12Q 1/6886* | (2018.01) |
| *G01N 33/573* | (2006.01) |

(52) U.S. Cl.
CPC ........ *C12N 15/1137* (2013.01); *A61K 31/422* (2013.01); *A61K 38/53* (2013.01); *C12Q 1/6886* (2013.01); *C12Y 601/01002* (2013.01); *G01N 33/5079* (2013.01); *G01N 33/573* (2013.01); *G01N 33/57484* (2013.01); *C12N 2310/14* (2013.01); *C12N 2310/3233* (2013.01); *C12N 2320/30* (2013.01); *C12Q 2600/136* (2013.01); *C12Q 2600/156* (2013.01); *C12Q 2600/158* (2013.01); *G01N 2333/9015* (2013.01); *G01N 2500/10* (2013.01); *G01N 2800/52* (2013.01)

(58) Field of Classification Search
CPC .. C12N 2310/11; C12N 15/113; A61K 31/713
See application file for complete search history.

(56) References Cited

U.S. PATENT DOCUMENTS

| | | |
|---|---|---|
| 2002/0015970 A1 | 2/2002 | Murray et al. |
| 2006/0024288 A1 | 2/2006 | Glidden |
| 2006/0193830 A1 | 8/2006 | Hauswirth et al. |
| 2007/0082347 A1* | 4/2007 | Lanchbury et al. . C12N 15/113 |

FOREIGN PATENT DOCUMENTS

| | | |
|---|---|---|
| EP | 2107375 A1 | 10/2009 |
| RU | 2012100197 | 7/2013 |
| WO | WO 2001/075078 A1 | 10/2001 |
| WO | WO 2015/137881 | 9/2015 |

OTHER PUBLICATIONS

Bertrand et al. (Biochemical and Biophysical Research Communications, 296, 2002, 1000-1004).*
Peiris-Pages et al. (Cell Adhesion & Migration, 6:6, 2012, 561-568).*
Åberg UWN, et al., "Tamoxifen and flaxseed alter angiogenesis regulators in normal human breast tissue in vivo", *PLoS ONE*. (2011);6:e25720.
Antonellis A, et al., "The Role of Aminoacyl-tRNA Synthetases in Genetic Diseases*. Annu. Rev. Genom. Human", *Genet.* (2008); 9:87-107.
Atanur SS, et al., "The genome sequence of the spontaneously hypertensive rat: Analysis and functional significance", *Genome Research*. (2010); 20:791-803.
Bottolo L, et al., "Detection of Expression Quantitative Trait Loci Hot-spots" *Genetics*. 2011; 189:1449-1459 (Dec. 2011).
Curtis C, et al., "The genomic and transcriptomic architecture of 2,000 breast tumours reveals novel subgroups", *Nature*, (2012); 486:346-352.
Damasceno M., "Bevacizumab for the first-line treatment of human epidermal growth factor receptor 2-negative advanced breast cancer". *Curr Opin Oncol*. 2011;23 Suppl: S3-9.
Ewalt and Schimmel, "Activation of Antiogenic Signaling Pathways by Two Human tRNA Synthetases", *Biochem*, 41(45):13344-13349 (2002)).
Ghanipour, A., et al., "The Prognostic Significance of Tryptophanyl-tRNA Synthetase in Colorectal Cancer," *Cancer Epidemiology, Biomarkers & Prevention*, 18(11):2949-2956 (Nov. 2009).
Guo, M, et al., "Essential nontranslational functions of tRNA synthetases", *Nat Chem Biol*. (2013), 9:145-153.
Heid IM, et al. "Meta-analysis identifies 13 new loci associated with waist-hip ratio and reveals sexual dimorphism in the genetic basis of fat distribution", *Nat Genet*. (2010); 42:949-960.

(Continued)

*Primary Examiner* — Amy H Bowman
(74) *Attorney, Agent, or Firm* — Hamilton, Brook, Smith & Reynolds, P.C.

(57) ABSTRACT

The present invention provides methods and agents for modulating WARS2 expression, WARS2 activity, or a combination thereof, thereby modulating angiogenesis. Also provided herein are methods for identifying individuals who could benefit from agents that modulate WARS2 expression, WARS2 activity, or a combination thereof.

12 Claims, 29 Drawing Sheets

Specification includes a Sequence Listing.

(56) References Cited

OTHER PUBLICATIONS

Huang C-C, et al., "Concurrent Gene Signatures for Han Chinese Breast Cancers" *PLoS ONE*. (2013), 8:e76421.

Jia, J., et al., Protection of Extraribosomal RPL13a by GAPDH and Dysregulation by S-Nitrosylation, *Mol. Cell*. (2012), 47:656-663.

Jørgensen, R., et al., "Identification and Characterization of Human Mitochondrial Tryptophanyl-tRNA Synthetase," *The Journal of Biological Chemistry*, 275(22):16820-16826 (Jun. 2000).

Kapoor M, et al., "Evidence for Annexin II-S100A10 Complex and Plasmin in Mobilization of Cytokine Activity of Human TrpRS", *J. Biol. Chem*. (2007), 283:2070-2077.

Kisselev, L.L., "Mammalian tryptophanyl-tRNA synthetases" 75(12): 1027-1039 (1993).

Koza RA., "Synergistic Gene Interactions Control the Induction of the Mitochondrial Uncoupling Protein (Ucp1) Gene in White Fat Tissue", *Journal of Biological Chemistry*, (2000) 275: 34486-34492.

Mazumder B, et al., "Regulated release of L13a from the 60S ribosomal subunit as a mechanism of transcript-specific translational control", *Cell*. (2003), 115:187-198.

McDermott-Roe C, et al., "Endonuclease G is a novel determinant of cardiac hypertrophy and mitochondrial function", *Nature*. (2011), 478:114-118.

Mukhopadhyay R, et al., "The GAIT system: a gatekeeper of inflammatory gene expression", *Trends in Biochemical Sciences*. (2009), 34:324-331.

Notification Concerning Transmittal of International Preliminary Report on Patentability for International Application No. PCT/SG2015/000078, entitled "Methods of Modulating WARS2", dated Sep. 22, 2016.

Notification of Transmittal of The International Search Report and the Written Opinion of the International Searching Authority, or the Declaration, with International Search Report and Written Opinion, issued in International Application No. PCT/SG2015/000078, entitled "Methods of Modulating WARS2", dated May 11, 2015.

Otani A, et al., "A fragment of human TrpRS as a potent antagonist of ocular angiogenesis", *Proc. Natl. Acad. Sci. U.S.A*. (2002); 99:178-183.

Paley, EL, et al., "Hypoxia signature of splice forms of tryptophanyl-tRNA synthethast marks pancreatic cancer cells with distinct metastatic abilities", 40(7): 1043-56 (Oct. 2011).

Petretto E, et al., "Integrated genomic approaches implicate osteoglycin (Ogn) in the regulation of left ventricular mass" *Nat Genet*. (2008); 40:546-552.

Rosen ED, Spiegelman BM. What We Talk About When We Talk About Fat. Cell. (2014) 156: 20-44.

Sengupta, J., et al., "siRNA Knockdown of TrpRS induces apoptosis, Inhibits Cell Proliferation and Arrests Cell Growth in Human Cervical Cancer Cells," *Indian Journal of Scientific Research*, 3(1):1-12 (2012).

Tzima E, "VE-cadherin Links tRNA Synthetase Cytokine to Anti-angiogenic Function", *Journal of Biological Chemistry*, (2004); 280:2405-2408.

Tzima E, et al., "Biologically active fragment of a human tRNA synthetase inhibits fluid shear stress-activated responses of endothelial cells", *Proc. Natl. Acad. Sci. U.S.A*. (2003); 100:14903-14907.

Wakasugi, K., et al., "A Human Aminoacyl-tRNA Synthetase as a Regulator of Angiogenesis," *PNAS*, 99(1):173-177 (Jan. 2002).

Wang, F., et al., "Regulated Capture by Exosomes of mRNA's for Cytoplasmic tRNA Synthetases", *J. Biol. Chem*., (2013), pp. 1-11.

Yu Y. "Crystal Structure of Human Tryptophanyl-tRNA Synthetase Catalytic Fragment: Insights Into Substrate Recognition, tRNA Binding, and Angiogenesis Activity", *Journal of Biological Chemistry*. 2003; 279:8378-8388.

Yuan, W., et al., "Modulation of cellular tryptophan metabolism in human fibroblasts by transforming growth factor-beta: selective inhibition of indoleamine 2,3-dioxygenase and tryptophanyl-tRNA synthetase gene expression", *J. Cell Physiol*, (1998) 177(1): 174-186.

Zeng R, et al., "Different angiogenesis effect of mini-TyrRS/mini-TrpRS by systemic administration of modified siRNAs in rats with acute myocardial infarction", *Heart Vessels*. (2010); 25:324-332.

\* cited by examiner

CLUSTAL 2.1 multiple sequence alignment

```
SEQ ID NO:1  rWARS2  ------------------------------KESGERVFSGIQPSGIPHIGNYIGAIESWV    30
SEQ ID NO:2  mWARS2  MALFSVRKARECWRFIRALHGPAATLAPQKESGERVFSGIQPSGIPHIGNYIGAIESWV    60
SEQ ID NO:3  hWARS2  MALHSMRKARERWSFIRALHKGSAAPALQKDSKKRVFSGIQPTGILHLGNYLGAIESWV    60
                                                   *:* ;****.* :*:*:***** rWARS2  KLQEEYDTVIYSIVDLHSITVPQDPGILQQSILDMTAVLLACGIDPERSILFQQSQVSEH    90
             mWARS2  NLQEEYDTVIYSIVDLHSITVPQDPTVLQQSILDMTAVLLACGINPEKSILFQQSKVSEH   120
             hWARS2  RLQDEYDSVLYSIVDLHSITVPQDPAVLRQSILDMPAVLLACGINPEKSILFQQSQVSEH   120
                     ·**:***:*:***************.:*:*****.*******:**:******:****

rWARS2  TQLSWILTCMVRLPRLQHLHQNKAKAAROMHDGTVGLLTYPVLQAADILCYNSTHVPVGE   150
             mWARS2  TQLSWILTCMVRLPRLQHLEQNKAKAAKOKHDGTVGLLTYPVLQAADILCYKSTHVPVGE   180
             hWARS2  TQLSWILSCMVRLPRLQHLHQNKAANTTKQNHDGTVGLLTPVLQAADILLYKSTHVPVGE   180
                     *****:*********.*::   :.******* ***** *:******* rWARS2  DQVQHMELVQDLARSFWQKYGELFPLPRSILTSMKVKSLRDPSAKMSKSDPDKLATVQI   210
             mWARS2  DQVQHMELVQDLARSFWQKYGEFFPLPKSILTSMKVKSLRDPSSKMSKSDPDKLATVRI   240
             hWARS2  DQVQHMELVQDLAQGFNKKYGEFFVPESILTSMKVKSLRDPSAKMSKSDPDKLATVRI   240
                     ************:. *::***:* * ************:************:* rWARS2  TDSPEEIVRKFRKAVTDFTSEVTYEPDSRPGVSNMVATHAAVSGLSVEEVVRNSAGVDTA   270
             mWARS2  TDSPEEIVQKFRKAVTDFTSEVTYEPDSRAGVSNMVATHAAVSGLSVEEVVRSSAGLDTA   300
             hWARS2  TDSPEEIVQKFRKAVTDFTSEVTYDPAGRAGVSNTVAVRIAAVTGLSVEEVVRSAGMNTA   300
                     ********:*************:* .  .*****.**. .***.********.:*::**

rWARS2  RYKLLVADAVIEKFAPIRSEIEKLMDKDHLRKVLVGSAKAKELASPVEEVKKLVGIL     330
             mWARS2  RYKLLVADAVIEKFAPIRKEIEKLMDKDHLRKVLVGSAKAKELASPVFEEVKKLVGIL    360
             hWARS2  RYKLAVADAVIEKFAPIKREIEKLKDKDHLEKVLQTGSAKAKELAYTVCQEVKNLVGFL    360
                     **** ************ :****** ****:*** :************ .* :**:***:
```

FIG. 13

Human WARS2 (SEQ ID NO:4)

```
ATGGCGCTGCACTCAATGCGGAAAGCGCGTGAGCGCTGGAGCTTCATCCGGGCACTTCAT
AAGGGATCCGCAGCTGCTCCCGCTCTCCAGAAAGACAAGAGCAAGAAGCGAGTATTTCCGGC
ATTCAACCTACAGGAATCCTCCACCTGGGCAATTACCTGGGAGCCATTGAGAGCTGGGTG
AGTTACAGGATGAATATGACTCTGTATTATACAGCATTGTTGACCTCCACTCCATTACT
GTCCCCCAAGACCCAGCTGTCCTTCGGCAGAGCATCCTGGACATGACTGCTGTTCTTCTT
GCCTGTGGCATAAACCGGAAAAAAGCATCCTTTTCCAACAATCTCAGGTGTCTGAACAC
ACACAATTAAGTTGGATCTTTCCTGCATGGTCAGACTACCTGATTACAACATTACAT
CAGTGGAAGGCAAAGACTACCAAGCAGCAGCACGATGGCAGGTGGGCCTGCTCACATAC
CCAGTACTCCAGGCAGCCAGCCGACATTCTGTTGTACAAGTCCACACACGTTCCTGTTGGGGAG
GATCAAGTCCAGCACATGGAACTAGTTCAGGATCCCAGACTCCATCTCACATCCATGAAGAAGTAT
GGGGAGTGTCTTTCCAGTGCCCGAGTGCCATTCTCACATCCATGAAGAAGGTAAAATCCCTA
CGTGATCCTTCTGCCAAAATGTCGAAATCAGACCCTGACAAACTGGCCACCGTCCGAATA
ACAGACAGCCCAGAGAGAGATAGTGCAGAAATTCCGCCAAGGCTGTGACAGACTTCACCTCG
GAGGTCACCTATGACCCGGCTGGCCGGCGTGTCCAACATAGTGGCGGTGCATGCC
GCGGTGACGGGGCTCCGTGGCCAGATGCTGTGATTGAGAAGTTGCCCCAATTAAGCGTGAA
CGCTACAAGTGGCCGTGGCCAGATGCTGTGATTGAGAAGTTGCCCCAATTAAGCGTGAA
ATTGAAAAACTGAAGCTGGACAAGGACCATTTAGAGAAGAAGGTTTACAAATTGGATCAGCA
AAAGCCAAAGAATTAGCATACACTGTGTGCCAGGAGGTGAAGAAATTGGTGGGTTTCTA
TAG
```

FIG. 14

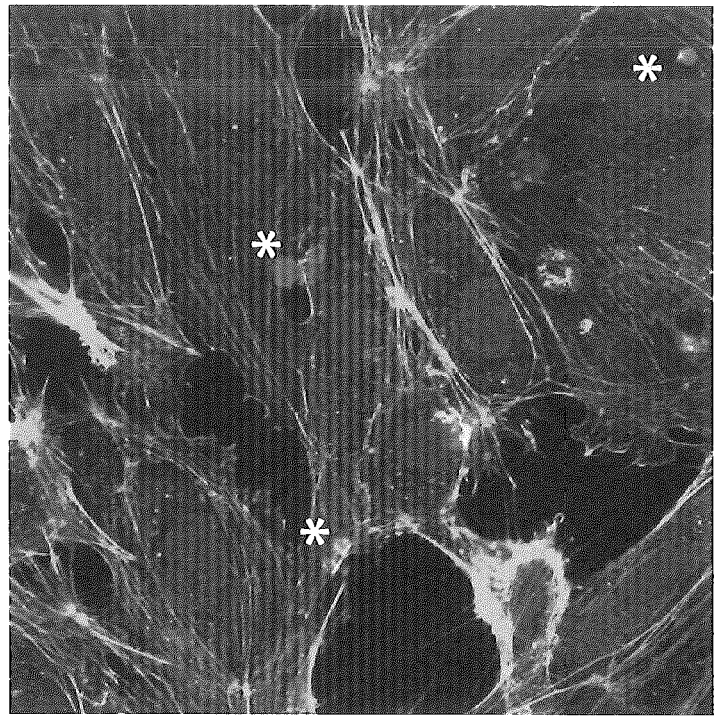
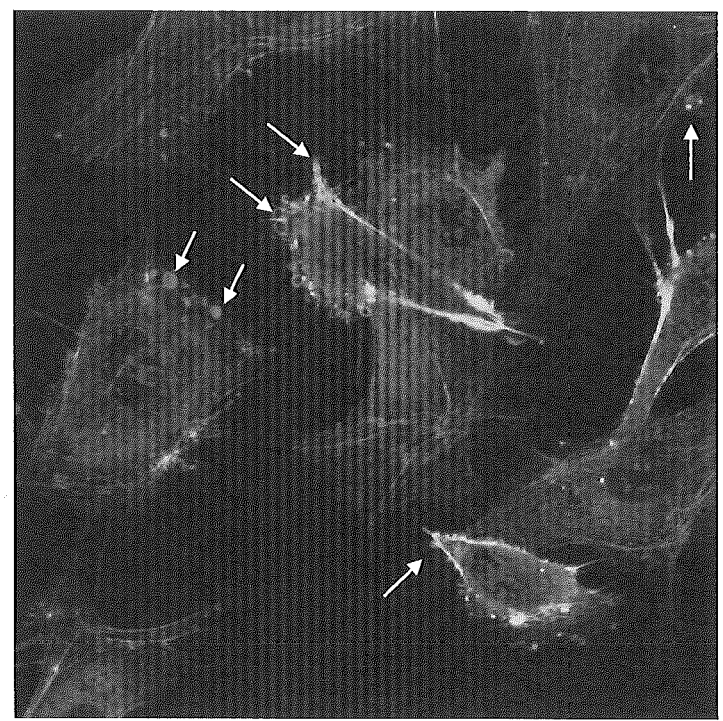
FIG. 17

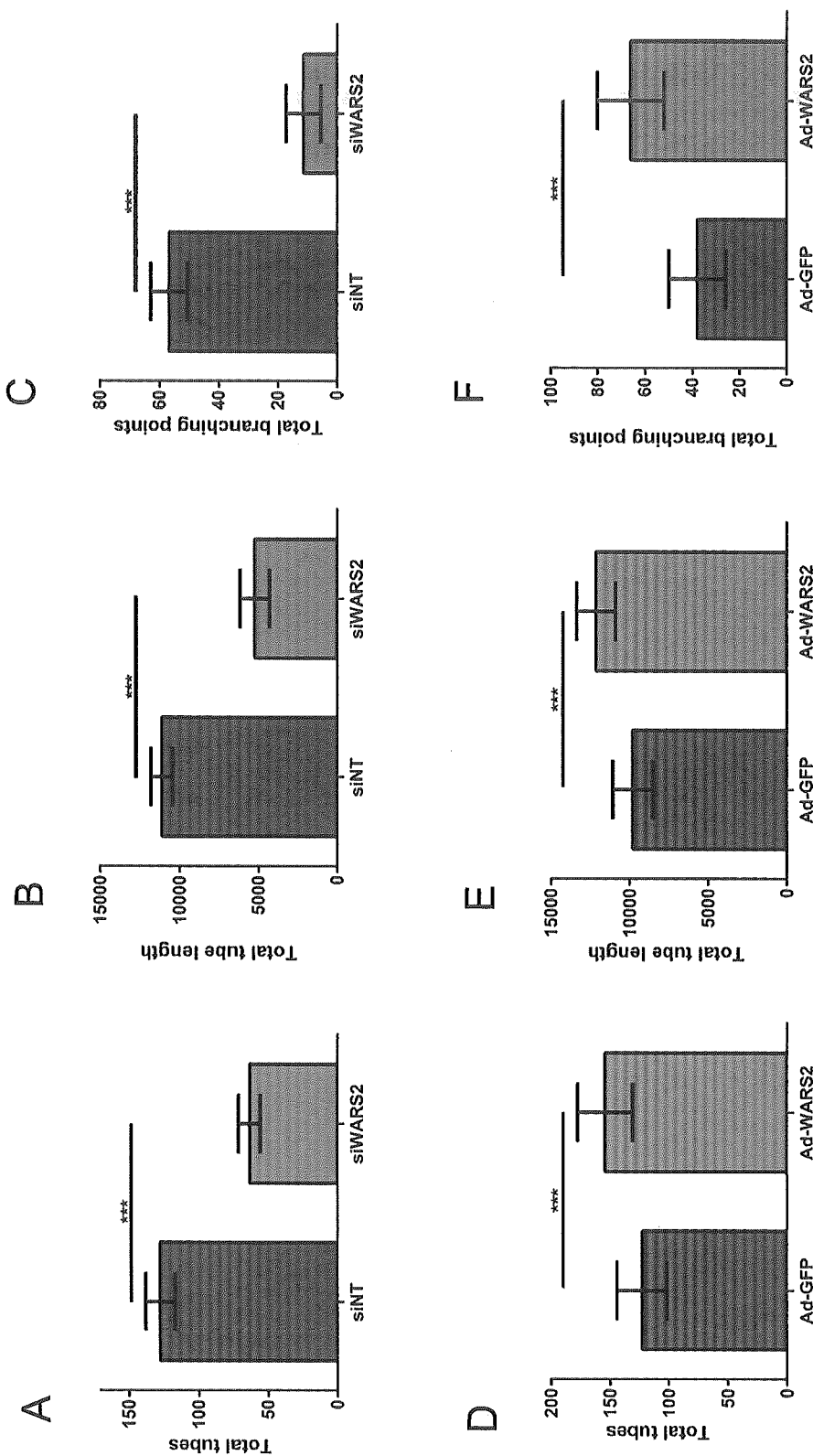
FIGS. 22A-F

METHODS OF MODULATING WARS2

This application is the U.S. National Stage of International Application No. PCT/SG2015/000078, filed Mar. 13, 2015, which designates the U.S., published in English, and claims the benefit of U.S. Provisional Application No. 61/952,510, filed Mar. 13, 2014. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:
a) File name: 44591090002_SEQLISTING_9_9_2016; created Sep. 8, 2016, 22 KB in size. s

BACKGROUND OF THE INVENTION

Proliferation of cells is central to the pathophysiology of various diseases. For example, angiogenesis, which results from uncontrolled proliferation of endothelial cells, plays an important role in, e.g., cancers, diabetic eye disease, macular degeneration, and arthritis.

A need exists for methods of detecting pathological conditions and treating conditions or diseases associated with uncontrolled proliferation of cells, including, for example, proliferation of endothelial cells that contributes to angiogenesis.

SUMMARY OF THE INVENTION

As described herein, mitochondrial tryptophan tRNA synthetase (WARS2) has been identified to play a role in modulating proliferation of cells, in particular, proliferation of endothelial cells, implicating the benefits of modulating WARS2 in various disorders associated with angiogenesis. The present invention provides methods for modulating angiogenesis by controlling WARS2 expression, WARS2 activity, or a combination thereof using various agents including, but not limited to a nucleic acid, a small organic molecule, an antibody, an aptamer, a mutant WARS2, or any combination thereof, as described herein.

In another aspect, the present invention provides methods for modulating proliferation of cells other than endothelial cells, e.g., cancerous cells. Thus, methods for modulating proliferation of, e.g., cancerous cells by controlling WARS2 expression, WARS2 activity, or a combination thereof using various agents are described herein.

Also provided herein are methods of identifying an individual having, e.g., a tumor or cardiovascular disorder, who would benefit from modulating WARS2 expression, WARS2 activity, or a combination thereof.

BRIEF DESCRIPTION OF THE DRAWINGS

FIG. 6A shows that WARS2 silencing (siWARS2) has no effect on WARS transcript expression of splicing. FIG. 6B shows WARS subcellular localization in endothelial cells at baseline and following IFN-gamma stimulation.

FIG. 13 is an alignment of amino acid sequences of rat WARS2 (SEQ ID NO: 1), mouse WARS2 (SEQ ID NO: 2) and human WARS2 (SEQ ID NO: 3). The highlighted sequence "PTGIPHLGNYLGA" shows the position of the lysine residue L that is mutated in mutant WARS2(L53F).

FIG. 14 shows the cDNA sequence of human WARS2 (SEQ ID NO: 4). The highlighted sequences are the regions targeted by siRNAs.

FIG. 17 is confocal imaging which shows that WARS is secreted in exosomes and that expression of WARS2 inhibits the secretion of these exosomes by trapping WARS in the cells. HUVEC cells infected with control virus (Ad. Control, shown in the left panel) or with virus expressing WARS2 (Ad. WARS2, shown in the right panel) were each stimulated with Interferon gamma (IFN-γ) and then stained. In control cells, membrane bound exosomes/micro-vesicles containing WARS are seen budding from the cell's plasma membrane (arrows). In contrast, large amounts of WARS accumulate at the plasma membrane (*), but not in exosomes, in WARS2-infected cells.

FIG. 18A shows genotyping of the 8 bp deletion in wild type BN(Wars2$^{+/+}$) and heterozygous gene targeted BN(Wars2$^{-/+}$) rats that were generated using zinc finger nucleases. Lane 1, homozygous wildtype Wars2$^{+/+}$; lanes 2-6, heterozygous Wars2$^{-/+}$; Lane 7, marker (50 bp, 100 bp and 150 bp). FIG. 18B depicts gene expression of Wars2 in BN and F1(Wars2$^{-/+}$) and F1(Wars2$^{-/L53F}$, compound hypomorphic) rats. *, $P<0.05$; , $P<0.01$; *, $P<0.001$.

FIG. 19A shows capillary blood vessel density is low when Wars2 is low. FIG. 19B shows capillary area is low in the heart when Wars2 is low. FIG. 19C illustrates that coronary flow, that is dependent on capillary density, is low in the heart with low Wars2. Bars, mean; error bars, SEMs. , $P<0.01$; *, $P<0.001$.

FIG. 20A shows that indolmycin inhibits human mitochondrial WARS2 but not human cytosolic WARS activity. FIG. 20B shows decreased activity in the Wars2 mutant rat (having L53F mutation). , $P<0.01$; *, $P<0.001$.

FIGS. 22A-F illustrate effects of WARS2 in an in vitro model of angiogenesis. FIGS. 22A-C show WARS2 loss-of-function as demonstrated by decreased EC tube formation; FIGS. 22D-F show WARS2 gain-of-function using Adenoviral (Ad)-mediated over-expression of WARS2 when compared with GFP. Total EC tubes (FIGS. 22A and 22D), total EC tube length (FIGS. 22B and 22E) and total branching points (FIGS. 22C and 22F). Bars, mean; error bars, SD. ***, $P<0.001$.

FIG. 23A shows super-resolution microscopy of ECs transfected with siNT or siWARS2 and stained for actin (left), mitochondria (middle), and composite images with nuclear stain (right) (scale bar=25 µm). In the presence of siWARS2, the actin stress fibres essentially disappear altogether and cell edges take on a ruffled appearance (left and right panels), while the mitochondria become clumpy (middle and right panels). FIG. 23B indicates EC number in cultures transfected with siNT or siWARS2 for 72 h. Bars, mean; error bars, SD. *, $P<0.01$, ***, $P<0.001$.

FIG. 24A shows that siRNA-mediated inhibition of WARS2 in endothelial cells (ECs) results in multiple cells with two or more incompletely separated nuclei. Nuclei (arrow heads); (bar=50 µm). FIG. 24B is a FACS analysis of the cell cycle in proliferating ECs treated with non-targeting siRNA (siNT) or siRNA against WARS2 (siWARS2); results show a significant reduction in ECs in the S phase and an increased number in the G2/M phase (seen as 4N increasing from 19.62% to 30.81%) with siWARS2. The experiment was repeated (n=3) with similar results.

DETAILED DESCRIPTION OF THE INVENTION

Figure 1A:
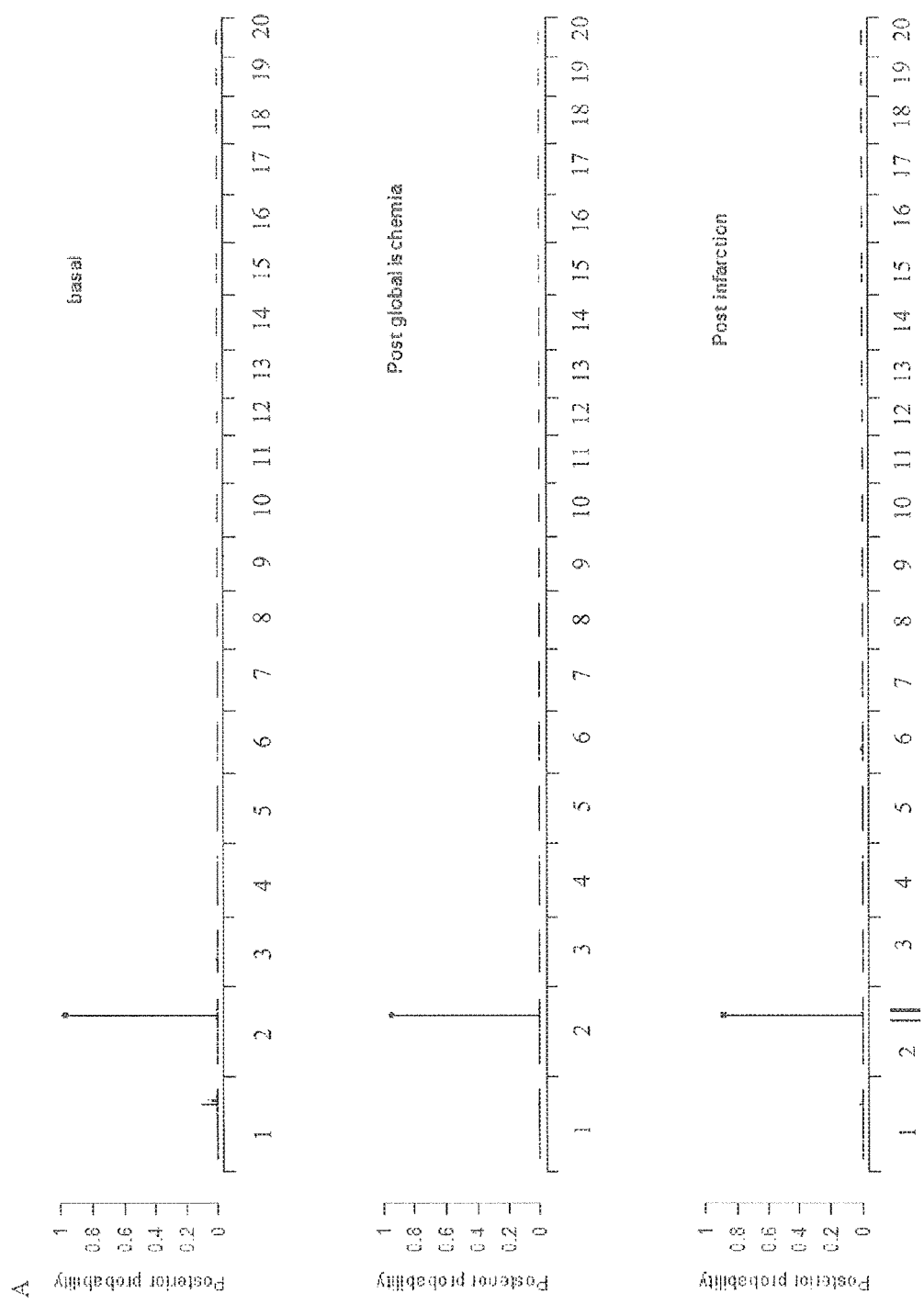
FIGS. 1A-1C show that genetic mapping of coronary flow of the rat genome at three (3) independent time points identifies a single locus on rat chromosome 2q34 that controls coronary flow. 1A: genetic mapping in the F2 cross. Y axis, confidence of significant association (1=100%, redline=threshold for significance); X axis, position in the rat genome. 1B: haplotype refinement of the region using mapping strains and additional strains (BN=Brown Norway, SHR=spontaneously hypertensive rat, LEW=Lewis rat, WKY=Wistar Kyoto rat). 1C: genetic control of gene expression at the locus. Two genes were found to be under strong genetic control, Pex11b and Wars2.

A description of example embodiments of the invention follows.

As described herein, in an experimental rat cross (Brown Norway×Spontaneously Hypertensive rat F2 population), the genetic determinants of coronary flow were mapped and a locus on rat chromosome 2 that genetically controlled blood flow in the heart was identified. The effect was confirmed in a congenic rat that had diminished capillary density. Haplotype mapping and eQTL analysis prioritized tryptophan tRNA synthetase 2 (Wars2; mitochondrial localized) as the candidate gene at the locus and sequencing of Wars2 identified a L53F mutation in a highly conserved ATP binding domain (refer to FIG. 13).

Amino acyl-tRNA synthetases can form hetero-dimeric complexes and WARS2 was observed to bind to WARS that, when cleaved and secreted, inhibits VEGFA signaling and angiogenesis. Binding of WARS2 to WARS was largely abolished in the L53F mutant form. In IFN-γ-stimulated endothelial cells, WARS2 over-expression limited secretion of the anti-angiogenic WARS fragment, whereas WARS2 knockdown increased its release. WARS exhibited non-canonical secretion and, as demonstrated herein, WARS secretion in exosomes. While WARS is mostly localized to the cytosol, increased WARS was found in the mitochondrial compartment and WARS intra-cellular retention and decreased cleavage were observed in the presence of WARS2 over-expression. In a zebrafish model, morpholino-mediated inhibition of Wars2 resulted in diminished blood vessel lumenisation, interruption of arterial structures, and impaired heart function. Moreover, as described herein, inhibition of WARS2 activity or expression results in diminished proliferation of endothelial cells.

Taken together, the data herein identify WARS2 as a novel gene for modulating angiogenesis. Indeed, WARS2 enzyme active site and binding to WARS affects blood vessel formation. As shown herein, targeting WARS2 biologically modulates extracellular vesicle (e.g., exosome) secretion of WARS, as well as proliferation of endothelial cells, and this effect can be used to inhibit aberrant angiogenesis in individual (e.g., human) diseases such as cancers, notably breast cancer where WARS2 is implicated, eye diseases and metabolic conditions such as obesity (where WARS2 mutation has implicated a role in such diseases). The data herein demonstrate that mutation of WARS2 can have a profound effect on the function of WARS, endothelial cell proliferation, and thereby on angiogenesis.

In another aspect, data provided herein show that inhibition of WARS2 also results in a significant reduction on cancer cell numbers, indicating a broader role in the modulation of cell proliferation beyond endothelial cells, including, e.g., modulating the proliferation of cancerous cells per se.

As used herein the term "WARS2" refers to a mitochondrial aminoacyl-tRNA synthetase. Aminoacyl-tRNA synthetases catalyze the aminoacylation of tRNA to their cognate amino acid. Specifically, "WARS2" is the mitochondrial tryptophan tRNA synthetase. Two forms of tryptophan-tRNA synthetase exist, a cytoplasmic form, named WARS, and a mitochondrial form, named WARS2.

As used herein, the human form of, e.g., WARS2, is indicated in all capital letters, wherein the DNA/RNA form is italicized (WARS2) and the protein form is not italicized (WARS2). Generally, non-human forms (e.g., mouse or rat) are indicated as Wars2 in lower case except for the first letter, wherein the DNA/RNA form is italicized (Wars2) and the protein form is not italicized (Wars2).

Accordingly, in one aspect, the present invention is directed to a method of modulating angiogenesis in an individual in need thereof comprising administering an effective amount of an agent that modulates expression of WARS2, activity of WARS2, or a combination thereof.

As used herein, "angiogenesis" refers to the proliferation of endothelial cells which form blood vessels.

As used herein, the terms "modulate(s)" or "modulating" angiogenesis refer to alter(s) or altering angiogenesis. For example, the method of modulating angiogenesis includes inhibiting, enhancing or maintaining angiogenesis. Thus, in another aspect, the present invention is directed to a method of inhibiting angiogenesis in an individual in need thereof comprising administering an effective amount of an agent that inhibits expression of WARS2, activity of WARS2, or a combination thereof.

In some aspects, the method of inhibiting angiogenesis can be used to inhibit angiogenesis caused by, or that occurs as a consequence of, one or more conditions or diseases. For example, the method can be used to inhibit angiogenesis in an individual that has retinopathy (e.g., diabetic retinopathy) or macular degeneration (e.g., age-related macular degeneration (AMD) such as wet AMD or dry AMD). Alternatively, the method of inhibiting angiogenesis can be used to inhibit angiogenesis of a cancer (e.g., to inhibit the growth of blood vessels supporting the growth of a tumor) (Curtis, C. et al., *Nature*, 486:346-352 (2012); Aberg, U W N et al., *PLoS One*, 6e:25720 (2011); Damasceno M et al. *Curr Opin Oncol*, 23 *Suppl*:S3-9 (2011); Huana C-C et al., *PLoS One*, 8e:76421 (2013)) or metabolic conditions such as obesity (Heid et al., *Nature Genetics*, 42:949-960(2010); Rosen E D et al., *Cell*, /56:20-44 (2014); Koza, R A et al., *J Biol Chem*, 275:34486-34492 (2000)).

In other aspects, the invention is directed to a method of treating retinopathy in an individual in need thereof comprising administering an effective amount of an agent that inhibits expression of WARS2, activity of WARS2 or a combination thereof. In a particular aspect, the retinopathy is diabetic retinopathy.

In yet other aspects, the invention is directed to a method of treating macular degeneration (e.g., wet AMD; dry AMD) in an individual in need thereof comprising administering an effective amount of an agent that inhibits expression of WARS2, activity of WARS2 or a combination thereof.

In other aspects, the invention is directed to a method of enhancing angiogenesis in an individual in need thereof comprising administering an effective amount of an agent that enhances expression of WARS2, activity of WARS2 or a combination thereof.

In some aspects, the method of enhancing angiogenesis can be used to enhance angiogenesis in an individual that is undergoing and/or has undergone transplantation (e.g., organ transplantation) or wound healing, or is exhibiting various forms of cardiovascular disease.

As used herein, "cardiovascular disease" includes, but is not limited to: angina, myocardial infarction, heart failure, atherosclerosis, and angiosarcoma.

In another aspect, as described herein, modulation of WARS2 can modulate the multiplication (growth) of cells other than endothelial cells (e.g., cancerous cells). In particular, inhibition of WARS2 expression or WARS2 activity can reduce the number of cancerous cells. Thus, the present invention is directed to a method of modulating cancer cell proliferation in an individual in need thereof comprising administering an effective amount of an agent that modulates expression of WARS2, activity of WARS2, or a combination thereof. As used herein, "cancer cell proliferation" refers to the multiplication of cancer cells per se.

As used herein, the terms "modulate(s)" or "modulating" cancer cell proliferation refer to alter(s) or altering the ability of cancer cells to multiply. For example, the method of modulating cancer cell proliferation includes inhibiting, enhancing, or maintaining the multiplication of cancer cells.

In a particular aspect, the invention is directed to a method of inhibiting cancer cell proliferation in an individual in need thereof comprising administering an effective amount of an agent that inhibits expression of WARS2, activity of WARS2, or a combination thereof.

As described herein, the agent used in the methods modulates (e.g., inhibits, enhances) the expression of WARS2, the activity of WARS2 or a combination thereof. Activities of WARS2 include interaction (e.g., binding) of WARS2 with one or more partners. For example, as shown herein, WARS2 interacts with WARS and proteins of the Gamma-interferon Activated Inhibitor of Translation (GAIT) complex. Specific examples of proteins of the GAIT complex that interact with WARS2 include glutamyl-prolyl tRNA synthetase (EPRS), glyceraldehyde-3-phosphate dehydrogenase (GAPDH), and Ribosomal Protein L 13a (RPL13a). Thus, in some aspects, the agent used in the methods modulates the interaction of WARS2 with WARS, EPRS, GAPDH, RPL13a or a combination thereof.

Any of a variety of agents can be used in the methods provided herein. For example, the agent can be a nucleic acid (e.g., DNA, RNA), a small organic molecule, an antibody, an aptamer, a mutant WARS2, or a combination thereof. Such agents may be readily tested, for example, according to the methods exemplified herein, to assess whether it has a desired effect (e.g., inhibition or activation/enhancement) on WARS2 expression, WARS2 activity, or a combination thereof.

In particular aspects, the agent is a nucleic acid that binds to nucleic acid that encodes all or a portion of WARS2, regulates the expression of WARS2, encodes all or a portion of a polypeptide that interacts with (e.g., binds to) WARS2, and/or regulates the expression of a polypeptide that interacts with WARS2. Examples of such nucleic acids that regulate the expression of a polypeptide that interacts with WARS2, or expression of WARS2 itself include small interfering ribonucleic acid (siRNA), antisense, short hairpin RNA (shRNA), an aptamer, and/or a morpholino oligomer. In other aspects, the agent is a vector that directs expression of WARS2 and/or a polypeptide that interacts with (e.g., binds to) WARS2. In one aspect, the agent is a vector that directs overexpression of WARS2. Additional examples of inhibitory nucleic acids and methods of designing such nucleic acids suitable for use in the present invention are readily available to one of skill in the art. See, e.g., U.S. Patent Application No. 20150017091. In a particular aspect, the agent is a siRNA that reduces or inhibits the expression of WARS2, as exemplified herein. In one aspect, the siRNA pair directed to WARS2 is SEQ ID NOs: 50 and 51; SEQ ID NOs: 52 and 53; or SEQ ID NOs: 54 and 55. In another aspect, the siRNA pair directed to Wars2 is SEQ ID NOs: 48 and 49.

In further aspects, the agent is a small organic molecule that influences, directly or indirectly, WARS2 expression, WARS2 activity, or a combination thereof. Small organic molecules that can modulate WARS2 expression and/or WARS2 activity may be accomplished using standard methods, and as described in any of the assays exemplified herein. If WARS2 expression and/or WARS2 activity is altered in the presence of the agent compared to a control, then the agent modulates WARS2 expression and/or WARS2 activity. In one aspect, the agent is indolmycin or any effective derivative thereof.

In other aspects, the agent is an antibody that influences, directly or indirectly, WARS2 expression, WARS2 activity, or a combination thereof. Methods for identifying, isolating, and producing antibodies, as well as active fragments thereof, directed to any suitable target are well established and known in the art. Unless the context indicates otherwise, the term "antibody" is used in the broadest sense and specifically covers antibodies (including full-length monoclonal antibodies) and antibody fragments, so long as they recognize and bind WARS2. An antibody molecule is usually monospecific, but may also be described as heterospecific or polyspecific. Antibody molecules bind by means of specific binding sites to specific antigenic determinants or epitopes on antigens. "Antibody fragments" comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments. Thus, in one aspect, the agent is an antibody that binds to WARS2 and modulates its activity by, e.g., modulating its binding to WARS. In other aspects, an antibody may target and bind to a protein that modulates WARS2 expression, thereby modulating WARS2 indirectly. Methods for screening the effects of the antibody on WARS2 expression or WARS2 activity may be accomplished using standard methods, and as described in any of the assays exemplified herein.

Methods for preparing polyclonal antibodies are readily available to those skilled in the art. See, for example, Green, et al., Production of Polyclonal Antisera, in: Immunochemical Protocols (Manson, ed.), pages 1-5 (Humana Press); Coligan, et al., Production of Polyclonal Antisera in Rabbits, Rats Mice and Hamsters, in: Current Protocols in Immunology, section 2.4.1 (1992).

Methods for preparing monoclonal antibodies are likewise available to one of skill in the art. See, for example, Kohler & Milstein, Nature, 256:495 (1975); Coligan, et al., sections 2.5.1-2.6.7; and Harlow, et al., in: Antibodies: A Laboratory Manual, page 726 (Cold Spring Harbor Pub. (1988)), which are hereby incorporated by reference. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG), in: Methods in Molecular Biology, Vol. 10, pages 79-104 (Humana Press (1992).

Methods of in vitro and in vivo manipulation of monoclonal antibodies are also available to those skilled in the art. For example, monoclonal antibodies to be used in accordance with the present invention may be made by the hybridoma method first described by Kohler and Milstein, Nature 256, 495 (1975), or may be made by recombinant methods, e.g., as described in U.S. Pat. No. 4,816,567. The monoclonal antibodies for use with the present invention may also be isolated from phage antibody libraries using the techniques described in Clackson et al. Nature 352: 624-628 (1991), as well as in Marks et al., J. Mol. Biol. 222: 581-597 (1991). Additionally, humanizing a monoclonal antibody by recombinant means to generate antibodies containing human specific and recognizable sequences are well known. See, for review, Holmes, et al., J. Immunol., 158:2192-2201 (1997) and Vaswani, et al., Annals Allergy, Asthma & Immunol., 81:105-115 (1998).

In another aspect, the agent is an aptamer that influences, directly or indirectly, WARS2 expression, WARS2 activity, or a combination thereof. An "aptamer" refers to a nucleic acid molecule that is capable of binding to a particular molecule of interest with high affinity and specificity. Aptamers are typically developed to bind particular ligands by employing known in vivo or in vitro selection techniques known as SELEX (Systematic Evolution of Ligands by Exponential Enrichment). Methods of making aptamers are described in, for example, Ellington and Szostak, Nature 346:818 (1990), Tuerk and Gold, Science 249:505 (1990), U.S. Pat. No. 5,582,981, PCT Publication No. WO 00/20040, U.S. Pat. No. 5,270,163, Lorsch and Szostak, Biochemistry, 33:973 (1994), Mannironi et al., Biochemistry 36:9726 (1997), Blind, Proc. Nat'l. Acad. Sci. USA 96:3606-3610 (1999), Huizenga and Szostak, Biochemistry, 34:656-665 (1995), PCT Publication Nos. WO 99/54506, WO 99/27133, WO 97/42317 and U.S. Pat. No. 5,756,291. Aptamers may be used, as appropriate in the present invention, to activate or inhibit expression of WARS2, or bind directly to WARS2 to modulate its activity. Methods for screening and designing aptamers are well established and readily available to one of skill in the art.

In yet other aspects, the agent is a mutant WARS2 that influences WARS2 expression, WARS2 activity, or a combination thereof. For example, as described herein, a WARS2 mutant having the L53F substitution modulates wildtype WARS2 binding to WARS. Accordingly, if it is desired to inhibit WARS2 activity (e.g., to inhibit endothelial cell proliferation, thereby inhibiting angiogenesis; or to inhibit cancerous cell proliferation), a vector carrying the L53F mutant form of WARS2 may be targeted in vivo using known gene delivery methods (see, e.g., U.S. Pat. No. 8,741,279 and Ramamoorth M and Narvekar A. Non-viral vectors in gene therapy—an overview. *J. Clin Diagn Res.* 2015 January; 9(1): GE01-6. doi: 10.7860/JCDR/2015/10443.5394. Epub 2015 Jan. 1.). In another aspect, WARS2 expression may be disrupted altogether in vivo in tumors using known targeted gene disruption methods.

Without wishing to be limited to any one particular mechanism of action, data described herein suggest that WARS2 acts as a modulator of endothelial cell proliferation (and, therefore, of angiogenesis) through one or more mechanisms. For example, the inhibition of WARS2 leads to a dramatic loss of the stress fibres that are required for endothelial cell migration and division. The lack of fibres may inhibit and/or preclude endothelial cell proliferation and the formation of blood vessels (angiogenesis); there is incomplete separation of nuclei and cells are seen to accumulate in G2/M phase. The inability to divide eventually leads to cell death. Similarly, WARS2 may act as a modulator of proliferation of other cell types, e.g., cancerous cells, as a result of incomplete cell division.

In addition, WARS2 may function by adversely affecting energy production in mitochondria. Oxygen consumption is significantly reduced when WARS2 is inhibited. The loss of energy required for cell migration and division similarly may lead to cells being unable to divide, arresting in G2/M phase, and eventually dying. In both cases, the outcome is inhibition of angiogenesis in the context of the failure of endothelial cells to divide and proliferate to form blood vessels. Data herein demonstrate a significant reduction in formation of endothelial cell tubes in the presence of inhibited WARS2. In the context of cancerous cells, the outcome is cell death and decreased proliferation of cancerous cells.

Again, without wishing to be limited to any particular mechanism of action, other data described herein suggest that WARS2 acts as a modulator of angiogenesis by interacting with and inhibiting the secretion of WARS from exosomes. In experiments described herein, WARS2 gain of function decreased WARS secretion. A decrease in WARS secretion would be expected to have downstream effects on angiogenesis.

Accordingly, in other aspects, the invention is directed to a method of identifying angiogenic potential of a tumor in an individual in need thereof. As used herein "angiogenic potential" of a tumor refers to the ability of the body to stimulate tumor growth due to the proliferation of blood vessels that penetrate into the tumor, and e.g., supply nutrients and oxygen to, and/or remove waste products from the tumor. In a particular aspect, the angiogenic potential of a tumor refers to the ability of the tumor to invade (invasiveness potential) and/or metastasize (metastatic potential) into tissue (e.g., tissue proximal or distal to the site of the tumor).

In one aspect, the method comprises determining a level of WARS in one or more extracellular vesicles (EV), such as one or more exosomes, and/or contents thereof obtained from the individual compared to a control. An increased level of WARS in the one or more EVs and/or contents thereof compared to the control indicates a lower likelihood of proliferation of blood vessels that penetrates into (e.g., supplies nutrients and oxygen to, and/or removes waste products from) the tumor, and thus, a tumor with low angiogenic potential in the individual. A decreased level of WARS in the one or more EVs and/or contents thereof compared to the control indicates a higher likelihood of proliferation of blood vessels that penetrates into (e.g., supplies nutrients and oxygen to, and/or removes waste products from) the tumor, and thus, a tumor with high angiogenic potential in the individual. The method can further comprise obtaining one or more EVs and/or contents thereof from the individual.

In a particular aspect, the method of identifying angiogenic potential of a tumor in an individual in need thereof comprises obtaining one or more EVs (e.g., exosomes) and/or contents thereof from the individual; and determining a level of WARS in the one or more EVs and/or contents thereof compared to a control. An increased level of WARS in the one or more EVs and/or contents thereof compared to the control indicates a lower likelihood of proliferation of blood vessels that penetrates into the tumor, and thus, a tumor with low angiogenic potential in the individual. A decreased level of WARS in the one or more EVs and/or contents thereof compared to the control indicates a higher likelihood of proliferation of blood vessels that penetrates into the tumor, and thus, a tumor with high angiogenic potential in the individual.

As used herein, extracellular vesicles (EVs) are vesicles that are released (e.g., secreted) by a (one or more) cell. In particular aspects, the EVs are exosomes, which are about 30-100 nm membrane vesicles, of endocytic origin secreted by most cell types (e.g., in vivo; in vitro). In yet other aspects, the EVs are ectosomes, which are about 100-1000 nm membrane vesicles, of endocytic origin secreted by most cell types (e.g., in vivo; in vitro). EVs are also found in vivo in body fluids (e.g., blood, urine, amniotic fluid, malignant ascites, bronchoalveolar lavage fluid, synovial fluid, and breast milk) and tissues. Methods of obtaining and analyzing EVs and the contents of one or more EVs are known to those of skill in the art, See, for example, Wang et al., *J Biol Chem*, published online Sep. 3, 2013 which is incorporated herein in its entirety. In particular aspects, the one or more EVs are isolated, purified, substantially purified, and/or partially purified.

The method of identifying angiogenic potential of a tumor can further comprise obtaining a sample (a biological sample) that comprises one or more EVs. The sample can be obtained from a biological fluid, a biological tissue or a combination thereof. Examples of biological samples for use in the methods include biological fluids (e.g., blood, serum, urine, amniotic fluid, malignant ascites, bronchoalveolar lavage fluid, synovial fluid, breast milk) and biological tissue (e.g., organ tissue, tumor tissue) and the like.

The method of identifying angiogenic potential of a tumor can further comprise treating the individual based on the angiogenic potential of the tumor. For example, the method can further comprise treating an individual having a tumor with high angiogenic potential with an anti-angiogenic treatment and/or a treatment other than an anti-angiogenic treatment. Alternatively, the method can further comprise treating an individual having a tumor with low angiogenic potential with a treatment other than an anti-angiogenic treatment (e.g., a chemotherapeutic agent that does not inhibit angiogenesis), or treating the individual with an anti-angiogenic treatment and a treatment other than an anti-angiogenic treatment. In certain aspects, the individual is treated with an effective amount of an agent that inhibits WARS2 expression, WARS2 activity, or combination thereof, if the level of WARS is decreased in the one or more EVs and/or contents thereof compared to the control. As will be apparent to those of skill in the art, a variety of controls can be used in the method of identifying angiogenic potential of a tumor. In one aspect, the control is a level of WARS in one or more EVs obtained from one or more individuals without a tumor (e.g., in one of more samples comprising EVs from an individual without a tumor such as one or more healthy individuals).

In another aspect of the present invention, there is provided a method of identifying angiogenic potential in an individual having a cardiovascular disorder. As used herein, "angiogenic potential" of a cardiovascular condition refers to the ability of the body to modulate (i.e., increase or decrease) cardiovascular responses due to the proliferation of blood vessels that provide coronary blood flow to the heart.

In one aspect, the method comprises determining a level of WARS in one or more extracellular vesicles (EV), such as one or more exosomes, and/or contents thereof obtained from the individual having a cardiovascular disorder compared to a control. An increased level of WARS in the one or more EVs and/or contents thereof compared to the control indicates low or reduced angiogenic potential in the individual, and thus, low coronary blood flow into the heart, which may lead to, e.g., angina and heart failure. A decreased level of WARS in the one or more EVs and/or contents thereof compared to the control indicates high or increased angiogenic potential in the individual, which may lead to, e.g., increased atherosclerosis. In certain aspects, high or increased angiogenic potential is associated with obesity as a result of the growth of fat cells. The method can further comprise obtaining one or more EVs and/or contents thereof from the individual.

In a particular aspect, the method of identifying angiogenic potential in an individual having a cardiovascular disorder comprises obtaining one or more EVs (e.g., exosomes) and/or contents thereof from the individual; and determining a level of WARS in the one or more EVs and/or contents thereof compared to a control. The control may be a level of WARS in one or more EVs obtained from one or more individuals without a cardiovascular condition.

The method of identifying angiogenic potential in an individual having a cardiovascular disorder can further comprise obtaining a sample (a biological sample) that comprises one or more EVs. The sample can be obtained from a biological fluid, a biological tissue or a combination thereof. Examples of biological samples for use in the methods include biological fluids (e.g., blood, serum, urine, amniotic fluid, malignant ascites, bronchoalveolar lavage fluid, synovial fluid, breast milk) and biological tissue (e.g., organ tissue, tumor tissue) and the like.

The method of identifying angiogenic potential in an individual having a cardiovascular disorder can further comprise treating the individual based on the identified angiogenic potential of the individual having a cardiovascular disorder. For example, the method can further comprise treating an individual having a cardiovascular condition with low or reduced angiogenic potential, as compared to a control, with a suitable therapeutic to alleviate or prevent angina or heart failure. In another example, the method can further comprise treating an individual having a cardiovascular condition with high or increased angiogenic potential, as compared to a control, with a suitable therapeutic to alleviate or prevent the effects of atherosclerosis. In certain aspects, the individual is treated with an effective amount of an agent that enhances WARS2 expression, WARS2 activity, or combination thereof, if the level of WARS is increased in the one or more EVs and/or contents thereof compared to the control to treat, e.g., angina or heart failure. In other aspects, the individual is treated with an effective amount of an agent that inhibits WARS2 expression, WARS2 activity, or combination thereof, if the level of WARS is decreased in the one or more EVs and/or contents thereof compared to the control to the effects of, e.g., atherosclerosis.

In other aspects, the invention is directed to a method of determining whether an individual in need thereof will benefit from anti-angiogenesis treatment. The method comprises performing genomic analysis of all or a portion of the individual's chromosome 1, wherein the portion comprises TTCATATTCTGTCGAGACACCCATC[C/G]CCCTGT-GTTTCACTTGTCTGATTA C (SEQ ID NO: 38), and detecting at least one allele at position 26 of SEQ ID NO: 38. If at least one allele is a G at position 26 of SEQ ID NO: 38, then the individual will benefit from anti-angiogenesis treatment. In some aspects, one allele at position 26 of SEQ ID NO: 38 in the individual is a G and the other allele is a C (the individual is heterozygous for the alleles at position 26, G:C). In other aspects, both alleles at position 26 of SEQ ID NO: 38 in the individual are G (the individual is homozygous for the alleles at position 26, G:G). In yet other aspects, both alleles at position 26 of SEQ ID NO: 38 in the individual are C (the individual is homozygous for the alleles at position 26, C:C). In a particular aspect, the individual has a tumor.

The portion of chromosome 1 which comprises SEQ ID NO: 38 comprises position 119,503,593-119,504,093 of chromosome 1 based on the Human February 2009 (GRCh37/hg19) assembly for *Homo sapiens* produced by the Genome Reference Consortium.

A variety of genomic analysis methods can be used in the methods of determining whether the individual will benefit from an anti-angiogenic treatment. Examples of such methods include sequencing analysis (next generation sequencing), electrophoresis (gel, capillary, temperature gradient gel electrophoresis), polymerase chain reaction (high-resolution melting analysis), mass spectrometry, single strand conformation polymorphism (SSCP), electrochemical analysis (using ferrocenyl naphthalene diimide), high performance liquid chromatography (HPLC) (denaturing HPLC), enzyme analysis (restriction fragment length polymorphism (RFLP), flap endonuclease, primer extension, 5'-nuclease, oligonucleotide ligation), hybridization analysis (dynamic allele-specific hybridization, allele-specific oligonucleotide (aso) analysis, molecular beacons, microarrays (SNP microarrays), mismatch binding proteins or a combination thereof.

The method of determining whether an individual in need thereof will benefit from anti-angiogenesis treatment can further comprise comparing the detection of the at least one allele at position 26 of SEQ ID NO: 38 from the individual to a control. Any suitable control can be used including the allele that is present in one or more individuals that respond to anti-angiogenesis treatment, do not respond to anti-angiogenesis treatment or a combination thereof.

The method of determining whether an individual will benefit from an anti-angiogenesis treatment can further comprise obtaining a sample (a biological sample) from the individual. The sample can be obtained from a biological fluid, a biological tissue or a combination thereof. Examples of biological samples for use in the methods include biological fluids (e.g., blood, serum urine, amniotic fluid, malignant ascites, bronchoalveolar lavage fluid, synovial fluid, breast milk) and biological tissue (e.g., organ tissue, tumor tissue) and the like.

The method of determining whether an individual will benefit from an anti-angiogenesis treatment can further comprise treating the individual having at least one allele that is a G at position 26 of SEQ ID NO: 38 with an anti-angiogenic treatment. A variety of anti-angiogenic treatments are known to those of skill in the art and include inhibiting vascular endothelial growth factor (VEGF), VEGF receptor-2 (VEGFR), platelet derived growth factor (PDGF), Tie-1 receptor (Tie-1R), Tie-2 receptor (Tie-2R), placental growth factor (PlGF) or a combination thereof.

As used herein an "individual" refers to an animal, and in a particular aspect, a mammal. Examples of mammals include primates, a canine, a feline, a rodent, and the like. Specific examples include humans, dogs, cats, horses, cows, sheep, goats, rabbits, guinea pigs, rats and mice.

The term "individual in need thereof" refers to an individual who is in need of treatment or prophylaxis as determined by a researcher, veterinarian, medical doctor or other clinician. In one embodiment, an individual in need thereof is a mammal, such as a human.

The need or desire for administration according to the methods of the present invention is determined via the use of well-known risk factors. The effective amount of a (one or more) particular agent (e.g., composition) is determined, in the final analysis, by the physician in charge of the case, but depends on factors such as the exact condition and/or disease to be treated, the severity of the condition and/or disease from which the patient suffers, the chosen route of administration, other drugs and treatments which the patient may concomitantly require, and other factors in the physician's judgment.

An effective amount of an agent that modulates WARS2 is administered to an individual in need thereof. As used herein, "effective amount" or "therapeutically effective amount" means an amount of the active composition that will elicit the desired biological or medical response in a tissue, system, subject, or human, which includes alleviation of the symptoms, in whole or in part, of the condition and/or disease being treated.

The composition can be administered in a single dose (e.g., in a day) or in multiple doses. In addition, the composition can be administered in one or more days (e.g., over several consecutive days or non-consecutive days).

Nucleic acids that modulate WARS2 expression and/or WARS2 activity can be delivered to cells, both in vitro and in vivo, by a variety of methods known to those of skill in the art, including direct contact with cells (e.g., "naked" siRNA) or by in combination with one or more agents that facilitate targeting or delivery into cells. Such agents and methods include lipoplexes, liposomes, iontophoresis, hydrogels, cyclodextrins, nanocapsules, micro- and nanospheres and proteinaceous vectors (e.g., Bioconjugate Chem. (1999) 10:1068-1074 and WO 00/53722). The nucleic acid/vehicle combination may be locally delivered in vivo by direct injection or by use of an infusion pump. The nucleic acids can be delivered in vivo by various means including intravenous, subcutaneous, intramuscular or intradermal injection or inhalation.

The use of a composition comprising surface-modified liposomes containing poly (ethylene glycol) lipids (PEG-modified, or long-circulating liposomes or stealth liposomes) are also well known. These formulations offer a method for increasing stability of a liposome or lipoplex solutions by preventing their aggregation and fusion. The formulations also have the added benefit in vivo of resisting opsonization and elimination by the mononuclear phagocytic system (MPS or RES), thereby enabling longer blood circulation times and enhanced tissue exposure for the encapsulated drug. Such liposomes have also been shown to accumulate selectively in tumors (Lasic et al., Science 1995, 267, 1275-1276; Oku et al., 1995, Biochim. Biophys. Acta, 1238, 86-90). The long-circulating liposomes enhance the pharmacokinetics and pharmacodynamics of DNA and RNA. Long-circulating liposomes also protect the siRNA from nuclease degradation.

The nucleic acid agents that modulate expression of WARS2 and/or WARS2 activity may be formulated as pharmaceutical compositions. The pharmaceutical compositions may be used as medicaments or as diagnostic agents, alone or in combination with other agents. For example, one or more siRNAs of the invention can be combined with a delivery vehicle (e.g., liposomes) and excipients, such as carriers, diluents. Methods of lipid-mediated delivery of nucleic acids are well known (see, e.g., U.S. Patent Application No. 20150017091). Other agents such as preservatives and stabilizers can also be added. Methods for the delivery of nucleic acid molecules are known in the art and described, e.g., in Akhtar et al., 1992, Trends Cell Bio., 2, 139; Delivery Strategies for Antisense Oligonucleotide Therapeutics, ed. Akhtar, 1995, Maurer et al., 1999, Mol. Memb. Biol., 16, 129-140; Hofland and Huang, 1999, Handb. Exp. Pharmacol., 137, 165-192; and Lee et al., 2000, ACS Symp. Ser., 752, 184-192, U.S. Pat. No. 6,395,713 and PCT WO 94/02595. The nucleic acids can also be administered in combination with other therapeutic compounds, either administrated separately or simultaneously, e.g., as a combined unit dose. In one embodiment, the invention includes a pharmaceutical composition comprising one or more nucleic acid (e.g., siRNA) according to the present invention in a physiologically/pharmaceutically acceptable excipient, such as a stabilizer, preservative, diluent, buffer, and the like.

The pharmaceutical composition comprising an agent that modulates WARS2 expression and/or WARS2 activity can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrrolidone, sodium saccharine, cellulose, magnesium carbonate, etc.

The agents that modulate WARS2 expression and/or WARS2 activity can also be administered as part of a combinatorial therapy with other compounds (e.g., vascular endothelial growth factor (VEGF); an inhibitor of VEGF such as WARS, VEGF receptor-2 (VEGFR), platelet derived growth factor (PDGF), Tie-1 receptor (Tie-1R), Tie-2 receptor (Tie-2R), YARS1 (mini Yars1) (Ewalt and Schimmel, Biochem, 41(45):13344-13349 (2002)); placental growth factor (PlGF) or a combination thereof).

The agent can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active compound. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

The compounds are administered in a therapeutically effective amount. The amount of compounds that will be therapeutically effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the formulation will also depend on the route of administration, and the seriousness of the symptoms of an angiogenic disease, a vascular disease, a heart disease, or a circulatory disease, and should be decided according to the judgment of a practitioner and each patient's circumstances. Effective doses may be extrapolated from dose-response curves derived from in vitro or animal model test systems.

In another aspect, the invention is directed to a method of identifying an agent that modulates WARS expression and/or WARS activity. The method comprises determining WARS expression and/or WARS activity from one or more EVs (e.g., exosomes) obtained from a cell, tissue and/or organism that has been contacted with an agent to be assessed; and comparing the WARS expression and/or WARS activity to a control, wherein if the WARS expression and/or WARS activity is altered in the presence of the agent compared to the control, then the agent modulates WARS expression and/or activity. The method can further comprise contacting the cell, tissue and/or organism with the agent to be assessed. The method can also further comprise obtaining the one or more EVs from the cell, tissue and/or organism that has been contacted with an agent to be assessed.

In a particular aspect, the invention is directed to a method of identifying an agent that modulates WARS expression and/or activity comprising contacting a (one or more) cell, a tissue and/or an organism (that comprises one or more EVs such as exosomes) with an agent to be assessed; obtaining one or more EVs from the cell, tissue and/or an organism after contact with the agent; determining the WARS expression and/or activity in the one or more EVs obtained from the cell, tissue and/or organism after contact with the agent; and comparing the WARS expression and/or activity to a control. If the WARS expression and/or activity is altered in the presence of the agent compared to the control, then the agent modulates WARS expression and/or activity.

Determination of an EV's WARS expression includes determining the amount of WARS expressed within, or secreted from the EV. Determination of an EV's WARS activity includes determining whether WARS is secreted from the EV and whether, or the extent to which, WARS interacts with (e.g., binds to; associates with) WARS2.

In some aspects, the EV's WARS expression and/or activity is decreased after contact with the agent compared to the control. In other aspects, the EV's WARS expression and/or activity is increased after contact with the agent compared to the control.

As will be apparent to those of skill in the art, a variety of controls can be used in the methods of the invention. An example of a suitable control is the WARS expression and/or activity in one or more EVs obtained from a cell, tissue and/or organism that is not contacted with the agent.

In some aspects, the cell, tissue and/or organism contacted with the agent to be assessed can be from the same individual. In other aspects, the cell tissue and/or organism can be from different individuals of the same species. In yet other aspects, the cell, tissue and/or organism can be from different species.

EXEMPLIFICATION

Example 1

Identification of WARS2 as a Novel Gene for Coronary Flow and Capillary Density

Methods

Rat Parental Strains

Four parental Strains were studied: Spontaneously hypertensive rat (SHR) was included as a hypertensive strain whereas Brown Norway (BN), Wistar Kyoto (WKY) and Lewis were included as normotensive control strains. 12 to 14 weeks old male rats were phenotyped at a rate of two animals/day. All rats were purchased from Charles River UK Limited (Margate, UK).

BN-SHR F2 Population

Rats were bred by a monogamous mating system. BN females were crossed with SHR males to produce BN×SHR (BXH) F1 animals and a reciprocal cross was performed to obtain SHR×BN (HXB) animals. F1 BXH animals were intercrossed to produce F2 BXH animals and F1 HXB animals were intercrossed to produce an F2 HXB animals. Animals were maintained at the Central Biomedical Services facility, Imperial College, London and housed at a maximum of five per cage. The animals had ad libitum access to standard rat chow and sterile water. Except for breeding purposes, animals were separated according to sex. They were maintained on twelve hour diurnal cycles by automatic light switching. Colonies were regularly tested for specific pathogens by using sentinels kept in separate cages. All procedures were performed in accordance with the UK Animals (Scientific Procedures) Act of 1986.

Blood Pressure (BP)

BP was measured using cannulation of the carotid artery in each animal before cardiac excision for ex vivo phenotyping. An ultra-miniature 2 mm pressure catheter (MPVS-Ultra Single Segment Foundation System, ADI instruments) was used. The pressure catheter was calibrated against an external manometer before measurement. Animals were then anaesthetized using inhaled 4% Isoflurane. The carotid region was exposed, an arteriotomy was performed and the catheter was put into place. Data was then captured continuously by LabchartPro software (ADI instruments) and analyzed off line. After carotid cannulation the concentration of inhaled Isoflurane was gradually reduced from 4% to 1.5% to allow the BP to reach physiological level. After recording the BP data, pressure catheter was withdrawn from the vessel which was then tied off prior to CF measurement.

Coronary Flow (CF)

CF was measured using a Langendorff preparation. Following excision, the heart was immediately placed in ice-cold Kreb's buffer and transferred to the ex vivo perfusion apparatus. Aorta was clamped onto the cannula by a bulldog clamp and secured using 3/0 silk. Heart was perfused with a modified Krebs-Henseleit buffer solution, prepared as suggested by Sutherland and Hearse. This solution was kept at 37° C. in a jacketed reservoir and continuously gassed with carbogen solution (95% Oxygen, 5% $CO_2$) to maintain a pH of 7.35-7.45. Perfusion was established within no more than three minutes following cardiac excision. Left atrium (LA) was removed and a fluid-filled latex balloon was placed in the left ventricular (LV) cavity. LV contractility (LV dP/dtmax) and LV relaxation (dP/dtmin) were derived from LV pressure. A co-axial bipolar electrode was placed on the right atrium and pacing was commenced at 360 beats per minute. Electrodes were placed on the right atrium and left ventricle to record continuous electrocardiogram. The whole preparation was kept inside a 37° C. maintained container. The perfusate was pumped at constant volume to the heart a 90 mmHg perfusion pressure. CF was measured by an inline ultrasonic flowmeter placed in an assembly proximal to the cardiac chamber, with an air bubble trap that prevented cardiac air embolism. Hemodynamic data was captured continuously by LabchartPro software (ADI instruments) and analyzed off line after the experiment. The isolated heart preparation was studied at baseline for 15 minutes. This was followed by transient one minute global ischemia and reperfusion, to assess maximum hyperemia. Myocardial infarction was subsequently induced by ligation of the proximal LAD for 35 minutes and followed by reperfusion for an hour. Cardiac eluates were collected during baseline, and first 10 minutes of reperfusion for measurement of metabolites levels.

Gene Expression Data

For a subset of the F2 rats, Non-ischemic LVs from the F2 rats were isolated after CF measurements, and stored at −80° C. for gene expression analysis. Total of 118 RNA samples were processed in batches of twelve using Maxwell 16 system RNA purification kits (Southampton Science Park, Southampton, UK). In each sample, 200 µL of lysate was added for each 25 µg of tissue and the sample was homogenized until no solid sample was visible. 200 µL of the sample-lysate were then diluted in 400 µL of RNA dilution buffer and vortexed to ensure complete dissolution. 50 µL of clearing agent was added to sample-lysate to bind DNA at 70° C. The clearing agent-sample mix was then cooled and centrifuged at 12,000 rpm for two minutes. The bottom phase was placed in the Maxwell robot, resulting in a final 40 µL RNA sample in RNAase-free water. RNA purity was then assessed using NanoDrop. RNA integrity was evaluated using Agilent 2100 Bioanalyzer platform and samples with RNA integrity number <8 were discarded.

Expression was measured using Affymetrix Rat GeneChip 1.0 ST. Raw probe intensity was then background-corrected by subtracting the average of background probes with identical GC content. A VSN normalization step (Huber et al.) was then applied to the data and probesets expression of each transcript were summarized using median-polish.

Genotype Data

DNA from the F2 population was extracted from the samples of tail tissue using robotic DNA extraction on the Maxwell 16 system. The quantity and quality of DNA was assessed using NanoDrop™ and Invitrogen's Quant-it assays. High throughput genotyping was performed using Illumina's GolgenGate assay on a custom genotyping bead-chip. 16,543 BN-SHR SNPs were obtained from the STAR consortium (http://rgd.mcw.edu/) and the surrounding 160 bp sequence for each SNP were retrieved based on SHR genome sequence (Atanur et al., *Genome Res,* 20:791-803 (2010). SNPs and their surrounding sequence were submitted to Illumina for bioinformatic assessment, and attributed a quality score. 768 SNPs, uniformly distributed on the genome and with a quality score of 0.95 or more were then selected to constitute the beadchip. Following hybridization and imaging, genotypes were called using the GenomeStudio software, and the GenCall algorithm. Parental and F1 samples were added to the F2 samples as controls of genotyping quality (Parent-Parent-Child errors/P-P-C); sample replicates were also placed on the BeadChips to estimate reproducibility errors. SNPs with bad cluster separation, reduced mean normalized intensity (R<0.2), or low MAF (MAF<0.1) were excluded. SNP showing significant deviation from Hardy Weinberg equilibrium (P<10-3) were also excluded. After genotype filtering, P-P-C accuracy was ~97% and replication error rate was evaluated to be ~0.01%. The overall call rate was of 93%. Missing genotypes were imputed using fastPhase with defaults settings, and two founder haplotypes.

Coronary Flow Mapping

Coronary Flow QTLs were mapped using the matlab implementation of HESS. All 6 coronary flow phenotypes (mean and maximum, 3 time points), were included in the model as dependent variables. Markers in high LD (r2>XX) were removed prior to analysis and SNP genotypes were used as regressors in the model. Default parameters were used for Hierarchical Evolutionary Stochastic Search (HESS). A marginal posterior probability of 0.8 was required to identify genetic regulation of the phenotype by a SNP. The corresponding haplotype was obtained, by taking the range between the two markers surrounding the marker selected by HESS.

eQTL Mapping eQTL were mapped using the ESS++ program. Three mRNA expression levels measured by microarray in the F2 were included in the model as dependent variables and genotypes were used as regressors.

Results

The present study identified WARS2 as a novel gene for coronary flow and capillary density. The genetic control of coronary flow is unknown. Described herein is the study of this in a large F2 intercross experiment in the rat using approaches similar to those described in McDermott-Roe et al., *Nature,* 478:114-118 (2011); Petretto, et al., *Nat Genet,* 40:546-552 (2008).

Coronary flow was measured at three time points in a Brown Norway-Spontaneously Hypertensive rat (BN-SHR) F2 population of 172 rats using Langendorff preparation. The effect of widely accepted determinants of coronary flow in the rat population was studied. While a strong effect of left ventricle relaxation pressure ((dp/dt)min) on coronary flow ($r=-0.34$, $p=4.6\times10^{-6}$) was found, no effect of systolic or diastolic blood pressure was observed ($p=0.19$ and $p=0.36$, respectively) suggesting blood pressure independent mechanisms regulating coronary flow in the rat population.

Maximum and mean coronary flow was mapped at three different time points using HESS (Bottolo et al., *Genetics*, 189:1449-1459 (2011). HESS models multiple phenotypes jointly by taking advantage of the correlation structure between these phenotypes.

Figures 1B, 1C:
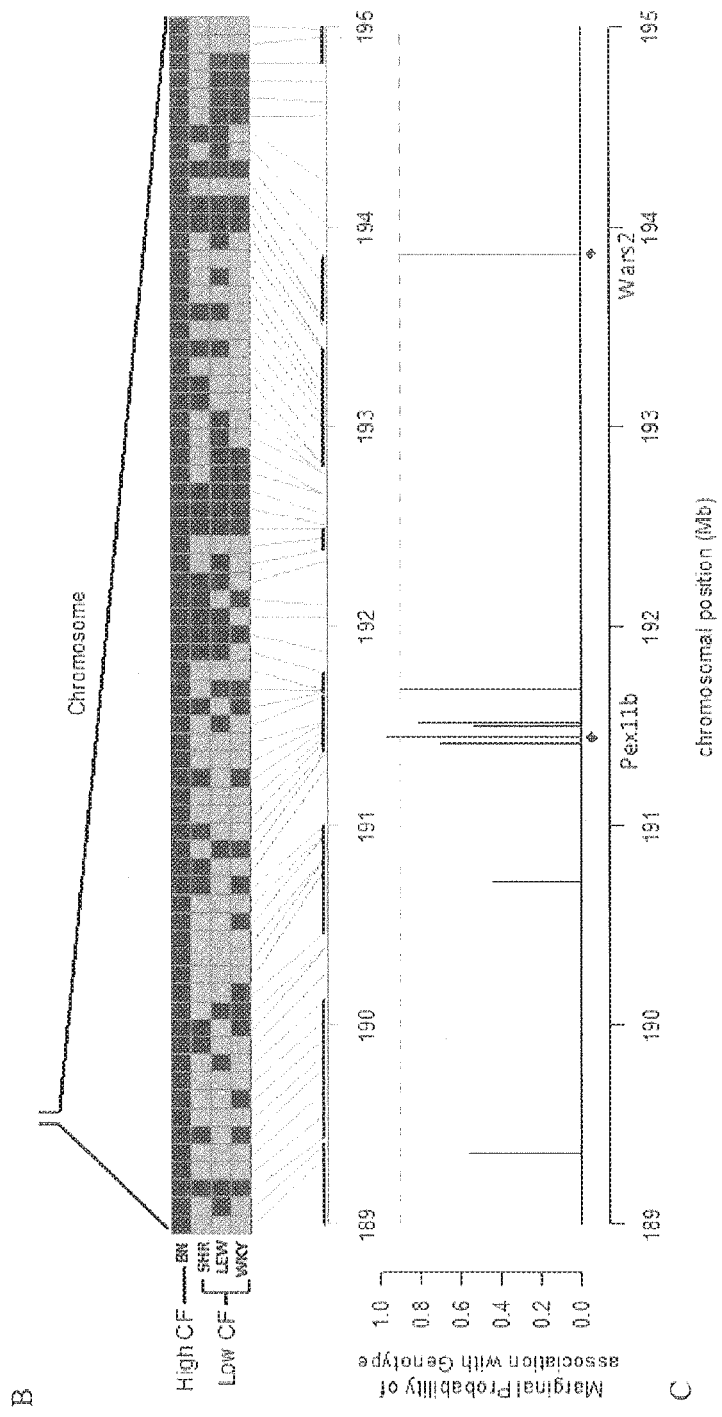

A strong and consistent association of coronary flow measured at basal level, post ischemia and infarction with a single locus located on rat chromosome 2q34 was observed (as shown in FIG. 1). The upper bound of the haplotype limits was derived from the position of the two neighboring markers, indicating that the causal genetic variants can be located between 189.3 and 194.5 Mb.

RNA-seq analysis in left ventricle tissues from BN and SHR identified 42 expressed genes in the region and three of these had a significant eQTL (FIG. 1). Two genes, Wars2 and Cathepsin-S, were found to have non-synonymous variations. Cathepsin-S had variation at a partially conserved protein site and is lowly expressed in the heart. Wars2 on the other hand is a mitochondrial amino acyl tRNA synthetase (aARS) that is expressed highly in the heart and is nuclear encoded and mitochondrial localized; it transfers tryptophan to its cognate tRNA.

A number of aARS (tyrosine ARS (YARS), serine ARS (SARS), cytoplasmic tryptophan ARS (WARS)) have acquired non-canonical roles in vasculogenesis during evolution and cleavage products of WARS have been shown to inhibit VEGF signaling. Wars2 was therefore prioritized as the candidate gene controlling coronary flow at the 2q34 locus in the rat.

Figures 2A, 2B, 2C, 2D, 2E:
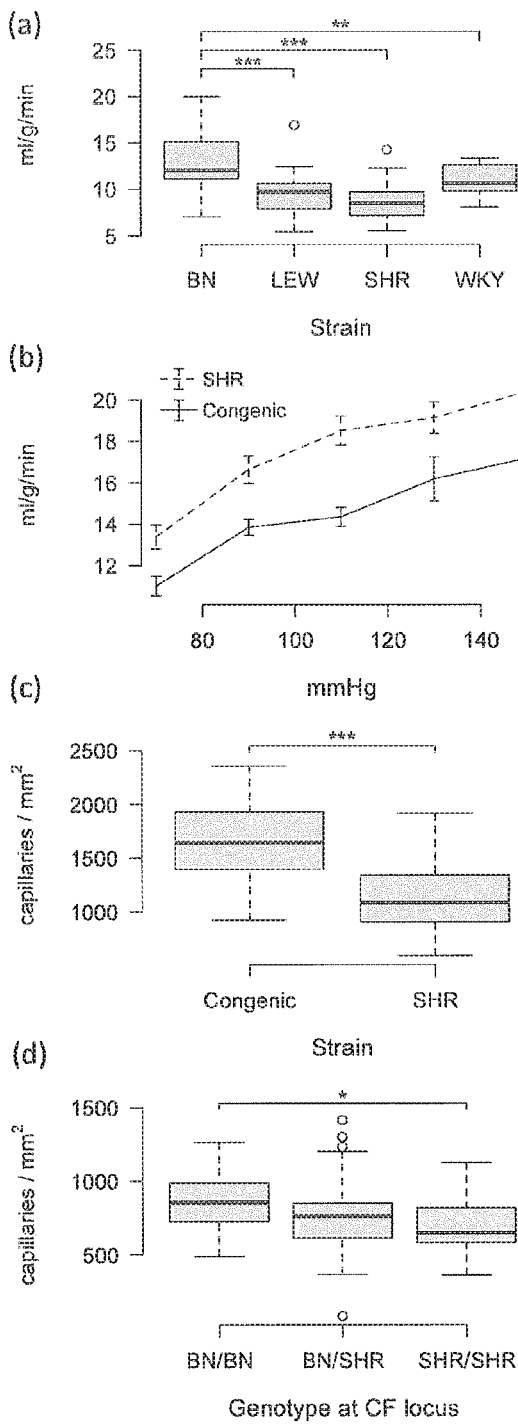
FIGS. 2A-2E show coronary flow in various rat strains. (2A) low flow in Lew, SHR and WKY strains, (2B) rescue of the low flow in the SHR.BN2 congenic. (2C) Different capillary densities in the SHR.BN2 congenic. (2D) Genotype-specific effect of the genotype at the coronary flow (CF) locus with SHR alleles having lower flow. (2E) Mutation of leucine residue 53 to phenylalanine (F) in the SHR (SEQ ID NO: 5), Lew (SEQ ID NO: 6) and WKY (SEQ ID NO: 7) (low blood flow) as compared to the wildtype allele in the BN rat (SEQ ID NO: 8) (high blood flow). Conservation of this residue from mouse (SEQ ID NO: 9), human (SEQ ID NO: 10), chicken (SEQ ID NO: 11), fruit fly (SEQ ID NO: 12), zebrafish (SEQ ID NO: 13) and back to yeast (SEQ ID NO: 14) is shown.

The resistance of the small capillary vessels largely controls blood flow in the heart. The capillary density at the locus in the F2 intercross animals conditioned on genotype and in the intercross was examined and a significant effect of the locus ($P=1.3 \times 10^{-13}$) was found (see FIG. 2).

Example 2

Characterization of WARS2 and its Interaction with WARS

Materials and Methods

The anti-L13a and annexin A were from Cell Signalling. Alexa-488/568 goat anti-mouse/rabbit IgG were from Molecular Probes. Anti-VEGF and GAPDH were from Santa Cruz and all other antibodies were from Abcam. The polyclonal anti-WARS2 rabbit antiserum was obtained after the immunization of rabbits with either the KMS KSD PDK LAT VC (SEQ ID NO: 15) or CIL TSM KKV KSL RDP S (SEQ ID NO: 16) peptides. They were produced and chromatography purified using corresponding peptide by Eurogentec (England). The L53F mutant WARS2 cDNA was created using Quikchange II Site-Directed Mutagenesis Kit (Stratagene) according to the manufacturer's instruction using plasmid construct containing human WARS2 cDNA with C-terminal myc-DDK or GFP (Origene) as template. L53F was verified by nucleotide sequencing. The adenoviruses (Ad-GFP, Ad-WARS2) were purchased from Signa-Gen Laboratories. Human WARS cDNA was synthesised from RNA extracted from human HUVEC cells and the coding region was PCR-amplified using primers containing EcoRI and Kosac sequence in the forward primer and flag sequence and XbaI in the reverse primer. After verifying sequence, WARS was cloned into pLVX-EF1a-IRES-Puro (Clontec).

Cell Culture, Transfection and Adenoviral Transduction

Human embryonic kidney (HEK) 293 cells were maintained in DMEM supplemented with 10% foetal calf serum and 100 U/ml penicillin and 100 μg/ml streptomycin. Human umbilical vein endothelial (HUVEC) cells and medium (EBM- and EBM-2 single Quats) were purchased from Lonza and used prior to passage 7. For plasmid transfections (for HEK293), cells were seeded a day before at 70% confluence and lipofectamine 200 (InvitroGene) transfection reagents were used according to the company's instruction. For HUVEC transfection, Polyplus jetPEI-HUVEC transfection reagent (POLYPLUS-TRANSFECTION Inc. New York) was used according to the company's instruction. For gene transfer, HUVEC were grown to 80% confluence in 6-well plates or T75 flasks. Transduction of cells was performed with a multiplicity of infection (MOI) of 200 plaque-forming units (pfu) in a total volume of 1 ml (6-well plates) or 10 ml (T75 flasks) in HUVEC growth medium. 24 h after infection cells were incubated in medium containing 1% FBS for 1 h and then supplemented with 500 U/ml of human recombinant IFN (R&D Systems) for an additional 24 h before being processed for analysis.

GST Fusion Proteins for Enzyme Assays

WARS2 and WARS2(L53F) cDNAs were cloned into commercial vectors (see table) and expressed using IPTG induction and GSH-bead based purification using standard procedures. Purified proteins were quantified using standard malachite green assays (Cayman chemicals).

RNA Extraction from Cultured Cells

Total RNA was extracted using the RNeasy Mini kit (Qiagen) according to the manufacturer's instructions. Briefly, cells were lysed into 350 μl RLT buffer and applied to Shedder column (Qiagen) and spin for 1 min at 14,000 rpm. The lysates were mixed with an equal volume of 70% ethanol and applied to an RNeasy column, which was then centrifuged and washed using the supplied RW1 and RPE buffers. Finally, total RNA was eluted in a volume of 30 ul RNase-free water and quantified by measuring absorbance at 260 nm using a Nanodrop 1000 (Thermo Fisher Scientific). RNA was stored at −80° C. until required.

Quantitative real time PCR (QPCR) analysis and WARS splicing PCR

Total RNA (1 μg) was reverse transcribed using iScript First Stand cDNA Synthesis protocol (Bio-Rad). The resulting cDNA (1 μl) was subjected to QPCR in a 20 μl reaction using SYBR Green JumpStart Taq ReadyMix (S4438, Sigma) and run on 7900HT Fast Real-Time PCR System (Applied Biosystems). Three independent 6-well cultures per siRNA treatment were used in each of at least three independent experiments and each sample was run in duplicate. All data were analyzed using the 2-ΔΔCT method.

TABLE 1

Primer sequences

| Transcript | Forward primer | Reverse primer |
|---|---|---|
| 28S (HUMAN) | TTAGTGACGCGCATG AATGG (SEQ ID NO: 17) | TGTGGTTTCGCTGGA TAGTAGGT (SEQ ID NO: 18) |
| WARS (HUMAN) | AGCTCAACTGCCCAG CGTGACC (SEQ ID NO: 19) | CAGTCAGCCTTGAAT CCTCCCC (SEQ ID NO: 20) |
| WARS2 (HUMAN) | CTTCTTGCCTGTGGC ATAAAC (SEQ ID NO: 21) | CTTCCACTGATGTAA ATGTTGT (SEQ ID NO: 22) |

TABLE 1-continued

Primer sequences

| Transcript | Forward primer | Reverse primer |
|---|---|---|
| VEGF (HUMAN) | AGCTACTGCCATCCA ATCGC (SEQ ID NO: 23) | GGGCGAATCCAATTC CAAGAG (SEQ ID NO: 24) |

For detecting WARS splicing variants, 1 µl of cDNA for WARS and 1/20 diluted cDNA for 28S were used in 50 µl PCR reaction and 24 cycles were used (determined according to the melting curve in QPCR).

Protein Extraction and Western Blotting

Cells were lysed in cell lysis buffer (9803, Cell Signaling) containing protease inhibitor (Sigma) and phosphatase inhibitor (Halt Phosphase inhibitor Cocktail, Thermo Scientific) and PMSF (0.5 mM Active Motif). Cell lysate was then briefly sonicated and centrifuged for 10 minutes at 14,000 g (4° C.). Supernatants were retained and protein concentrations were determined using the bicinchoninic acid assay with bovine serum albumin standards. Protein samples (20 µg) were separated on 10% or 13% SDS-polyacrylamide gels, transferred to nitrocellulose membranes, and probed with antibodies as described in the figure legends. Immunoreactive bands were visualized with a horseradish peroxidase-conjugated secondary antibody using Peroxide and LumiGlo reagents (Cell Signaling).

siRNA-mediated WARS2 Knockdown

HUVEC cells were seeded in 6-well plates. After 24 h, cells were transfected using DharmaFECT-1 (Thermo Scientific) with WARS2-targeting ON-TARGETplus SMARTpool according to the manufacturer's instructions. For a given transfection, 24 µl DharmaFECT1 and 476 µl opti-MEM (Invitrogen) were mixed in one tube whilst 5 µl of the above WARS2-targeting or scrambled control siRNA (20 µM) was mixed with 490 µl opti-MEM in a second tube. After 5 minutes incubation at room temperature, the aforesaid solutions were mixed and left at room temperature for a further 20 minutes before adding to the cells. The final siRNA concentration was 25 nM. Knockdown efficacy was assessed via QPCR 2 days post-transfection and was found to be at least 85%. The knockdown efficacy could not be determined by western blot since no antibody against WARS2 can detect endogenous WARS2, although two anti-WARS2 antibodies we made can detect WARS2 in lysates from cells expressing WARS2-flag.

Immunofluorescence

Cells were seeded onto sterilized coverslips at approximately 80% confluence. For immunofluorescence analysis, cells were fixed in 3% (w/v) paraformaldehyde for 15 minutes at room temperature, and permeabilised in phosphate buffered saline (PBS) containing 0.3% TritonX100 for 4 minutes and blocked in PBS containing 1% (w/v) bovine serum albumin (BSA). Cells were incubated with primary antibodies for 1 h (diluted 1/40-100) and then with Alexa 488/568-conjugated goat anti-mouse/rabbit IgG (highly cross-absorbed; diluted 1/100) for 1 h, both at ambient temperature. Coverslips were mounted on slides with Vectashield anti-fade mounting medium containing DAPI (Vector Laboratories Inc.). Cells were viewed on a Leica confocal microscope using the 60× oil objective and the images analysed using Leica confocal software (Leica Microsystems (UK) Ltd, Milton Keynes, UK).

Preparation of L53F and Wild-Type WARS2 and WARS Lentivirus

The cDNAs for WARS2 (WT and L53F) tagged with flag or GFP or WARS-flag were subcloned into either pLVX-EF1 alpha-IRES-zs Green (cat no 631982, Clontec) or pLVX-EF1 alpha-IRES-mCherry (cat no 631987 Clontec) or pLVX-EF1 alpha-IRES-Puro vectors (cat no 632183, Clontec) using EcoRI/XbaI sites. The specific viruses were produced using Lenti-X HTX packaging System (631247) in Lenti-X 293T cells according to the manufacturer's protocol (Clontec).

Primers for generating Wars cDNA
F:
(SEQ ID NO: 25)
gggaattcgccgccgcgatcgcCAAAGGATGAAATTGATTCTGCAGT
(EcoRI, Kosac)

R:
(SEQ ID NO: 26)
GctctagattacttatcgtcgtcatccttgtaatcCTGAAAGTCGAA
GGACAGCTT.
(XbaI, flag)

Primers for generating Wars2-FLAG
Forward:
(SEQ ID NO: 27)
GGGAATTCGTCGACTGGATCC Reverse:
(SEQ ID NO: 28)
GctcagaGCCGGCCGTTTAAACCTTATCG
(XbaI)

Primers for generating Wars2-GFP
Forward:
(SEQ ID NO: 29)
GGGAATTCGTCGACTGGATCC

Reverse:
(SEQ ID NO: 30)
5'-GCtctagaGCCGGCCGTTTAAACTCTTTCT-3'
(XbaI)

Mitochondrial Fractionation and Exosome Secretion

To separate cytosol and mitochondria, Mitochondrial Fractionation Kit (Active Motif) was used according to the instruction manual. The purity of mitochondria and cytosolic fractions was verified using antibodies to the mitochondrial protein Complex I (Mitoscience) or to soluble cytosol protein tubulin (Sigma). Exosome collections were generated from HUVEC lysates using the kit (Invitrogen, 4478359) according to the manufacturer's instructions.

Immunoprecipitation and Mass Spectrometry

For immunoprecipitation, cell lysates were prepared in lysis buffer (cell signaling) containing protease inhibitor and phosphatase inhibitor (Halt Phosphase inhibitor Cocktail, Thermo Scientific) and PMSF (0.5 mM). Anti-FLAG M2 Affinity Gel (Sigma) was used for purifying Wars2 flag tagged protein, according to the company's protocol. Before elution, protein-beads were washed with 0.5% NP40 in PBS, then three times in 50 mM ammonium bicarbonate and bound proteins were eluted in 200 µg/mL FLAG peptide (3× flag peptide, Sigma) in 50 mM ammonium bicarbonate. Mass spectrometry was carried, using a full qualitative plus quantitative analysis of total solution digest method.

Results

WARS2 and WARS2(L53F) Localize to Mitochondria in HEK Cells

Figure 3:
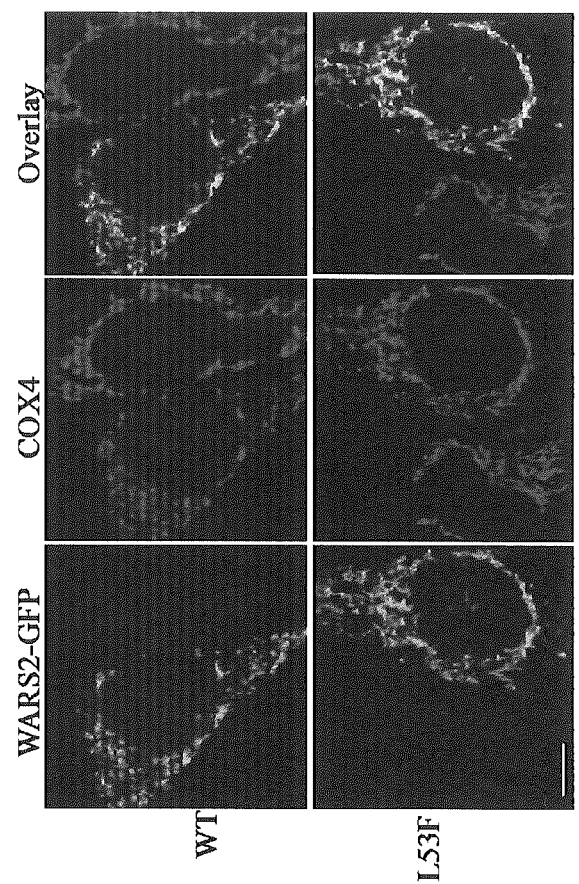
FIG. 3 shows localisation of wild-type (WT) and L53F WARS2 in mitochondria and impaired enzymatic activity of the mutant enzyme. Confocal image analysis of cellular localization of WARS2. Human embryonic kidney cells (HEK293 cells) were transfected with WT or L53F WARS2-GFP and after 24 h cells were fixed, permeabilized and labeled with anti-cox4 (centre two panels). Co-localisation of WARS2 with cox4 is shown in the right-most two panels. Bar size=5 μm.

WARS2 is a nuclear encoded, mitochondrial localized aARS. The localization of human WARS2 and mutated human WARS2(L53F), which has the identical amino acid change as in the rat, was examined. Both mutant and wildtype localized to the mitochondria (shown herein in FIG. 3).

Figure 4:
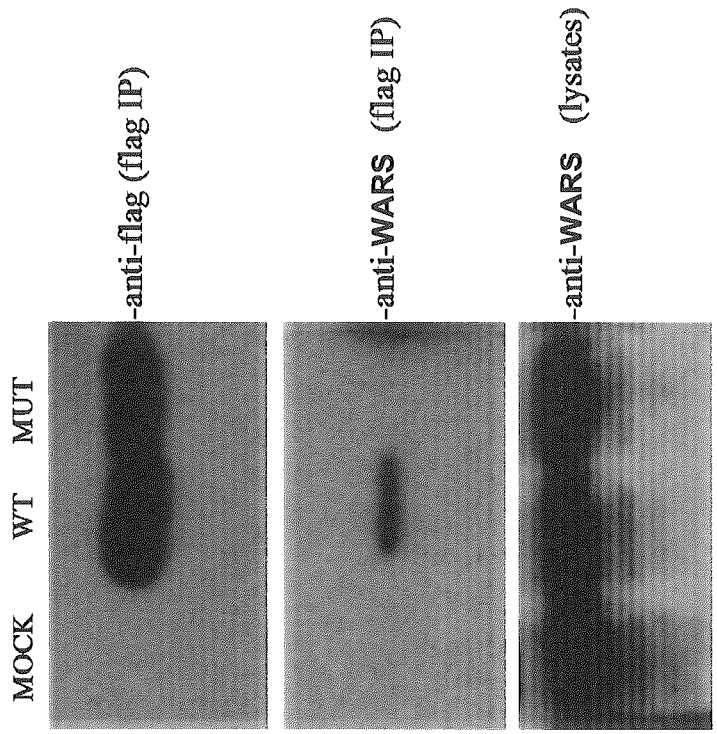
FIG. 4 shows that WARS2 binds to WARS, an effect that is diminished by the WARS2(L53F) mutation in the human WARS2 protein; that is, WARS2(L53F) binds less strongly to WARS. Human Umbilical Vein Endothelial (HUVEC) cells were transfected with no vector (MOCK), flag-tagged wild type WARS2 (WT) or the flag-tagged WARS2(L53F) mutant (MUT) and immunoprecipitated flag proteins analyzed for interaction with WARS.

WARS2 Binds to WARS but Mutant WARS2(L53F) does not aARS can form higher order oligomerisations with themselves and each other, that affect their function. Whether WARS2 bound to its cytosolic counterpart WARS, which has known anti-angiogenic functions, was tested. WARS2 was found to bind to WARS in HUVEC cells. The effect was diminished by the L53F mutation (as seen in FIG. 4).

WARS2 Expression Influences WARS Secretion, an Effect Mediated at a Protein Level WARS fragments have anti-angiogenic activity by binding to VE-Cadherin. The regulation of WARS secretion is unclear. WARS2 overexpression inhibited WARS secretion, whereas WARS2 gene silencing increased WARS secretion. This effect was mediated at the protein level and was not found to be related to splicing or transcriptional effects.

Figure 5:
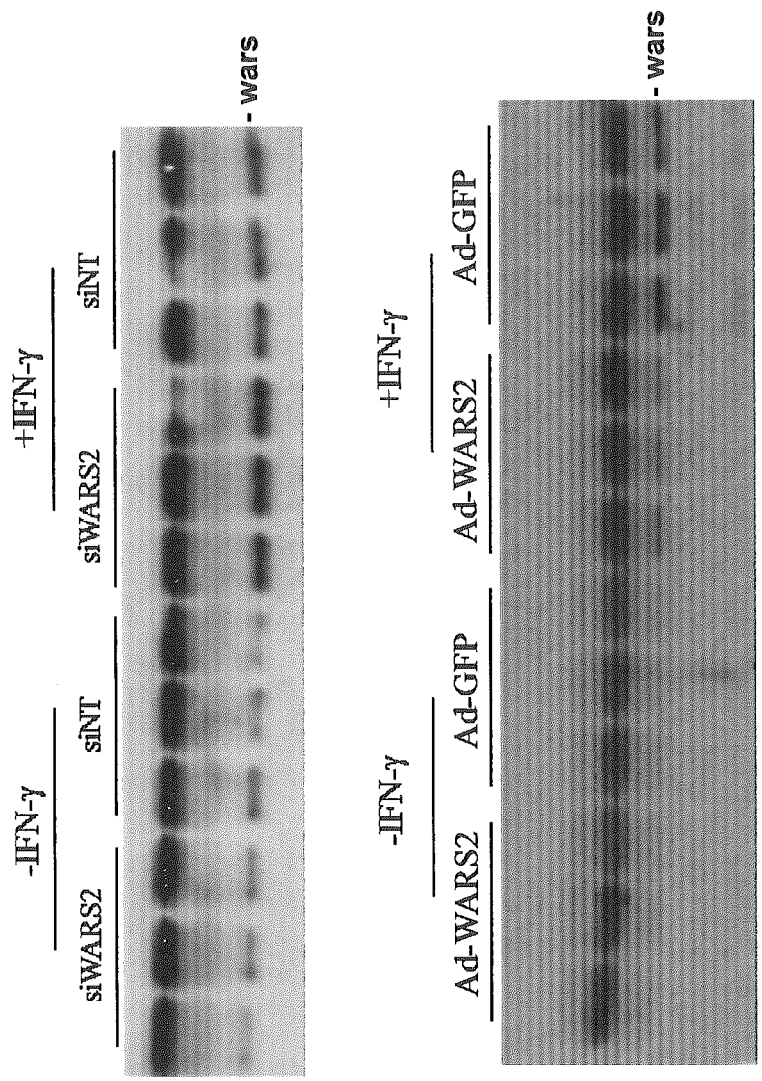
FIG. 5 shows that WARS2 modulates WARS secretion in HUVEC cell media. WARS2 gene silencing (top) using siRNA results in increased WARS secretion in response to IFN gamma stimulation. In contrast, WARS2 over-expression (bottom) using an adenoviral vector inhibits WARS secretion.
Figure 6A:
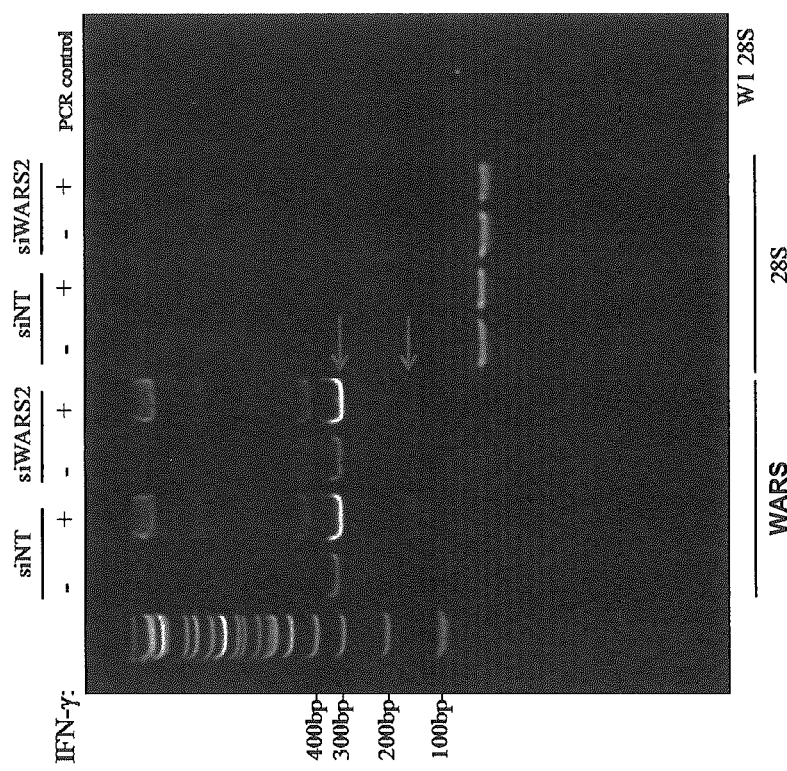
FIGS. 6A and 6B.

HUVEC cells were cultured and either infected with adenovirus encoding WARS2 or transfected with siRNA against WARS2. Control virus and siRNAs were used in all experiments. As compared to control, WARS2 gain of function decreased WARS secretion. As compared to control, WARS2 loss of function increased WARS secretion (see FIG. 5). Taken together, these data show that WARS2 modulates WARS secretion that will have downstream effects on angiogenesis. While it is known that WARS transcription is increased by IFN-gamma stimulation and that there is alternate splicing of WARS, no effect of WARS2 on these events was shown herein (see FIG. 6A). Hence, the effects of WARS2 on WARS are at the protein level.

Cellular Localization of WARS and WARS2 Interaction

WARS is primarily a cytosolic protein but a component of WARS is mitochondrial-localized, and this sub-pool is increased following interferon (IFN)-gamma stimulation in HUVEC.

Figure 6B:
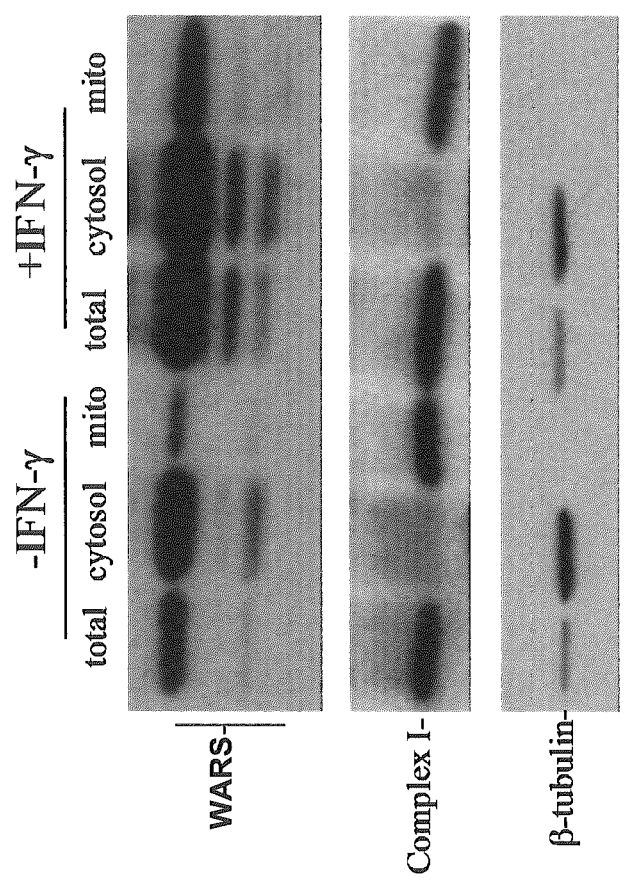

An interaction between WARS and WARS2 was demonstrated herein. In sub-cellular fractionation experiments, WARS was detected in the mitochondria and this sub-pool increased on IFN-gamma stimulation. Hence, the protein-protein interaction is expected to occur in a mitochondrial fraction, and this mitochondrial fraction is likely to play a role in the secretion of WARS from the cell (refer to FIG. 6B).

WARS2 Interacts with Components of the GAIT Complex

To gain further insights into the protein-protein interactions of WARS2, mass spectrometry (MS) was performed. In the experiments herein, the MS data indicated an interaction of WARS2 with EPRS (an aARS), GAPDH and RPL14a. These proteins define, together with NSAP1, the GAIT complex that is important for controlling the protein expression of VEGF and inflammatory genes through binding to the 3'UTRs of target genes.

Figure 7:
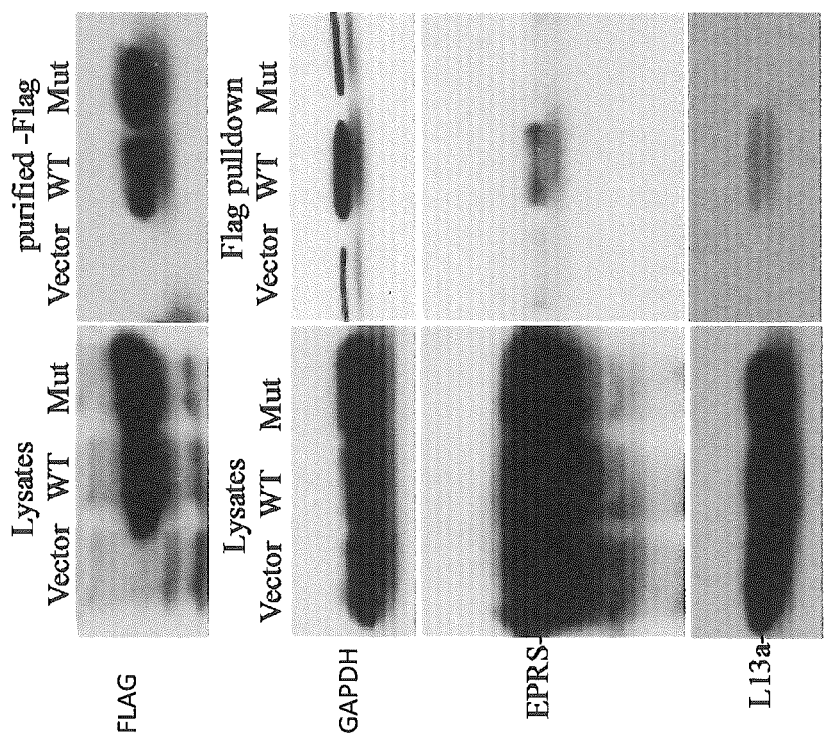
FIG. 7 illustrates that WARS2 binds to components of the GAIT complex, an effect that is not seen in the L53F mutant. HUVEC cells were transfected with Flag-tagged WARS2 or Flag-tagged WARS2(L53F) and flag-purified fractions blotted for interactions with GAIT complex proteins.

MS data alone are inconclusive as many interactions are identified in this type of experiment and downstream validation is required. To validate the interactions, co-IP experiments were performed with WARS2 and the WARS2(L53F) mutant. Interaction of WARS2 (but not the L53F mutant) with EPRS, GAPDH and RPL14a was documented (as shown in FIG. 7).

Figure 8:
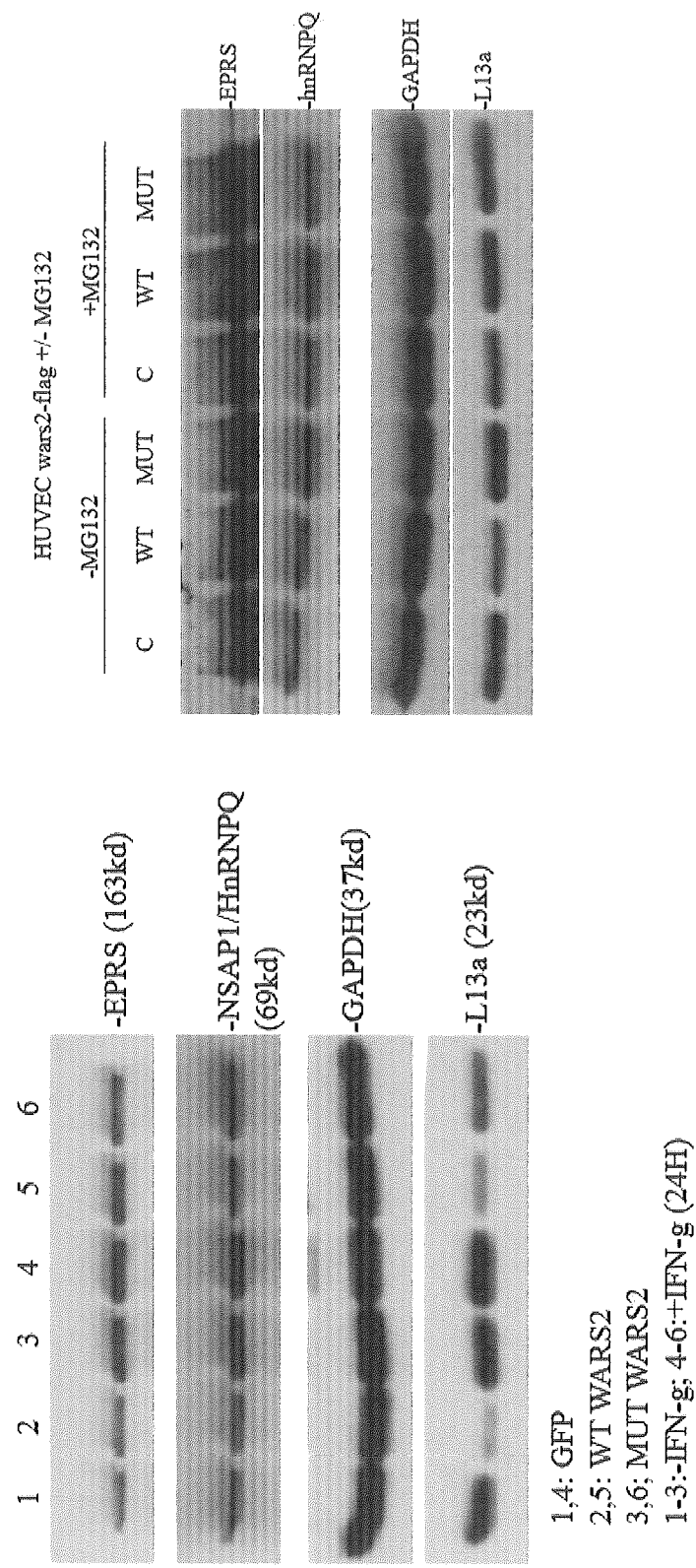
FIG. 8 shows that WARS2 over-expression causes proteosomal degradation of the critical GAIT component RPL13a that can be reversed by the addition of the inhibitor MG132. The mutant WARS2(L53F) has no effect on L13a expression.

Furthermore, as shown herein, over-expression of WARS2 caused dramatic loss of RPL14a by targeting it to the proteasome, an effect that could be reversed by the proteasome inhibitor MG132 (refer to FIG. 8).

These data show that WARS2 acts at a second level in controlling VEGF activity, here by modulating the activity of the GAIT complex that controls the translation of VEGF in addition to the translation of a number of cytokines and chemokines (e.g., CXCL13, CCL22, CCL8, and CCR3).

WARS Undergoes Non-Canonical Secretion Via an Exosome/Micro-Vesicle Pathway

Figure 9:
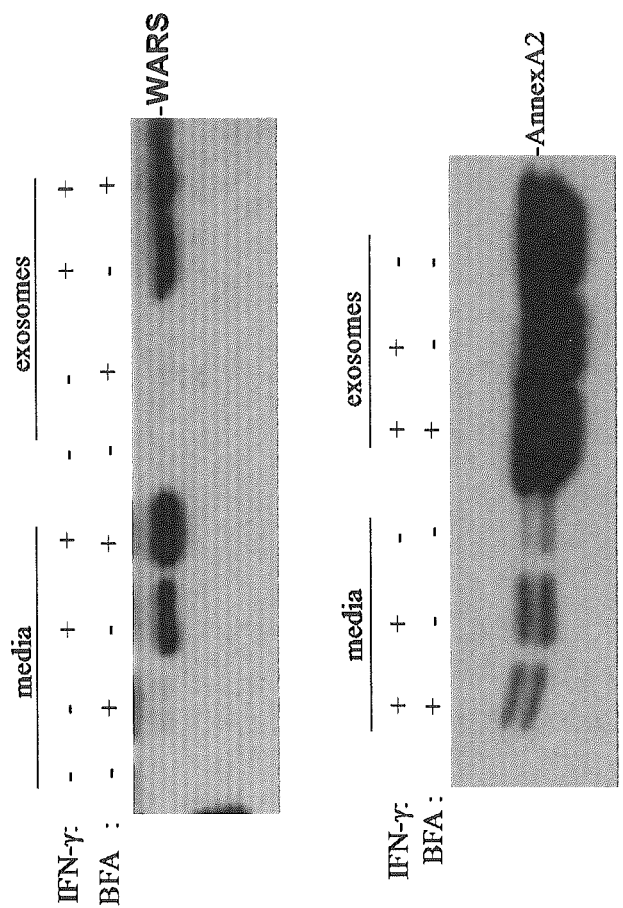
FIG. 9 indicates WARS is secreted from HUVEC into the media in exosomes, an effect that is not inhibited by brefeldin A (BFA). AnnexA2=Annexin A.

Previous studies have shown that WARS is secreted but the pathway of secretion, while non-canonical, has not been characterised. The effects of brefeldin A (an agent that inhibits golgi-mediated secretion) on WARS secretion was examined in HUVEC cells. No effect was observed, as previously described. Further investigation Showed WARS secretion was in exosomes, an effect that was inhibited by WARS2 (FIG. 9). This defines a novel secretion pathway for WARS in exosomes.

Example 3

WARS2 Loss of Function in the Zebrafish Results in Impaired Angiogenesis and Impaired Cardiac Function Methods Morpholino experiments in the zebra fish and imaging of the zebra fish vessel formation were performed using standard approaches.

Results

Figure 10:
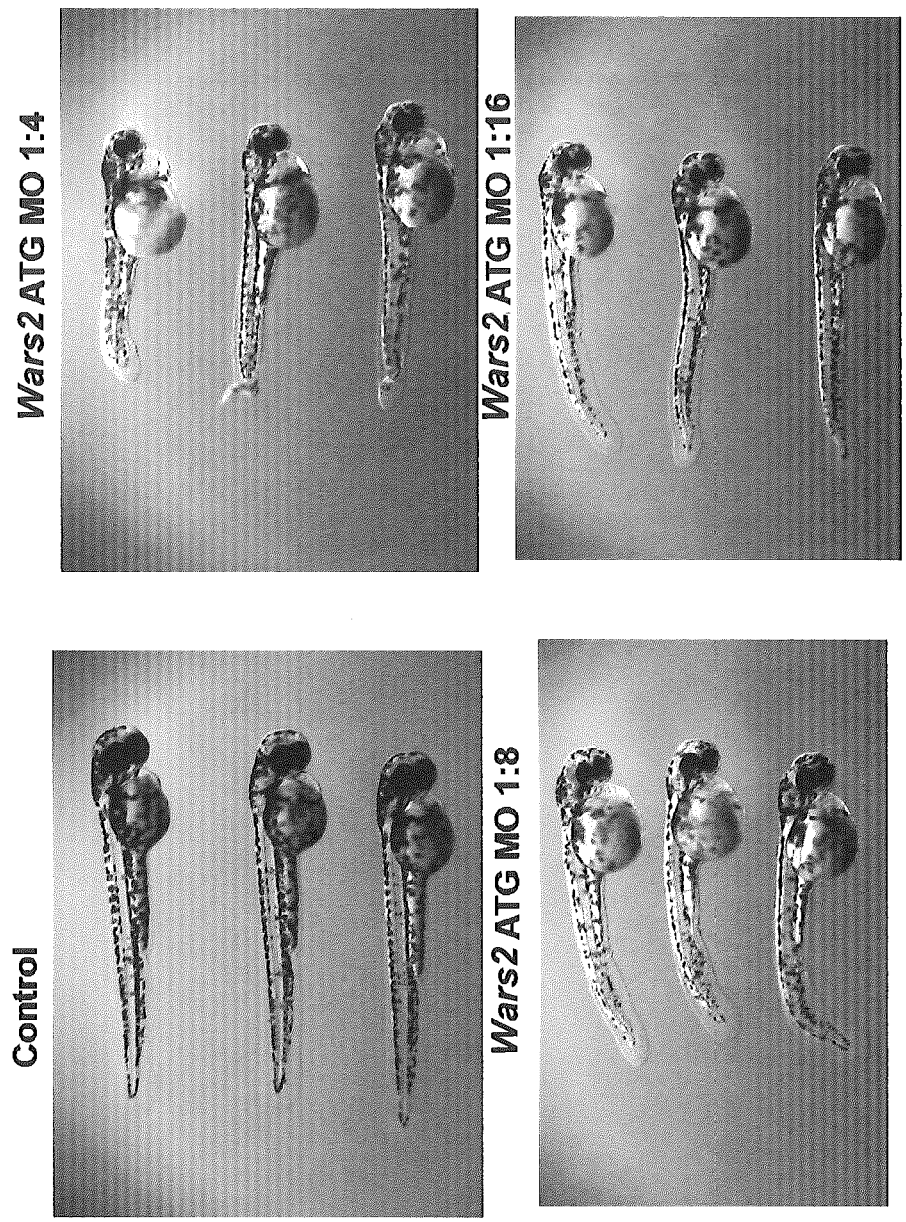
FIG. 10 shows dose-dependent effects of silencing the zebrafish Wars2 gene using a morpholino against Wars2 start codon (ATG MO). The effect was reversed by over-expression of human WARS2 protein.
Figure 11:
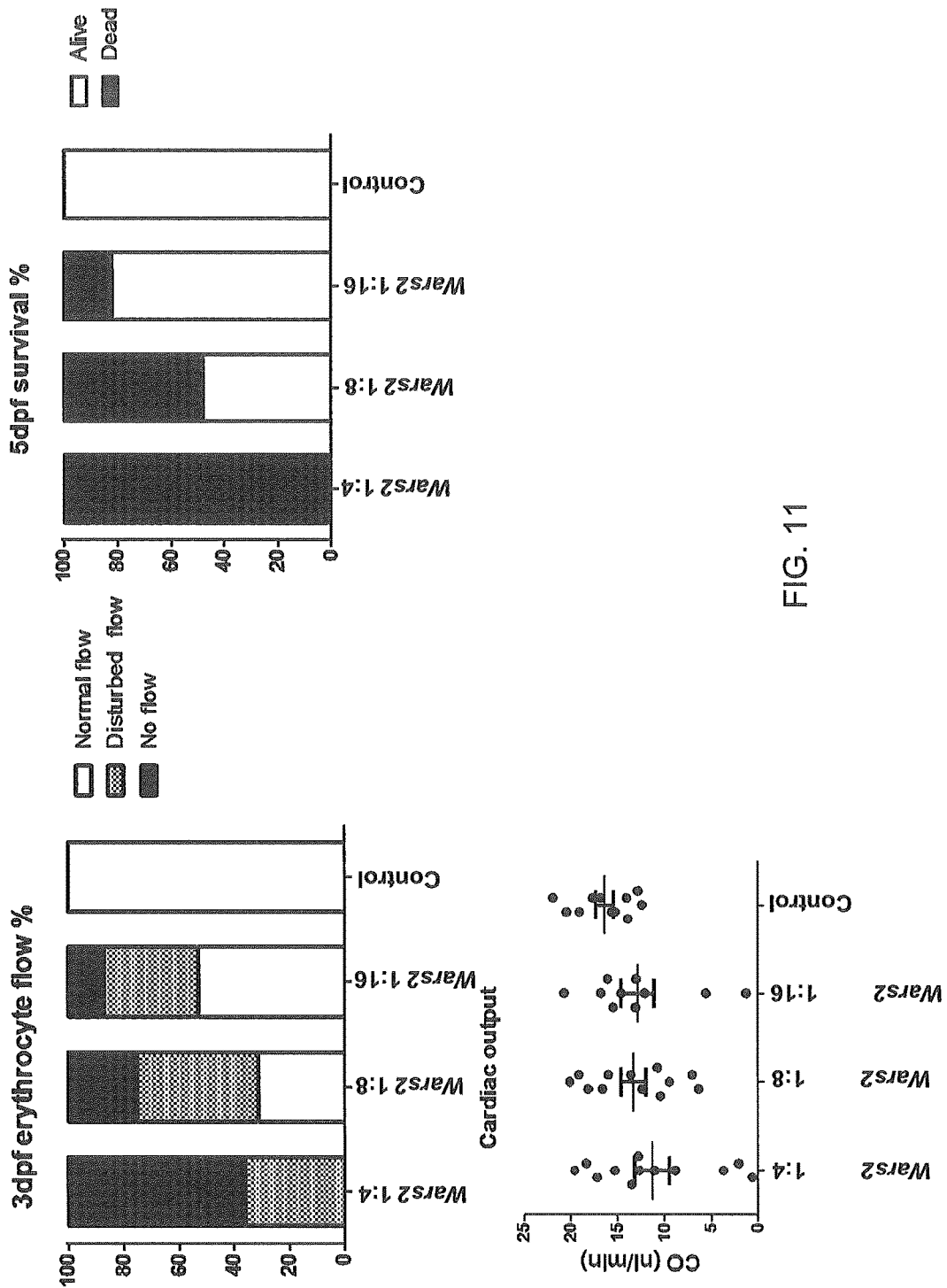
FIG. 11 shows dose-dependent effects of silencing the zebrafish Wars2 gene, using a morpholino against Wars2 start codon, on blood flow (top left), survival (top right) and heart function (bottom left). CO=cardiac output; dpf=days post fertilization. Bars, mean; error bars, SEMs.
Figure 12:
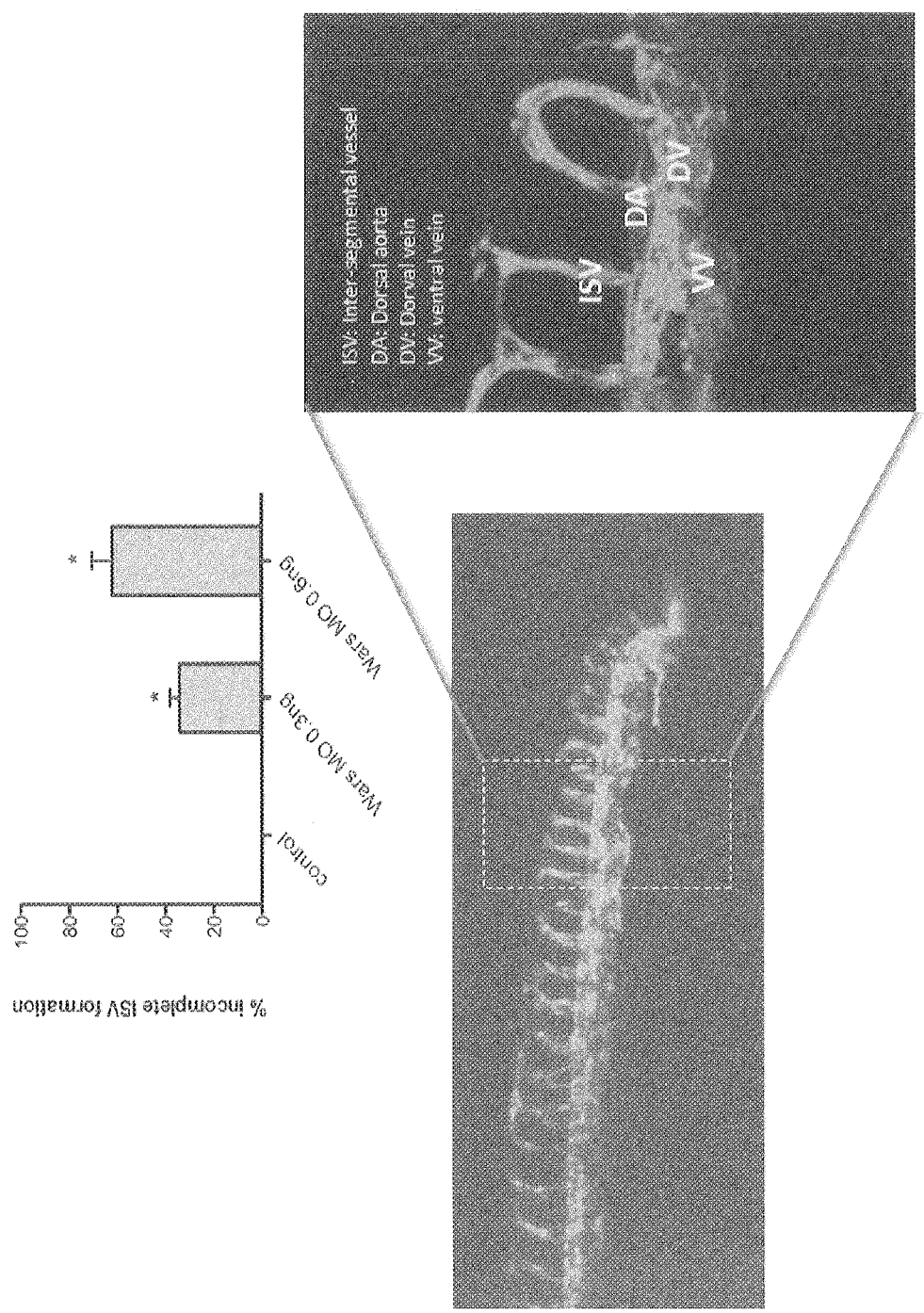
FIG. 12 shows abnormal blood vessel formation in the Flk-GFP fish with Wars2 inhibition, and quantification of the dose-dependent effect (bottom left).

To examine the in vivo effects of Wars2 on vascular genesis and the heart, Wars2 activity was inhibited in the zebra fish using morpholinos against the first codon of Wars2. There were marked effects on fish morphology and survival that were due to defects in blood vessel formation and heart function that are summarized in FIGS. 10-12.

Example 4 siWARS2 Knockdown in Human Embryonic Kidney (HEK)293 Cells

Methods

HEK cells were seeded the day before transfection on 10 cm dish. At a density of ~50%, transfection was performed using RNAimax (manufacturer's protocol). siRNA was prepared by using a mixture of 120 nM siRNA and 20 µl lipofectamin RNAimax in 1 ml OPTIMEM. Cells were incubated, washed 1× with PBS, and then covered with 5 ml OPTIMEM and the lipofectamin/siRNA mixture added dropwise. Cells were incubated (6 h) and media then changed to (DMEM/10% FBS). RNA was extracted as per protocol (Qiagen). RNA quantification was assessed using Nanodrop and the quality was determined based on OD ratio 260 nm/280 nm. Reverse transcription was performed using 1 µg RNA (Biorad iScript™ cDNA synthesis protocol) and QPCR performed using the QuantiFAST SYBR green protocol.

```
Primers for human WARS2
F
                                          (SEQ ID NO: 31)
GCCACCGTCCGAATAACAGA R
                                          (SEQ ID NO: 32)
CATGCACCGCCACTATGTTG
```

```
Primers for human GAPDH
F
                                              (SEQ ID NO: 33)
GGAGTCAACGGATTTGGTCG R
                                              (SEQ ID NO: 34)
ATCGCCCCACTTGATTTGG
```

Cycling Condition:

| 95 C. | 5 min  |     |
|-------|--------|-----|
| 95 C. | 10 sec |     |
| 60 C. | 30 sec | 40x |
| 95 C. | 15 sec |     |
| 60 C. | 1 min  |     |

All samples were analyzed in duplicates and the mean and standard deviation were determined. Specificity of the amplification was determined by a melting curve ranging from 60-95° C. Normalization to GAPDH was performed using the standard ddCt method.

Figure 15:
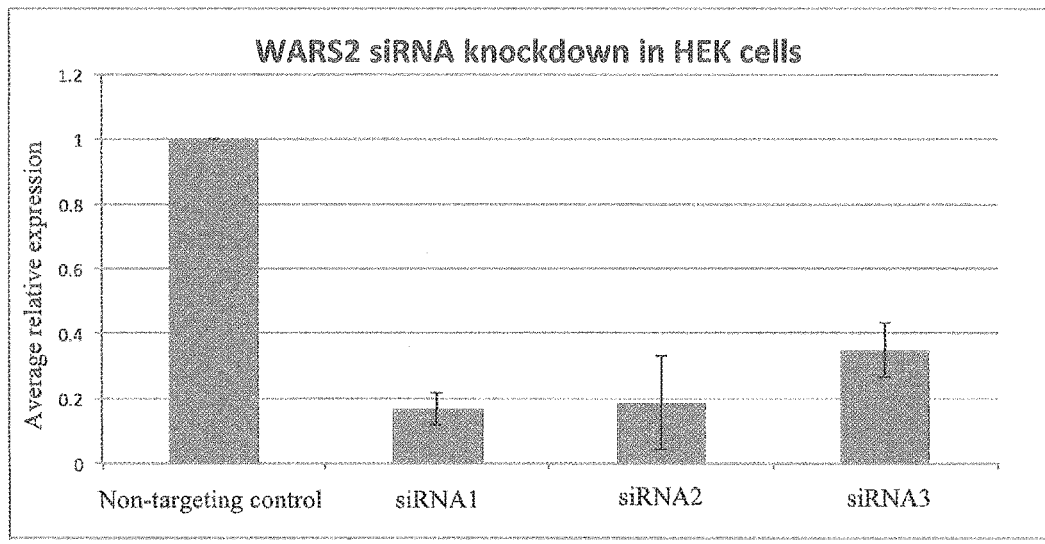
FIG. 15 is a bar graph showing the knockdown of expression of WARS2 mRNA in HEK293 cells in the presence of three different WARS2 siRNAs.

The experiment was repeated 5 times with the following results shown in Table 2 (and in FIG. 15).

TABLE 2

Results of siWARS2 knock down in HEK 293

| Experiment | 1 | 2 | 3 | 4 | 5 | Average | Standard deviation |
|------------|---|---|---|---|---|---------|--------------------|
| Non targeting control | 1 | 1 | 1 | 1 | 1 | 1 | 0 |
| siRNA 1 | 0.26 | 0.13 | 0.18 | 0.13 | 0.14 | 0.17 | 0.05 |
| siRNA 2 | 0.47 | 0.14 | 0.13 | 0.11 | 0.09 | 0.19 | 0.14 |
| siRNA 3 | 0.43 | 0.22 | 0.43 | 0.37 | 0.30 | 0.35 | 0.08 |

```
WARS2 siRNA1:
Sense:
                                              (SEQ ID NO: 50)
5'-GCAUUCAACCUACAGGAAU-3'

Antisense:
                                              (SEQ ID NO: 51)
5'-AUUCCUGUAGGUUGAAUGC-3'

WARS2 siRNA2:
Sense:
                                              (SEQ ID NO: 52)
5'-CCGACAUUCUGUUGUACAA-3'

Antisense:
                                              (SEQ ID NO: 53)
5'-UUGUACAACAGAAUGUCGG-3'

WARS2 siRNA3:
Sense:
                                              (SEQ ID NO: 54)
5'-GCUGGACAAGGACCAUUUA-3'

Antisense:
                                              (SEQ ID NO: 55)
5'-UAAAUGGUCCUUGUCCAGC-3'
```

These three siRNA sequence pairs target the regions of the WARS2 sequence below, respectively. In some aspects, the siRNA sequences comprise extra thymine (T) at the 3' end of both sense and antisense strands of a siRNA pair to increase siRNA resistance to nuclease activity inside the cells. In a particular aspect, the siRNA sense and antisense strands comprise two T's (TT) at the 3' end.

```
siRNA1 target
                                              (SEQ ID NO: 35)
GCATTCAACCTACAGGAAT siRNA2 target
                                              (SEQ ID NO: 36)
CCGACATTCTGTTGTACAA siRNA3 target
                                              (SEQ ID NO: 37)
GCTGGACAAGGACCATTTA
```

FIG. 14 sets out the cDNA of WARS2 indicating the positions targeted by the three siRNAs, as described above.

Example 5

WARS2 SNP that is Associated with Higher WARS2 Expression Controls WARS Levels in Human Plasma
WARS ELISA ELISA was used to determine WARS in human plasma and compare to the SNP genotype of WARS2 (rs984222). WARS levels in plasma were determined using an ELISA according to the manufacturer's instructions (ABIN366223; Antibodies-online GmbH, Aachen, Germany). Plasma was collected from healthy volunteers, aliquoted and stored at −70° C. 100 µl of undiluted plasma was usedper measurement. The standard curve was performed in duplicate and the detection limit was determined to be 0.078 ng/ml. ODs were read at 450 nm (with correction at 540 nm) on a microplate reader (uQuant; Biotek Instruments, UK).

WARS2 SNP Assay
SNP ID: rs984222 was used in the WARS2 SNP assay.
Assay: Life Technologies Assay ID: C_8699051_10
System used: Life Technologies Stepone plus rtPCR

TABLE 3

| PCR conditions: | | |
|---|---|---|
| Temp | Time | Cycles |
| 25° C. | 30 sec* | 1 |
| 95° C. | 10 min | 1 |
| 92° C. | 15 sec | 50 |
| 60° C. | 90 sec* |  |
| 72° C. | 30 sec |  |
| 25° C. | 30 sec* | 1 |

Fluorescence Sequence:

```
                                              (SEQ ID NO: 38)
TTCATATTCTGTCGAGACACCCATC[C/G]CCCTGTGTTTCACTTGTC
TGATTAC
```

VIC Dye C Nucleotide, FAM Dye G Nucleotide

The present study investigated the WARS2 SNP RS984222, which has a polymorphism of C/G transversion substitution. To investigate the ratio of this polymorphism in a cohort of Healthy Volunteers, a pre-made assay from Life Technologies was used (assay ID: C_8699051_10). This assay uses a VIC/FAM dye mixture to determine the SNP present. This assay was run on real time PCR, using the Life Technologies Stepone Plus, and analysed with Stepone Plus software v2.1, which created an allelic discrimination plot to determine SNPs.

Results

Figure 16:
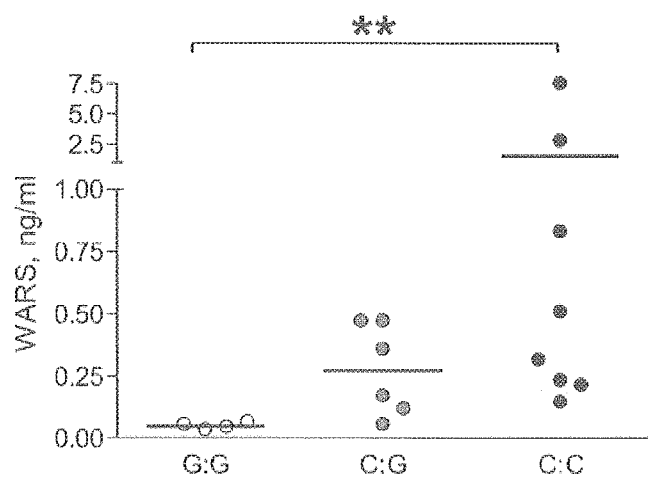
FIG. 16 is a graph showing that the WARS2 SNP that controls WARS2 expression also controls WARS levels in human plasma. **, $P<0.01$

The data show that the WARS2 SNP that controls WARS2 expression also controls WARS levels in human plasma. As shown herein, increased WARS2 expression reduced WARS secretion. Using a sandwich ELISA method (see the Methods section, above), it was determined whether the WARS2 SNP rs984222 that is associated with higher levels of WARS2 expression in multiple tissues (including fat) was associated with reduced circulating levels of WARS in human plasma. This revealed an effect of the SNP on WARS in human plasma. Individuals homozygous for the G:G allele (high WARS2 in tissues) had lower levels of WARS in human plasma as compared to the G:C allele (intermediate WARS2 expression in tissues) and as compared to the C:C allele (low WARS2 expression in tissues). See FIG. 16.

Example 6

WARS2 Expression Regulates WARS Secretion in Exosomes

Methods

Cell Culture and Immunocytochemistry

Human umbilical vein endothelial cells (HUVECs; Lonza) were cultured using EBM-2 medium (Lonza). After two passages, cells were digested with TrypLETM (Life Tech) and seeded into 8-well chamber slides (ibidi) at a density of 5,000 cells/cm$^2$. At 50% confluence, adenovirus (PRECISION TECHNOLOGIES) expressing human WARS2 or GFP was added at a multiplicity of infection of 100 (48 h). Low serum EBM-2 medium was applied and selected cells stimulated with interferon-gamma (500 unit/ml, 48 h). Cells were fixed with 4% Formaldehyde for 15 minutes and washed three times with PBS. Cells were treated with 0.1% Triton-100 (10 minutes) and washed three times with PBS. 1% BSA in PBS was applied for blocking (30 minutes). Primary antibody (WARS, Abcam, 1:200 in 1% BSA) was applied and cells incubated at 4° C. overnight. Cells were then washed in PBS (×3) and incubated (30 minutes) with secondary antibody (Alex Fluor conjugated, Life Tech, 1:1000). After washing with PBS (3×), cells were incubated for 30 minutes with Phalloidin (Alex Fluor conjugated, Life Tech, 1 to 200). Cells were then washed with PBS (×3), incubated with DAPI (Life Tech, 1 to 1000, 5 minutes) and mounted with ProLong® Gold Antifade (Life Tech). Images were acquired using a laser scanning microscope (LSM 710, Zeiss) using the same settings.

Results

Confocal images show that WARS was secreted in exosomes. Further, expression of WARS2 inhibited the secretion of these exosomes by trapping WARS in the cells (refer to FIG. 17). HUVEC cells were infected with control virus (shown in FIG. 17, left panel) or virus expressing WARS2 (shown in FIG. 17, right panel), stimulated with interferon gamma and then stained for WARS, actin, and the nucleus. In control cells, membrane bound exosomes/micro-vesicles containing WARS were seen budding from the cell's plasma membrane (arrows). In contrast, large amounts of WARS accumulated at the plasma membrane (*), but not in exosomes, in the WARS2-infected cells.

Example 7

Zinc Finger Nuclease Disruption of WARS2 Leads to Reduced Blood Vessel Density

Methods

Disruption of Wars2 in the Rat

The BN rat Wars2 locus was targeted in the terminal region of the first exon with zinc finger nucleases (ZFN) against the ZFN Target site:

```
                                        (SEQ ID NO: 39)
ACCCACAGCTACTGCggctcCCCAGGTAACCCGAG
```

(Sage laboratories, PA, USA). Gene disruption was screened by sequencing and an 8 bp deletion identified in exon 1 at the ZFN target site. This resulted in a frame shift after amino acid 27 of Wars2 protein and a premature stop in exon 2 after amino acid 53 of Wars2.

Genotyping of Mutant Strains

Genomic DNA was extracted from toe clip samples using E.Z.N.A Tissue DNA kit (OMEGA bio-tek) according to manufacturer's protocol. Following purification, PCR was performed on each sample consisting of JumpStart Taq ReadyMix (Sigma) and 1 µM of the following primers:

```
(i)
                                        (SEQ ID NO: 40)
5'-GTGAGTGCTGGCGCTTCATC
and (ii)
                                        (SEQ ID NO: 41)
5'-GGCCTAAAGCAGAAGGTCGG.
```

PCR cycling conditions: (i) 95° C. for 5 min; (ii) 95° C. for 30 s; (iii) 65° C. for 30 s; (iv) 72° C. for 30 s; (v) repeat cycles 2 to 4 for 30 times; (vi) 72° C. for 5 min; (vii) 4° C. hold. PCR products were run on a 5% agarose gel. Expected band sizes were (i) wild type=92 bp (ii) heterozygous deletion=92 bp and 84 bp (ii) homozygous deletion=84 bp.

Results

Figure 18:
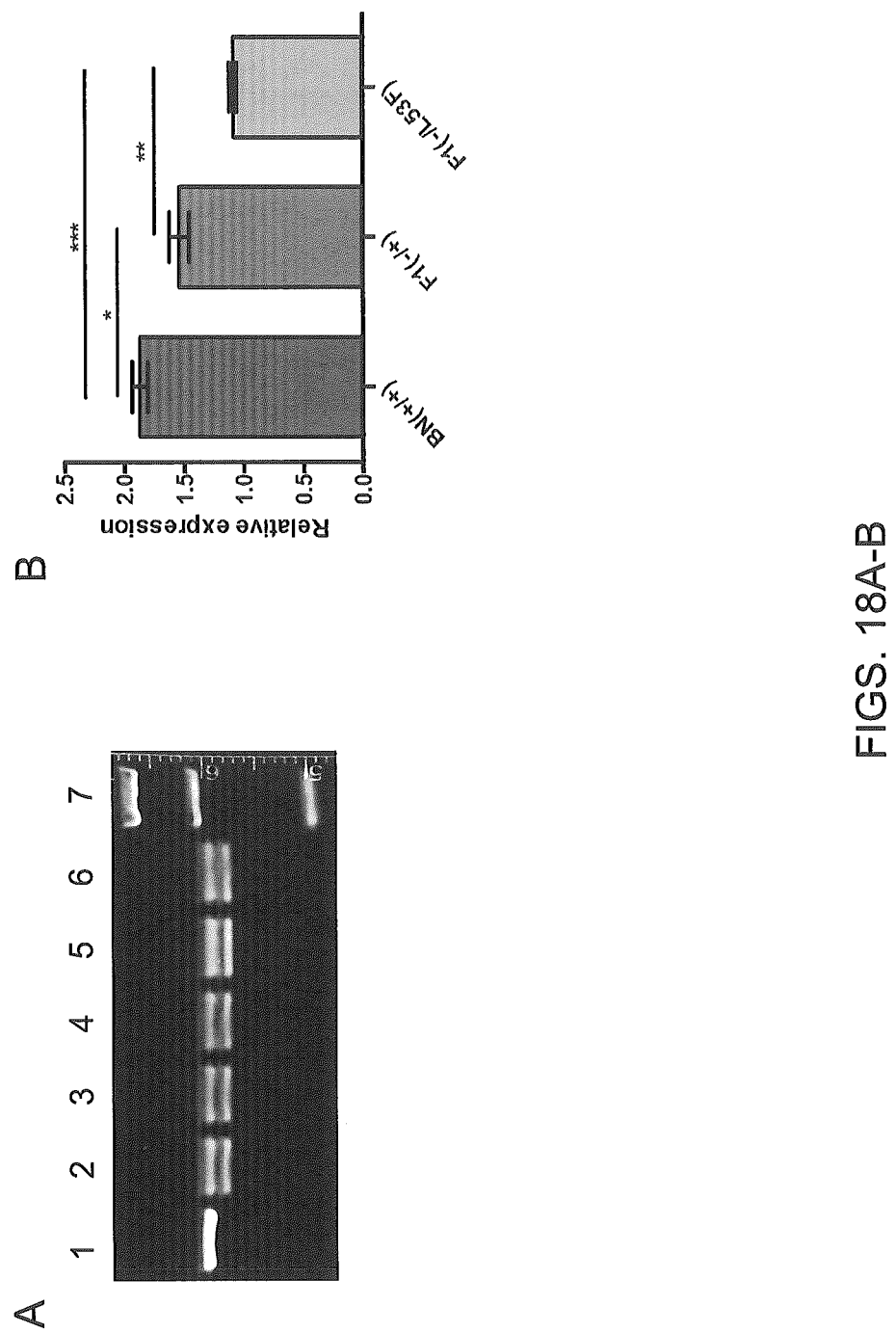
FIGS. 18A and 18B show effective targeting of Wars2 in the Brown Norway (BN) rat using zinc finger nuclease.
Figure 19:
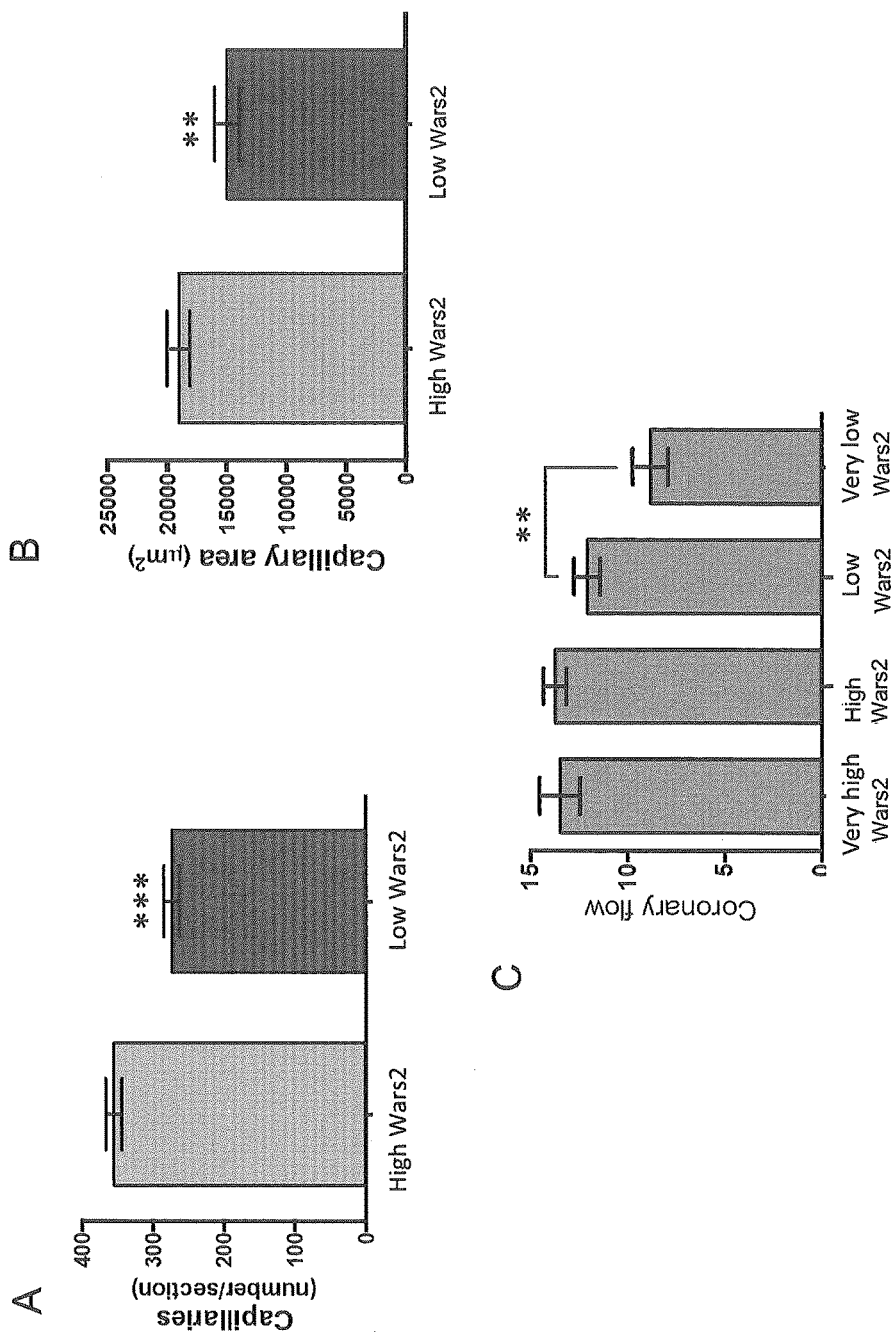
FIGS. 19A-C are in vivo data in the rat showing zinc finger nuclease mediated effects on blood vessel density by targeting rat Wars2 using nuclease technology.

These rat in vivo results show that Wars2 levels influenced capillary blood vessel density and coronary flow. Specifically, when Wars2 level was low, capillary blood vessel density was low. In addition, capillary area in the heart was also low when Wars2 was low. Similarly, coronary blood flow in the heart, which is dependent on capillary density, was low when Wars2 level was low. FIGS. 19A-C illustrate these results. FIG. 18 shows that Wars2 was effectively disrupted using zinc finger nuclease.

Example 8

WARS2 Activity Inhibition

Methods

WARS and WARS2 AMP-Glo Enzyme Assay

The WARS and WARS2 enzyme assay was performed using an ATP depletion assay based on a chemilumines optimized with the AMP-Glo™ reagent (Promega) using 96-well format assay. Reaction buffer contained 25 mM Tris-HCL pH7.2, 10 mM MgCl2, 50 mM KCl, 2.5 mM dithiothreitol, 0.1 mg/mL bovine serum albumin, 0.2 mM spermine, 10 U/mL pyrophosphatase and enzyme concentration used was 200 nM. Substrate concentrations were as follows: L-tryptophan 100 µM, bulk *E. coli* tRNA (Sigma) 200 µg/mL and ATP 100 µM. Reaction was carried out at 37° C. for one hour, followed by adding reagent I (AMP-glo kit).

The plate was incubated at room temperature for another hour. At the end of the hour the AMP detection solution was added to all the samples and incubated for one hour at room temperature. Data was collected by measuring the luminescence with the Infinite M200 microplate Reader (Tecan). Indolmycin was added at 10 micromolar concentration where indicated.

Results

Figure 20:
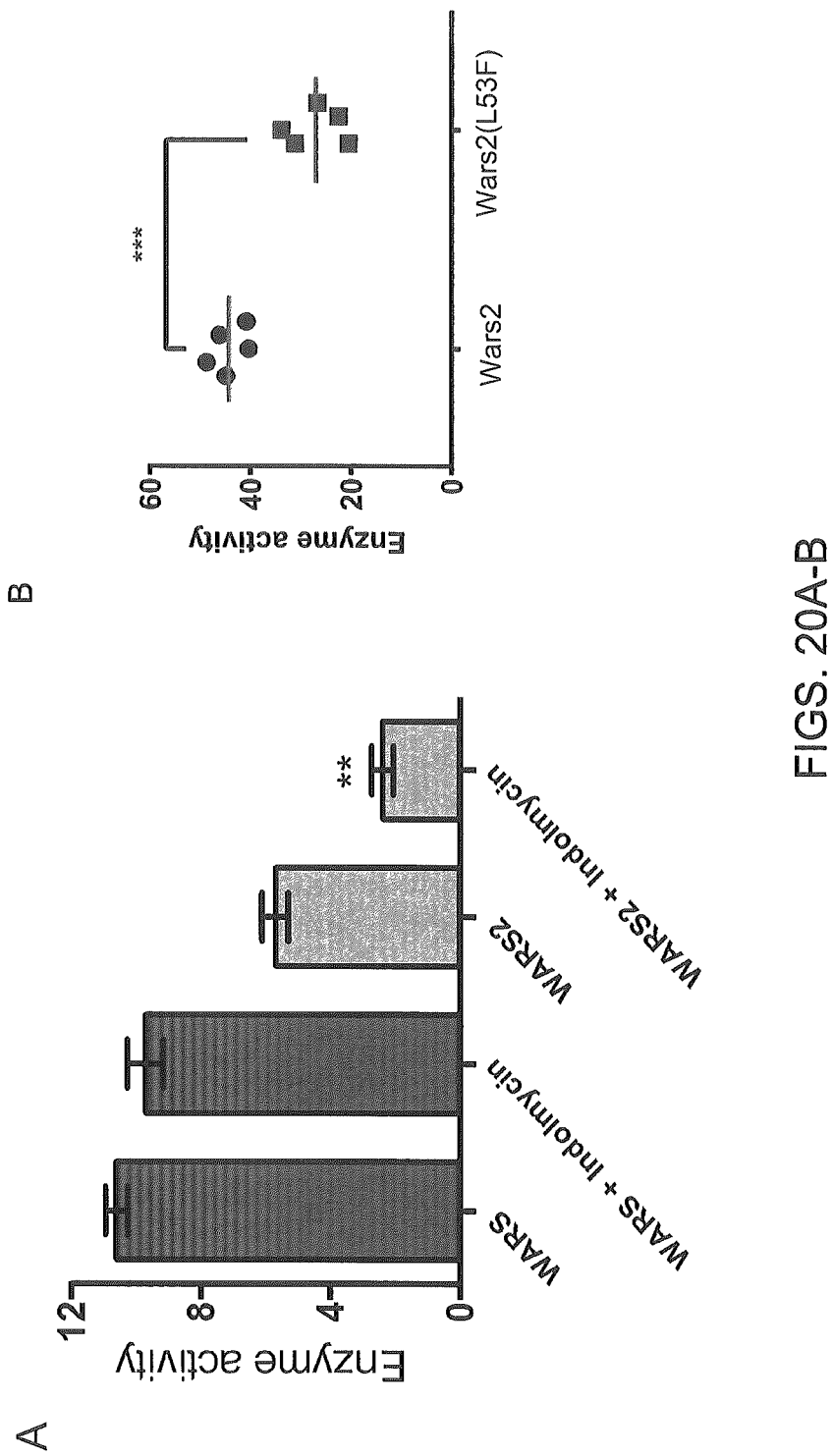
FIGS. 20A and 20B illustrate other modes of WARS2 activity inhibition.

Suitable chemical compounds may be used to inhibit WARS2 activity. For example, the present study shows that indolmycin inhibited human mitochondrial WARS2 but not human cytosolic WARS activity. Such inhibition of WARS2 activity may be combined with other modes of inhibition. For example, the WARS2 mutant rat mutation (L53F) is associated with lower blood vessel growth and lower WARS2 enzyme activity. Hence, using, e.g., gene therapy methods, the WARS2 mutant form L53F may be introduced into a subject to lower enzyme activity to inhibit blood vessel growth. Such targeted gene therapy methods may be further combined with other WARS2 inhibitors, e.g., indolmycin or related compound, to inhibit blood vessel growth. FIGS. 20A and 20B illustrate these results.

Example 9

In Vivo Knock Down of WARS2 in Rat Eye Using Cholesterol Modified siRNA

Methods

Both non-targeting (NT) siRNA and siWars2 were purchased from Dharmacon and formulated in the sterile siRNA buffer provided. Fifty (50) µg of siWars2 was injected intravitreously into one eye of each of three F344 rats in a total volume of 5 µl. The same dose of the NT control siRNA was injected into the contralateral eye of each animal. Retina and choroid were collected after 48 hours, and total RNA was extracted by Trizol (Ambion). cDNA was then synthesized according to the manufacturer's protocol (BioRad).

Real time PCR reactions to measure Wars2 expression were performed with the SYBRgreen mastermix (Qiagen) and normalized to GAPDH mRNA level by using the following primers:

```
Wars2 forward:
                                     (SEQ ID NO: 42)
5'-TTTCCAGCAGTCTCAGGTGTC-3';

Wars2 reverse:
                                     (SEQ ID NO: 43)
5' TACAGGGTATGTGAGCAGGC-3';

GAPDH forward:
                                     (SEQ ID NO: 44)
5'-AAAGGGTCATCATCTCCGCC-3';

GAPDH reverse:
                                     (SEQ ID NO: 45)
5'-CCTTCCACGATGCCAAAGTT-3'.
```

Results

Figure 21:
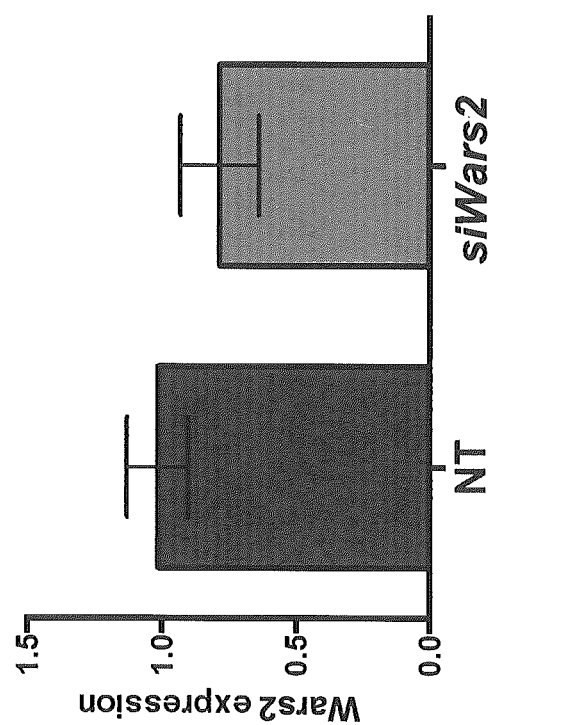
FIG. 21 shows in vivo knockdown of Wars2 in the eye using cholesterol modified siRNA. "NT" denotes non-targeting siRNA. Data are the mean of the results from three rats. **, $P<0.01$.

Wars2 was effectively knocked down in vivo in the rat eye using cholesterol modified siRNA. As compared to non-targeted siRNA, Wars2 targeting siRNA showed greater inhibition of Wars2 expression. See FIG. 21.

```
NT-siRNA:
Sense:
                                     (SEQ ID NO: 46)
5'-UGGUUUACAUGUCGACUUU-3'
```

```
Antisense:
                                     (SEQ ID NO: 47)
5'-AGUCGACAUGUAAACCAUU-3'

Wars2 siRNA:
Sense:
                                     (SEQ ID NO: 48)
5'-GCUCCAAUCAGAAGUGAUU-3'

Antisense:
                                     (SEQ ID NO: 49)
5'-UCACUUCUGAUUGGAGCUU-3'
```

Example 10

In Vitro Model of Angiogenesis

Methods

Tube Formation Assay

After 48 hours siRNA transfection or 48 hours adenovirus transduction or siRNA gene knockdown, HUVECs were harvested and seeded in 96-well plates, pre-coated with 50 µl matrigel (Corning Matrigel matrix, growth factor reduced) per well, at the density of 8,000 cells per well. After culturing in full EGM-2 medium for 8 hours, images were acquired for each well (at central position) at 5× objective (DM3000 inverted microscope, Leica). Images were analysed by WimTube (Wimasis Image Analysis).

Results

Modulation of WARS2 led to an increase and/or decrease in the formation of blood vessels (i.e., angiogenesis). The loss of WARS2 function led to very significant reduction in angiogenesis, as measured by the formation of tubes of endothelial cells; the total tube length; and the numbers of branching points. The data can be seen in FIGS. 22A-C. By comparison, the gain of WARS2 function—shown in FIGS. 22D-F—led to a corresponding increase in these measures of angiogenesis.

Example 11 siWARS2 Causes Decreased Endothelial Cell Proliferation

Methods

HUVECs cultured in 8 well chamber slides were fixed with 4% formaldehyde. Cells were permeabilized with 0.1% Triton x-100 and incubated with Alexa Fluor 488 phalloidin (Molecular Probes, 1 to 200 in PBS, 30 minutes). Cell nuclei were stained with DAPI (Molecular Probes, 1 to 1000 in PBS, 5 minutes) and cells mounted with ProLong gold antifade mountant (Molecular Probes) or VECTASHIELD mounting medium (Vector Laboratories). Images were acquired using a confocal laser scanning microscope (LSM 710, Zeiss) and super-resolution structured illumination microscope (ELYRA PS.1, Zeiss). Super-resolution images were post-processed by ZEN software (Zeiss) with SIM module according to manufacturer's instruction.

Cell counts: Adherent HUVECs were harvested by trypsinization and counted using an automated cell counter (Countess Automated Cell Counter; Invitrogen).

Results

Figure 23A:
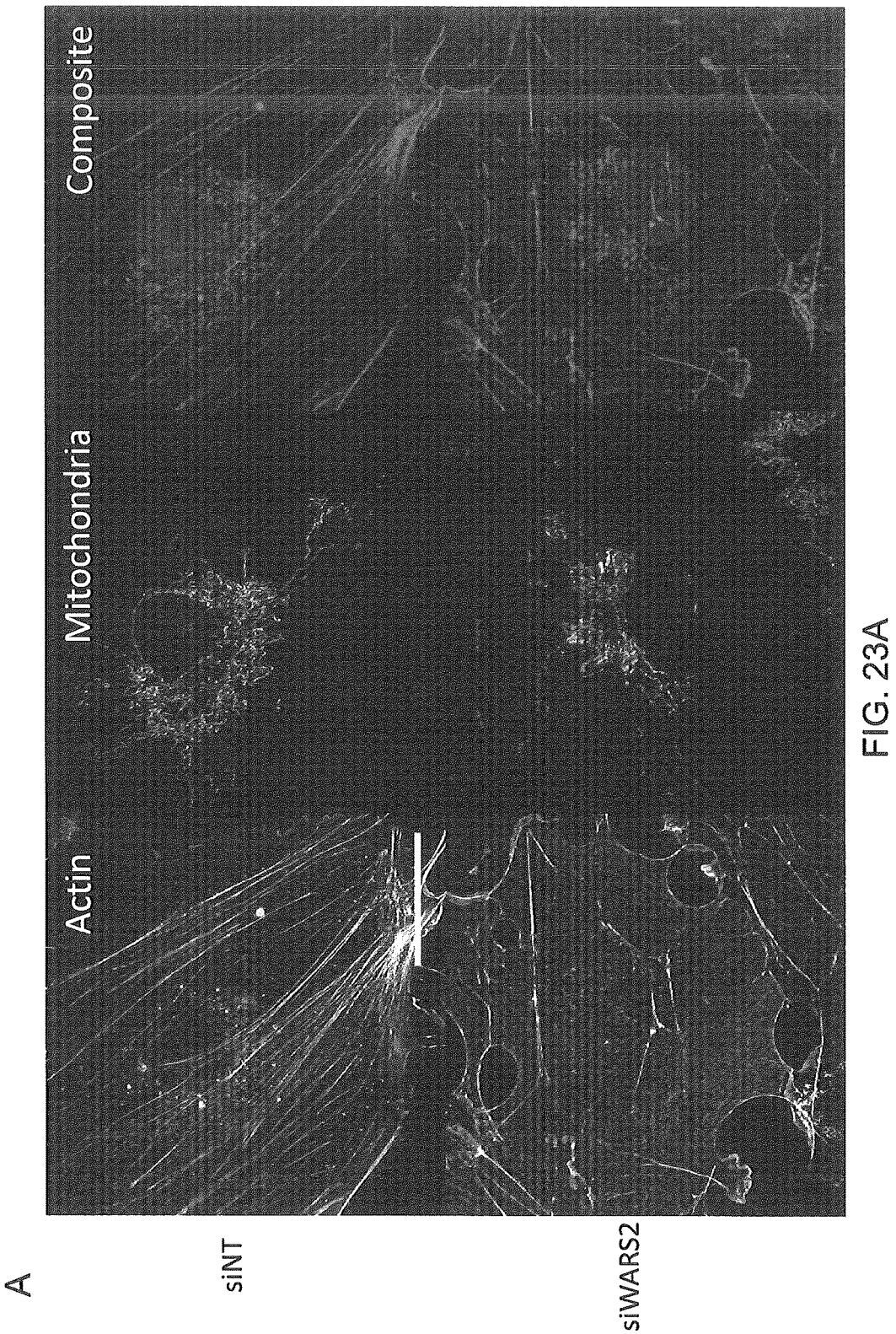
FIGS. 23A and 23B show the effects of WARS2 inhibition on EC morphology and cell number.
Figure 23B:
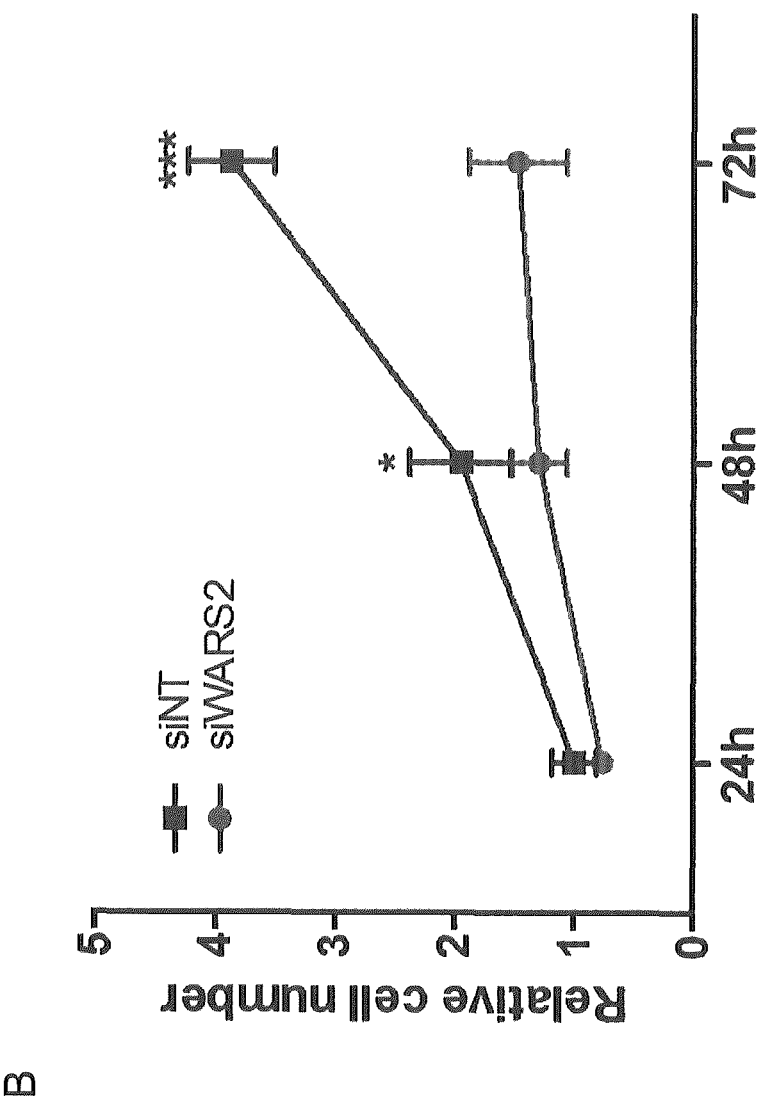
Figure 24A:
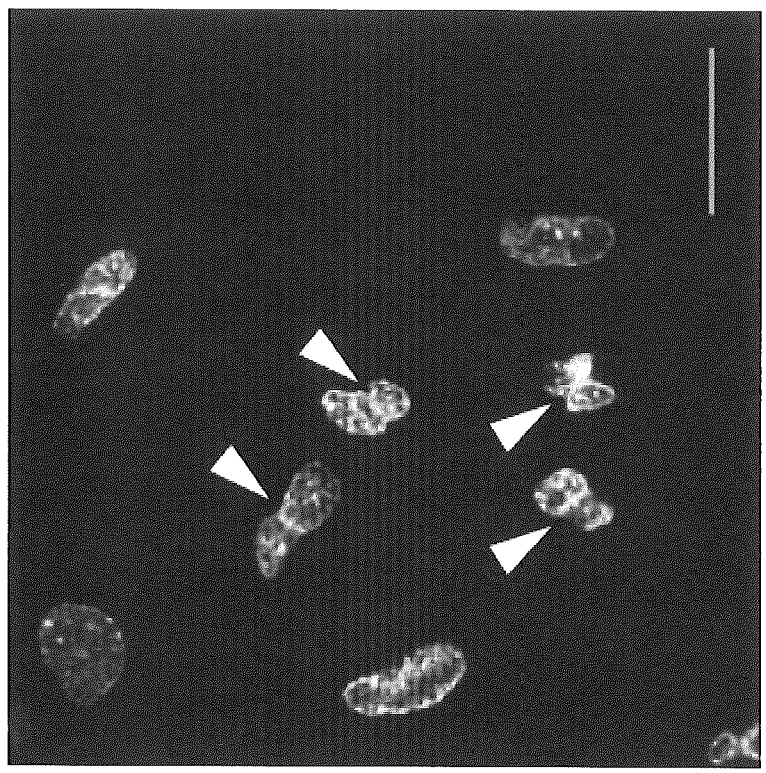
FIGS. 24A and 24B illustrate effects of WARS2 inhibition on the cell cycle.
Figure 24B:
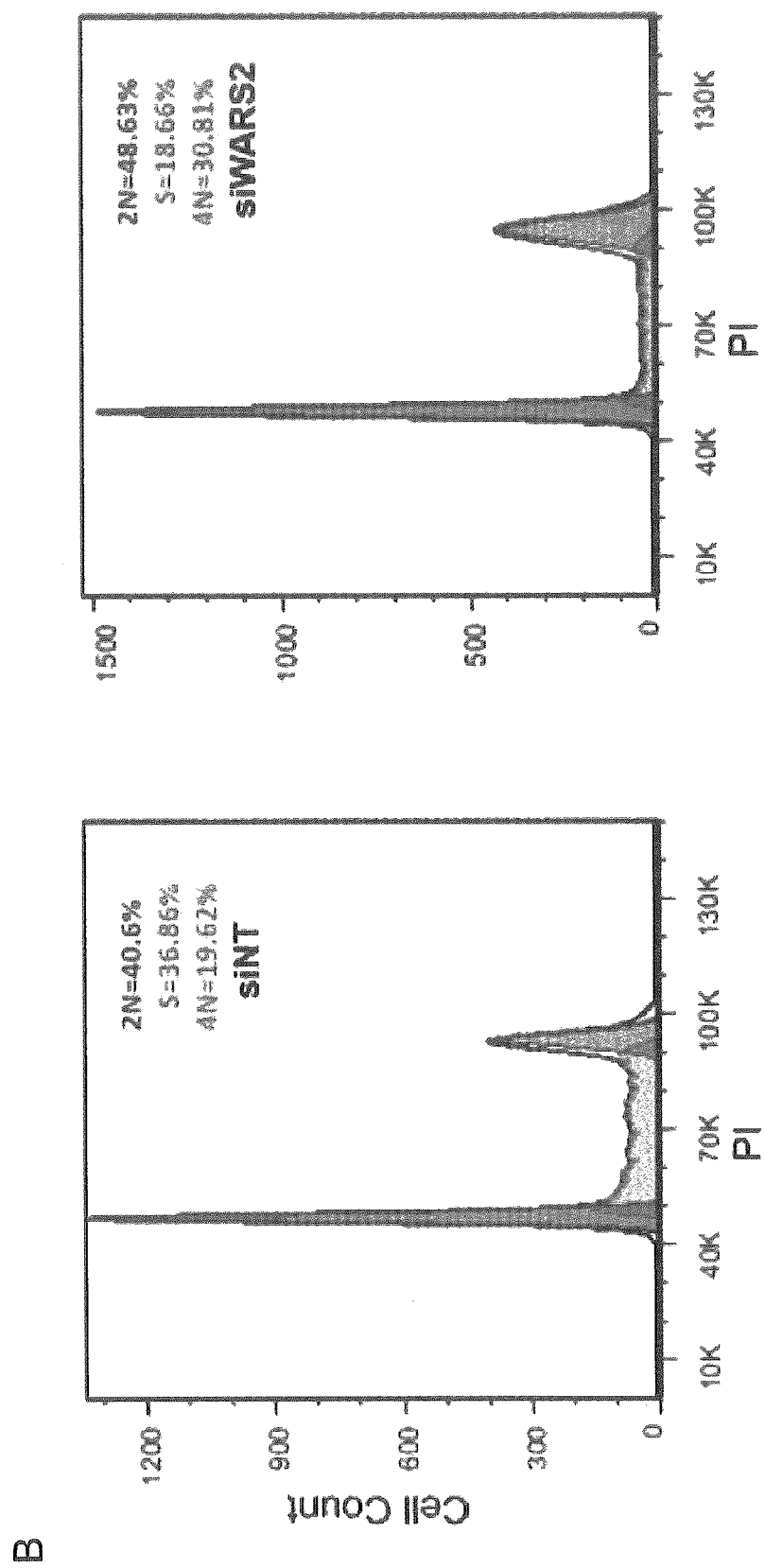

The effects on cell morphology can be seen in the high resolution micrograph in FIG. 23A. The actin fibres disappeared altogether in the presence of inhibited WARS2 and the mitochondria formed clumps. This reduced the ability of endothelial cells to migrate and divide; there was incomplete separation of nuclei and cells accumulate in G2/M phase (refer to FIGS. 24A and B). The downstream effect of these changes was reduced proliferation due to cell death. The significantly inhibited proliferative capacity can be seen in the graph shown in FIG. 23B.

Example 12

Wars2 Inhibition Prevents Blood Vessel Growth in an In Vivo Breast Cancer Angiogenesis Model Methods Matrigel Plug Angiogenesis Assay Corning Matrigel Membrane Matrix (LDEV-Free: 5 ml) (Fisher, cat# CB-40234A) was thawed on ice or in a 4° C. refrigerator. While keeping matrigel on ice, reconstituted stock (0.5 mg/ml in sterile PBS) of Recombinant Rat VEGF 164 (R&D Systems, cat#564-RV-010/CF) was added to a final concentration of 500 ng/ml in matrigel. 500 µl of cold VEGF/matrigel was loaded into chilled 1 ml syringes and capped with a 23- or 27-gauge needle (with caps on). Syringes were kept on ice to keep cold until injection.

Rats were anesthetized using isoflurane or ketamine cocktail. The mammary fat pad (MFP) between the lowest and second lowest nipple was pinched, lifted up slightly, and 500 µl of matrigel was injected into the MFP. The matrigel immediately solidified. At 5 days post-injection, rats were euthanized and the matrigel plug was carefully excised from the adipose tissue. The tissue was wrapped in foil and immediately frozen in liquid nitrogen.

Results

Figure 25:
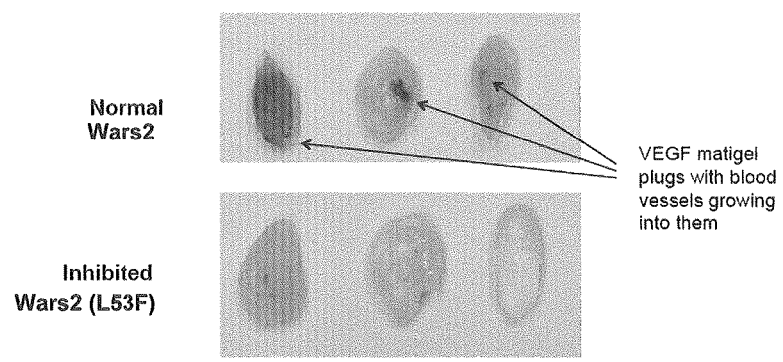
FIG. 25 illustrates that inhibition of Wars2 prevents blood vessel growth in a breast cancer angiogenesis model. Arrows indicate areas of blood vessel growth into Vascular Endothelial Growth Factor (VEGF) matrigel plugs from animals expressing normal Wars2. By contrast, virtually no growth into plugs from animals harboring the Wars2(L53F) mutation can be seen.

Blood vessel growth was prevented in vivo, in a breast cancer angiogenesis model, in the presence of inhibited Wars2. Three rats with normal Wars2 and three rats harboring the Wars2(L53F) mutation (mutated using zinc finger nuclease, as described herein—see also FIG. 18) were studied. In rats which have and express normal Wars2, blood vessel growth into VEGF matrigel plugs was visualized in each of the three rats examined. In contrast, in the three rats whose Wars2 had been inhibited by mutation using zinc finger nuclease, virtually no blood vessel growth into the VEGF matrigel plugs was seen. Matrigel plugs with and without regrowth can be seen in FIG. 25. Thus, WARS2 inhibition benefits disorders characterized by enhanced and/or undesirable blood vessel growth (such as, for example, cancer and various eye diseases).

Example 13

Evaluation of Wars2 siRNA on Reduction of Lesion Size and Leakage in a Rat Model of LASER-induced Choroidal Neovascularization (CNV)

Methods

Non-targeting siRNA (negative control), Wars2 siRNA (test agent), and anti-VEGF Ab (positive control) were administered intravitreously into the eyes of Brown Norway female rats aged 6-8 weeks, according to the following design:

Day 1: Bilateral Laser treatment to produce three (3) lesions per eye

Day 3: Bilateral intravitreal injection of negative control, positive control, or test agent Day 22: In-vivo fluorescein angiography Day 22: Enucleation of eyes and fixation for future histological analyses Three (3) groups of five (5) rats were used, as set out in Table 4.

TABLE 4

LASER-induced CNV experimental detail

| Group | Induction | Treatment | Treatment Details | Assessment |
|---|---|---|---|---|
| 1 | Laser CNV 3 lesions/eye, bilateral | Non targeting siRNA (negative control) (100 µg/eye) n = 5 | Bilateral Intravitreal injection on Day 3 | In-vivo fluorescein angiography on Day 22; Eyes enucleated on Day 22 and fixed in 4% PFA |
| 2 | Laser CNV 3 lesions/eye, bilateral | Anti-VEGF Ab (5 µg/eye) n = 5 | Bilateral Intravitreal injection on Day 3 | In-vivo fluorescein angiography on Day 22; Eyes enucleated on Day 22 and fixed in 4% PFA |
| 3 | Laser CNV 3 lesions/eye, bilateral | WARS2 siRNA (100 µg/eye) n = 5 | Bilateral Intravitreal injection on Day 3 | In-vivo fluorescein angiography on Day 22; Eyes enucleated on Day 22 and fixed in 4% PFA |

All animals were housed in groups of three in large cages kept in ventilated shelves under standard animal care conditions.

Anesthesia

Ketamine and Xylazine were mixed using a U-100 syringe utilizing 20 units of Ketamine (100 mg/ml) and 100 unite of Xylazine (20 mg/ml). The anesthesia mixture was applied via IP injection at 1 µl/g (body weight).

LASER Application to Produce CNV Lesions

Animals were dilated with 1% Cyclogyl solution and protected from light. Following observable dilation, the animals were sedated with ketamine/xylazine. The fundus of sedated animals was observed and recorded using a Micron III small animal funduscope (Phoenix Research). Laser treatments were performed using a thermal laser which was connected through the Micron III custom laser attachment. A total of 3 lesions are placed per eye, using a wavelength of 520 nm. The resultant fundus images were recorded and evaluated to confirm that the laser had successfully produced a bubble through the Bruch's membrane.

Intravitreal Administration

Animals were anesthetized with ketamine/xylazine and pupils dilated with topical administration of Cyclogel and/or Tropicamide. Following sedation and dilation, a total volume of 5 µl per eye was injected into the vitreous at the pars plana using a Hamilton syringe and a 33 gauge needle.

NT-siRNA:
Sense:
(SEQ ID NO: 46)
5'-UGGUUUACAUGUCGACUUU-3'

Antisense:
(SEQ ID NO: 47)
5'-AGUCGACAUGUAAACCAUU-3'

Wars2 siRNA:
Sense:
(SEQ ID NO: 48)
5'-GCUCCAAUCAGAAGUGAUU-3'

Antisense:
(SEQ ID NO: 49)
5'-UCACUUCUGAUUGGAGCUU-3'

Fluorescein Angiography

Animals were anesthetized with ketamine/xylazine and then received an IP injection of 10% fluorescein sodium at 1 µl/gram of body weight. Fundus images were then captured as 8-bit TIFF files using the Micron III and exciter/barrier filters for a target wavelength of 488 nm. Standard colour fundus photos were also captured for each eye.

Imaging and Lesion Quantification

All TIFF images were quantified using computerized image-analysis software (ImageJ, NIH, USA). Lesions were then individually traced free-hand in order to quantify the area in pixels and the colour fundus photos were used as a reference for lesion location. Areas of avascularization in the center of lesions are excluded from area calculations. If there was hemorrhage or two lesions overlapping, these lesions were excluded from analysis.

Tissue Collection

Animals were anesthetized with ketamine/xylazine (80/10 mg/kg) and then euthanized by IP administration of Euthasol (pentobarbital) at 200 mg/kg. Following euthanization, the eyes were enucleated and individually fixed in 4% paraformaldehyde. Following fixation, all eyes were stored in individual 2 mL screw cap polypropylene tubes. Samples were stored at room temperature.

Data and Statistical Analyses

Statistical analyses were performed with Graphpad Prism software (version 4.0) using an unpaired t-test for significance. Only changes with a p-value <0.05 are deemed statistically significant.

Example 14

Results of Experiment Performed in Example 13

In negative control animals (that is, those injected with the non-targeting siRNA) following laser treatment, choroidal neovascularization proceeds as would be expected. In the case of the therapeutic intervention control (anti-VEGF antibody) and the test agent (WARS2 siRNA), however, significant reduction in the extent of neovascularization is observed.

Example 15

Effect of WARS2 Knock Down on Human A549 Lung Cancer Cell Numbers

Methods

One day before transfection, the A549 lung carcinoma cell line (ATCC Catalog: CCL-185) was cultured in 96-well plates at $10^4$ cells/well. The following day the cells were transfected with a non-targeting siRNA control (SN001-10D, 10 nmol, from Singapore Advanced Biologics Pte Ltd) or the human WARS2 siRNA (5'-CCGACATTCTGTTGTA-CAA-3'—SEQ ID NO:36). Transfection was carried out as described by Life Technologies protocol for its Lipofectamine RNAiMAX procedure.

Cell numbers were analyzed 2, 4 and 5 days post-transfection, using the CellTiter-Glo® Luminescent Cell Viability Assay (Promega).

Results

Figure 26:
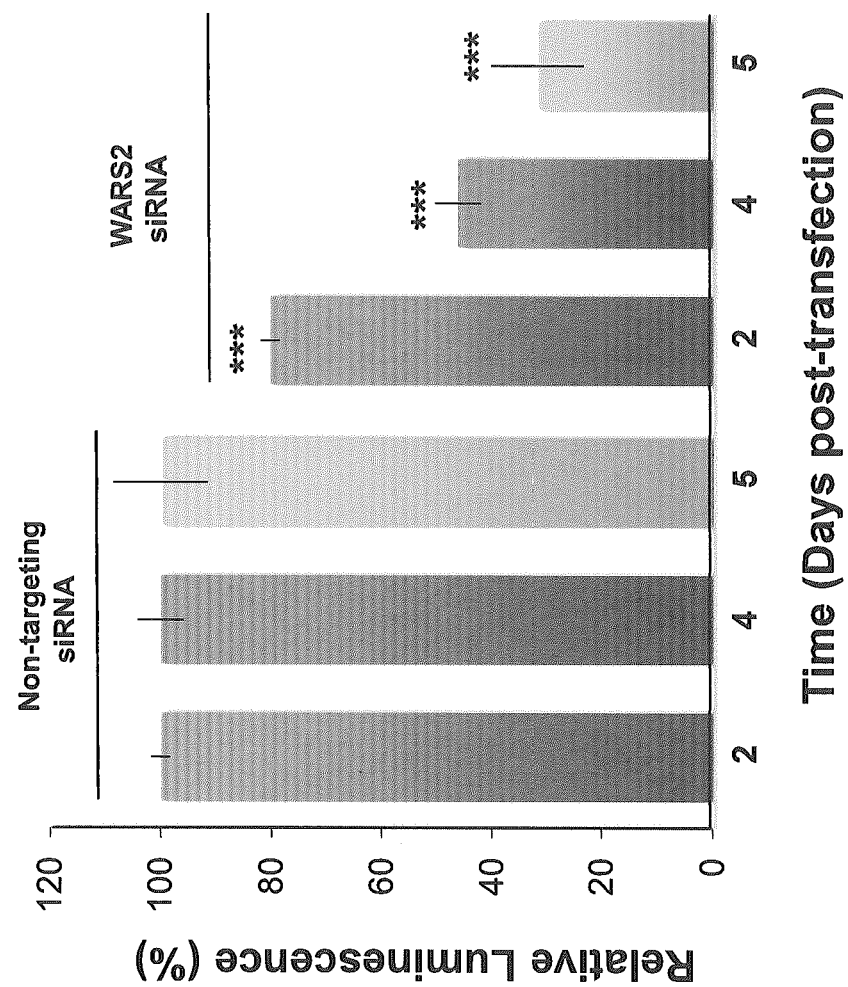
FIG. 26 shows proliferation of cells of the A549 lung carcinoma cell line can be reduced by decreasing expression of WARS2. Data are mean of three experiments; standard deviation bars are shown. "***" indicates significant at $P<0.005$.

The present study demonstrates that decreasing WARS2 expression using siRNA targeted to WARS2 significantly reduced the number of lung cancer cells in human A549 lung carcinoma. As FIG. 26 shows, non-targeting siRNA had no effect, whereas a significant reduction in cell numbers was observed by as little as two days after transfection of the siRNA and, by five days post-transfection, numbers were reduced by 70%. Accordingly, the proliferation of cancer cells was be reduced or inhibited by decreasing the expression of WARS2.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of modulating angiogenesis in an individual in need thereof comprising administering an effective amount of an agent that modulates expression of WARS2, activity of WARS2 or a combination thereof; wherein the agent is any one or more of a nucleic acid that binds to and specifically targets WARS2 nucleic acid; a mutant WARS2 that modulates WARS2 binding to WARS; a restriction enzyme that specifically targets WARS2 expression or activity or both; a small organic molecule or a derivative thereof that directly or indirectly influences WARS2 expression or activity or both.

2. The method of claim 1 wherein the agent is a nucleic acid selected from a small interfering ribonucleic acid (siRNA) or a morpholino oligomer that specifically targets WARS2, or both, an aptamer or a combination thereof.

3. The method of claim 1 wherein the agent is a mutant WARS2 having a L53F substitution that modulates WARS2 binding to WARS.

4. The method of claim 1 wherein the agent is a small organic molecule selected from indolmycin or a derivative thereof.

5. The method of claim 1 wherein the agent enhances the expression of WARS2, the activity of WARS2 or a combination thereof, thereby enhancing angiogenesis.

6. The method of claim 1 wherein the nucleic acid is a vector that directs expression of WARS2.

7. The method of claim 1 wherein the agent inhibits angiogenesis caused by, or that occurs as a consequence of one or more conditions or diseases; the one or more conditions or diseases being retinopathy, macular degeneration, cancer, obesity, or a combination thereof.

8. The method of claim 7 wherein the retinopathy is diabetic retinopathy.

9. The method of claim 7 wherein the macular degeneration is age-related macular degeneration (AMD).

10. The method of claim 7, wherein the cancer cell is lung carcinoma cell.

11. The method of claim 1 wherein the activity of WARS2 is enhanced or downregulated.

12. The method of claim 1, wherein the agent is a restriction enzyme selected from a zinc finger nuclease, a CRISPR/Cas9 or a TALEN, that specifically targets WARS2.

* * * * *

SEQUENCE LISTING

<160> NUMBER OF SEQ ID NOS: 55

<210> SEQ ID NO 1
<211> LENGTH: 329
<212> TYPE: PRT
<213> ORGANISM: Rattus
<220> FEATURE:
<221> NAME/KEY: VARIANT
<222> LOCATION: 270
<223> OTHER INFORMATION: Xaa = A or R

<400> SEQUENCE: 1

Lys Glu Ser Gly Glu Arg Val Phe Ser Gly Ile Gln Pro Thr Gly Ile
 1               5                  10                  15

Pro His Leu Gly Asn Tyr Leu Gly Ala Ile Glu Ser Trp Val Lys Leu
            20                  25                  30

```
Gln Glu Glu Tyr Asp Thr Val Ile Tyr Ser Ile Val Asp Leu His Ser
         35                  40                  45

Ile Thr Val Pro Gln Asp Pro Gly Ile Leu Gln Ser Ile Leu Asp
 50                  55                  60

Met Thr Ala Val Leu Leu Ala Cys Gly Ile Asp Pro Glu Arg Ser Ile
 65                  70                  75                  80

Leu Phe Gln Gln Ser Gln Val Ser Glu His Thr Gln Leu Ser Trp Ile
                 85                  90                  95

Leu Thr Cys Met Val Arg Leu Pro Arg Leu Gln His Leu His Gln Trp
                100                 105                 110

Lys Ala Lys Ala Ala Arg Gln Lys His Asp Gly Thr Val Gly Leu Leu
                115                 120                 125

Thr Tyr Pro Val Leu Gln Ala Ala Asp Ile Leu Cys Tyr Lys Ser Thr
        130                 135                 140

His Val Pro Val Gly Glu Asp Gln Val Gln His Met Glu Leu Val Gln
145                 150                 155                 160

Asp Leu Ala Arg Ser Phe Asn Gln Lys Tyr Gly Glu Leu Phe Pro Leu
                165                 170                 175

Pro Arg Ser Ile Leu Thr Ser Met Lys Lys Val Lys Ser Leu Arg Asp
                180                 185                 190

Pro Ser Ala Lys Met Ser Lys Ser Asp Pro Asp Lys Leu Ala Thr Val
            195                 200                 205

Gln Ile Thr Asp Ser Pro Glu Glu Ile Val Arg Lys Phe Arg Lys Ala
        210                 215                 220

Val Thr Asp Phe Thr Ser Glu Val Thr Tyr Glu Pro Asp Ser Arg Pro
225                 230                 235                 240

Gly Val Ser Asn Met Val Ala Ile His Ala Ala Val Ser Gly Leu Ser
                245                 250                 255

Val Glu Glu Val Val Arg Asn Ser Ala Gly Val Asp Thr Xaa Tyr Lys
                260                 265                 270

Leu Leu Val Ala Asp Ala Val Ile Glu Lys Phe Ala Pro Ile Arg Ser
            275                 280                 285

Glu Ile Glu Lys Leu Lys Met Asp Lys Asp His Leu Arg Lys Val Leu
        290                 295                 300

Leu Val Gly Ser Ala Lys Ala Lys Glu Leu Ala Ser Pro Val Phe Glu
305                 310                 315                 320

Glu Val Lys Lys Leu Val Gly Ile Leu
                325

<210> SEQ ID NO 2
<211> LENGTH: 355
<212> TYPE: PRT
<213> ORGANISM: Mus musculus
<220> FEATURE:
<221> NAME/KEY: VARIANT
<222> LOCATION: 60
<223> OTHER INFORMATION: Xaa = V or N
<220> FEATURE:
<221> NAME/KEY: VARIANT
<222> LOCATION: 119
<223> OTHER INFORMATION: Xaa = H or T
<220> FEATURE:
<221> NAME/KEY: VARIANT
<222> LOCATION: 178
<223> OTHER INFORMATION: Xaa = E or D
<220> FEATURE:
<221> NAME/KEY: VARIANT
<222> LOCATION: 237
<223> OTHER INFORMATION: Xaa = I or T
<220> FEATURE:
```

```
<221> NAME/KEY: VARIANT
<222> LOCATION: 296
<223> OTHER INFORMATION: Xaa = A or R

<400> SEQUENCE: 2

Met Ala Leu Phe Ser Val Arg Lys Ala Arg Glu Cys Trp Arg Phe Ile
1               5                   10                  15

Arg Ala Leu His Lys Gly Pro Ala Ala Thr Leu Ala Pro Gln Lys Glu
            20                  25                  30

Ser Gly Glu Arg Val Phe Ser Gly Ile Gln Pro Thr Gly Ile Leu His
        35                  40                  45

Leu Gly Asn Tyr Leu Gly Ala Ile Glu Ser Trp Xaa Leu Gln Glu Glu
50                  55                  60

Tyr Asp Thr Val Ile Tyr Ser Ile Val Asp Leu His Ser Ile Thr Val
65                  70                  75                  80

Pro Gln Asp Pro Thr Val Leu Gln Gln Ser Ile Leu Asp Met Thr Ala
                85                  90                  95

Val Leu Leu Ala Cys Gly Ile Asn Pro Glu Lys Ser Ile Leu Phe Gln
            100                 105                 110

Gln Ser Lys Val Ser Glu Xaa Gln Leu Ser Trp Ile Leu Thr Cys Met
        115                 120                 125

Val Arg Leu Pro Arg Leu Gln His Leu His Gln Trp Lys Ala Lys Ala
130                 135                 140

Ala Lys Gln Lys His Asp Gly Thr Val Gly Leu Leu Thr Tyr Pro Val
145                 150                 155                 160

Leu Gln Ala Ala Asp Ile Leu Cys Tyr Lys Ser Thr His Val Pro Val
                165                 170                 175

Gly Xaa Gln Val Gln His Met Glu Leu Val Gln Asp Leu Ala Arg Ser
            180                 185                 190

Phe Asn Gln Lys Tyr Gly Glu Phe Phe Pro Leu Pro Lys Ser Ile Leu
        195                 200                 205

Thr Ser Met Lys Lys Val Lys Ser Leu Arg Asp Pro Ser Ser Lys Met
210                 215                 220

Ser Lys Ser Asp Pro Asp Lys Leu Ala Thr Val Arg Xaa Asp Ser Pro
225                 230                 235                 240

Glu Glu Ile Val Gln Lys Phe Arg Lys Ala Val Thr Asp Phe Thr Ser
                245                 250                 255

Glu Val Thr Tyr Glu Pro Asp Ser Arg Ala Gly Val Ser Asn Met Val
            260                 265                 270

Ala Ile His Ala Val Ser Gly Leu Ser Val Glu Glu Val Val Arg
        275                 280                 285

Ser Ser Ala Gly Leu Asp Thr Xaa Tyr Lys Leu Leu Val Ala Asp Ala
290                 295                 300

Val Ile Glu Lys Phe Ala Pro Ile Arg Lys Glu Ile Glu Lys Leu Lys
305                 310                 315                 320

Met Asp Lys Asp His Leu Arg Lys Val Leu Val Gly Ser Ala Lys
                325                 330                 335

Ala Lys Glu Leu Ala Ser Pro Val Phe Glu Glu Val Lys Lys Leu Val
            340                 345                 350

Gly Ile Leu
        355

<210> SEQ ID NO 3
<211> LENGTH: 355
<212> TYPE: PRT
```

```
<213> ORGANISM: Homo sapien
<220> FEATURE:
<221> NAME/KEY: VARIANT
<222> LOCATION: 60
<223> OTHER INFORMATION: Xaa = V or R
<220> FEATURE:
<221> NAME/KEY: VARIANT
<222> LOCATION: 119
<223> OTHER INFORMATION: Xaa = H or T
<220> FEATURE:
<221> NAME/KEY: VARIANT
<222> LOCATION: 178
<223> OTHER INFORMATION: Xaa = E or D
<220> FEATURE:
<221> NAME/KEY: VARIANT
<222> LOCATION: 237
<223> OTHER INFORMATION: Xaa = I or T
<220> FEATURE:
<221> NAME/KEY: VARIANT
<222> LOCATION: 296
<223> OTHER INFORMATION: Xaa = A or R

<400> SEQUENCE: 3

Met Ala Leu His Ser Met Arg Lys Ala Arg Glu Arg Trp Ser Phe Ile
 1               5                  10                  15

Arg Ala Leu His Lys Gly Ser Ala Ala Pro Ala Leu Gln Lys Asp
                20                  25                  30

Ser Lys Lys Arg Val Phe Ser Gly Ile Gln Pro Thr Gly Ile Leu His
            35                  40                  45

Leu Gly Asn Tyr Leu Gly Ala Ile Glu Ser Trp Xaa Leu Gln Asp Glu
        50                  55                  60

Tyr Asp Ser Val Leu Tyr Ser Ile Val Asp Leu His Ser Ile Thr Val
 65                  70                  75                  80

Pro Gln Asp Pro Ala Val Leu Arg Gln Ser Ile Leu Asp Met Thr Ala
                85                  90                  95

Val Leu Leu Ala Cys Gly Ile Asn Pro Glu Lys Ser Ile Leu Phe Gln
            100                 105                 110

Gln Ser Gln Val Ser Glu Xaa Gln Leu Ser Trp Ile Leu Ser Cys Met
        115                 120                 125

Val Arg Leu Pro Arg Leu Gln His Leu His Gln Trp Lys Ala Lys Thr
130                 135                 140

Thr Lys Gln Lys His Asp Gly Thr Val Gly Leu Leu Thr Tyr Pro Val
145                 150                 155                 160

Leu Gln Ala Ala Asp Ile Leu Leu Tyr Lys Ser Thr His Val Pro Val
                165                 170                 175

Gly Xaa Gln Val Gln His Met Glu Leu Val Gln Asp Leu Ala Gln Gly
            180                 185                 190

Phe Asn Lys Lys Tyr Gly Glu Phe Phe Pro Val Pro Glu Ser Ile Leu
        195                 200                 205

Thr Ser Met Lys Lys Val Lys Ser Leu Arg Asp Pro Ser Ala Lys Met
210                 215                 220

Ser Lys Ser Asp Pro Asp Lys Leu Ala Thr Val Arg Xaa Asp Ser Pro
225                 230                 235                 240

Glu Glu Ile Val Gln Lys Phe Arg Lys Ala Val Thr Asp Phe Thr Ser
                245                 250                 255

Glu Val Thr Tyr Asp Pro Ala Gly Arg Ala Gly Val Ser Asn Ile Val
            260                 265                 270

Ala Val His Ala Ala Val Thr Gly Leu Ser Val Glu Glu Val Val Arg
        275                 280                 285

Arg Ser Ala Gly Met Asn Thr Xaa Tyr Lys Leu Ala Val Ala Asp Ala
```

```
                290                 295                 300
Val Ile Glu Lys Phe Ala Pro Ile Lys Arg Glu Ile Glu Lys Leu Lys
305                 310                 315                 320

Leu Asp Lys Asp His Leu Glu Lys Val Leu Gln Ile Gly Ser Ala Lys
                325                 330                 335

Ala Lys Glu Leu Ala Tyr Thr Val Cys Gln Glu Val Lys Lys Leu Val
            340                 345                 350

Gly Phe Leu
        355

<210> SEQ ID NO 4
<211> LENGTH: 1080
<212> TYPE: DNA
<213> ORGANISM: Homo sapien

<400> SEQUENCE: 4
atggcgctgc actcaatgcg gaaagcgcgt gagcgctgga gcttcatccg ggcacttcat     60
aagggatccg cagctgctcc cgctctccag aaagacagca gaagcgagt attttccggc    120 attcaaccta caggaatcct ccacctgggc aattacctgg agccattga gctgggtg     180 aggttacagg atgaatatga ctctgtatta tacagcattg ttgacctcca ctccattact    240
gtcccccaag acccagctgt ccttcggcag agcatcctgg acatgactgc tgttcttctt    300
gcctgtggca taaaccccga aaaaagcatc cttttccaac aatctcaggt gtctgaacac    360
acacaattaa gttggatcct ttcctgcatg gtcagactac ctcgattaca acatttacat    420
cagtggaagg caaagactac caagcagaag acgatggca cggtgggcct gctcacatac    480
ccagtactcc aggcagccga cattctgttg tacaagtcca cacacgttcc tgttggggag    540
gatcaagtcc agcacatgga actagttcag gatctagcac aaggttttca acaagaagtat    600 ggggagttct ttccagtgcc cgagtccatt ctcacatcca tgaagaaggt aaaatcccta    660
cgtgatcctt ctgccaaaat gtcgaaatca gaccctgaca aactggccac cgtccgaata    720
acagacagcc cagaggagat agtgcagaaa ttccgcaagg ctgtgacaga cttcacctcg    780
gaggtcacct atgacccggc tggccgcgct ggcgtgtcca acatagtggc ggtgcatgcc    840
gcggtgacgg ggctctccgt ggaggaagtg gtgcgccgca gcgcgggcat gaacactgct    900
cgctacaagc tggccgtggc agatgctgtg attgagaagt ttgccccaat taagcgtgaa    960
attgaaaaac tgaagctgga caaggaccat ttagagaagg ttttacaaat tggatcagca   1020
aaagccaaag aattagcata cactgtgtgc caggaggtga agaaattggt gggttttcta   1080

<210> SEQ ID NO 5
<211> LENGTH: 43
<212> TYPE: PRT
<213> ORGANISM: Rattus

<400> SEQUENCE: 5

Glu Ser Gly Glu Arg Val Phe Ser Gly Ile Gln Pro Thr Gly Ile Pro
1               5                  10                  15

His Leu Gly Asn Tyr Phe Gly Ala Ile Glu Ser Trp Val Lys Leu Gln
            20                  25                  30

Glu Glu Tyr Asp Thr Val Ile Tyr Ser Ile Val
        35                  40

<210> SEQ ID NO 6
<211> LENGTH: 43
<212> TYPE: PRT
```

```
<213> ORGANISM: Rattus

<400> SEQUENCE: 6

Glu Ser Gly Glu Arg Val Phe Ser Gly Ile Gln Pro Thr Gly Ile Pro
1               5                   10                  15

His Leu Gly Asn Tyr Phe Gly Ala Ile Glu Ser Trp Val Lys Leu Gln
            20                  25                  30

Glu Glu Tyr Asp Thr Val Ile Tyr Ser Ile Val
        35                  40

<210> SEQ ID NO 7
<211> LENGTH: 43
<212> TYPE: PRT
<213> ORGANISM: Rattus

<400> SEQUENCE: 7

Glu Ser Gly Glu Arg Val Phe Ser Gly Ile Gln Pro Thr Gly Ile Pro
1               5                   10                  15

His Leu Gly Asn Tyr Phe Gly Ala Ile Glu Ser Trp Val Lys Leu Gln
            20                  25                  30

Glu Glu Tyr Asp Thr Val Ile Tyr Ser Ile Val
        35                  40

<210> SEQ ID NO 8
<211> LENGTH: 43
<212> TYPE: PRT
<213> ORGANISM: Rattus

<400> SEQUENCE: 8

Glu Ser Gly Glu Arg Val Phe Ser Gly Ile Gln Pro Thr Gly Ile Pro
1               5                   10                  15

His Leu Gly Asn Tyr Leu Gly Ala Ile Glu Ser Trp Val Lys Leu Gln
            20                  25                  30

Glu Glu Tyr Asp Thr Val Ile Tyr Ser Ile Val
        35                  40

<210> SEQ ID NO 9
<211> LENGTH: 43
<212> TYPE: PRT
<213> ORGANISM: Mus musculus

<400> SEQUENCE: 9

Asp Ser Lys Lys Arg Ile Phe Ser Gly Ile Gln Pro Thr Gly Ile Leu
1               5                   10                  15

His Leu Gly Asn Tyr Leu Gly Ala Ile Glu Asn Trp Val Arg Leu Gln
            20                  25                  30

Asp Glu Tyr Asp Ser Val Leu Tyr Ser Ile Val
        35                  40

<210> SEQ ID NO 10
<211> LENGTH: 43
<212> TYPE: PRT
<213> ORGANISM: Homo sapien

<400> SEQUENCE: 10

Asp Ser Lys Lys Arg Val Phe Ser Gly Ile Gln Pro Thr Gly Ile Leu
1               5                   10                  15

His Leu Gly Asn Tyr Leu Gly Ala Ile Glu Ser Trp Val Arg Leu Gln
            20                  25                  30

Asp Glu Tyr Asp Ser Val Leu Tyr Ser Ile Val
```

35                  40

<210> SEQ ID NO 11
<211> LENGTH: 43
<212> TYPE: PRT
<213> ORGANISM: Gallus gallus

<400> SEQUENCE: 11

Met Val Thr Asp Arg Ile Phe Ser Gly Ile Gln Pro Thr Gly Thr Pro
 1               5                  10                  15

His Leu Gly Asn Tyr Leu Gly Ala Ile Gln Asn Trp Val Asn Leu Gln
            20                  25                  30

Glu Lys Tyr Asn Ser Val Leu Tyr Ser Ile Met
        35                  40

<210> SEQ ID NO 12
<211> LENGTH: 47
<212> TYPE: PRT
<213> ORGANISM: Drosophila melanogaster

<400> SEQUENCE: 12

Glu His Asn Thr Arg Trp Pro Arg Lys Val Phe Ser Gly Ile Gln Pro
 1               5                  10                  15

Thr Gly Ser Leu His Leu Gly Asn Tyr Leu Gly Ala Val Arg Lys Trp
            20                  25                  30

Val Gln Leu Gln Asn Ala Arg Asp Asp Val Thr Val Cys Ile Val
        35                  40                  45

<210> SEQ ID NO 13
<211> LENGTH: 42
<212> TYPE: PRT
<213> ORGANISM: Danio rerio

<400> SEQUENCE: 13

Ser Lys Gly Leu Val Phe Ser Gly Ile Gln Pro Thr Gly Ile Pro His
 1               5                  10                  15

Leu Gly Asn Tyr Leu Gly Ala Leu Glu Ser Trp Val Ala Leu Gln Asp
            20                  25                  30

Asp Tyr Ser Thr Val Met Tyr Ser Ile Val
        35                  40

<210> SEQ ID NO 14
<211> LENGTH: 46
<212> TYPE: PRT
<213> ORGANISM: Saccharomyces cerevisiae

<400> SEQUENCE: 14

His Ser Asn Ala Thr Val Phe Ser Met Ile Gln Pro Thr Gly Cys Phe
 1               5                  10                  15

His Leu Gly Asn Tyr Leu Gly Ala Thr Arg Val Trp Thr Asp Leu Cys
            20                  25                  30

Glu Leu Lys Gln Pro Gly Gln Glu Leu Ile Phe Gly Val Ala
        35                  40                  45

<210> SEQ ID NO 15
<211> LENGTH: 14
<212> TYPE: PRT
<213> ORGANISM: Homo sapien

<400> SEQUENCE: 15

Lys Met Ser Lys Ser Asp Pro Asp Lys Leu Ala Thr Val Cys

<210> SEQ ID NO 16
<211> LENGTH: 16
<212> TYPE: PRT
<213> ORGANISM: Homo sapien

<400> SEQUENCE: 16

Cys Ile Leu Thr Ser Met Lys Lys Val Lys Ser Leu Arg Asp Pro Ser
1               5                   10                  15

<210> SEQ ID NO 17
<211> LENGTH: 20
<212> TYPE: DNA
<213> ORGANISM: Homo sapien

<400> SEQUENCE: 17
ttagtgacgc gcatgaatgg                                         20

<210> SEQ ID NO 18
<211> LENGTH: 23
<212> TYPE: DNA
<213> ORGANISM: Homo sapien

<400> SEQUENCE: 18
tgtggtttcg ctggatagta ggt                                     23

<210> SEQ ID NO 19
<211> LENGTH: 22
<212> TYPE: DNA
<213> ORGANISM: Homo sapien

<400> SEQUENCE: 19
agctcaactg cccagcgtga cc                                      22

<210> SEQ ID NO 20
<211> LENGTH: 22
<212> TYPE: DNA
<213> ORGANISM: Homo sapien

<400> SEQUENCE: 20
cagtcagcct tgaatcctcc cc                                      22

<210> SEQ ID NO 21
<211> LENGTH: 21
<212> TYPE: DNA
<213> ORGANISM: Homo sapien

<400> SEQUENCE: 21
cttcttgcct gtggcataaa c                                       21

<210> SEQ ID NO 22
<211> LENGTH: 22
<212> TYPE: DNA
<213> ORGANISM: Homo sapien

<400> SEQUENCE: 22
cttccactga tgtaaatgtt gt                                      22

<210> SEQ ID NO 23
<211> LENGTH: 20
<212> TYPE: DNA
<213> ORGANISM: Homo sapien

<400> SEQUENCE: 23
agctactgcc atccaatcgc                                                20

<210> SEQ ID NO 24
<211> LENGTH: 21
<212> TYPE: DNA
<213> ORGANISM: Homo sapien

<400> SEQUENCE: 24
gggcgaatcc aattccaaga g                                              21

<210> SEQ ID NO 25
<211> LENGTH: 47
<212> TYPE: DNA
<213> ORGANISM: Artificial Sequence
<220> FEATURE:
<223> OTHER INFORMATION: Artificial Forward Primer

<400> SEQUENCE: 25
gggaattcgc cgccgcgatc gccaaaggat gaaattgatt ctgcagt                  47

<210> SEQ ID NO 26
<211> LENGTH: 56
<212> TYPE: DNA
<213> ORGANISM: Artificial Sequence
<220> FEATURE:
<223> OTHER INFORMATION: Artificial Reverse Primer

<400> SEQUENCE: 26
gctctagatt acttatcgtc gtcatccttg taatcctgaa agtcgaagga cagctt        56

<210> SEQ ID NO 27
<211> LENGTH: 21
<212> TYPE: DNA
<213> ORGANISM: Artificial Sequence
<220> FEATURE:
<223> OTHER INFORMATION: Artificial Forward Primer

<400> SEQUENCE: 27
gggaattcgt cgactggatc c                                              21

<210> SEQ ID NO 28
<211> LENGTH: 29
<212> TYPE: DNA
<213> ORGANISM: Artificial Sequence
<220> FEATURE:
<223> OTHER INFORMATION: Artificial Reverse Primer

<400> SEQUENCE: 28
gctcagagcc ggccgtttaa accttatcg                                      29

<210> SEQ ID NO 29
<211> LENGTH: 21
<212> TYPE: DNA
<213> ORGANISM: Artificial Sequence
<220> FEATURE:
<223> OTHER INFORMATION: Artificial Forward Primer

<400> SEQUENCE: 29
gggaattcgt cgactggatc c                                              21

<210> SEQ ID NO 30
<211> LENGTH: 30
<212> TYPE: DNA
<213> ORGANISM: Artificial Sequence

```
<220> FEATURE:
<223> OTHER INFORMATION: Artificial Reverse Primer

<400> SEQUENCE: 30
gctctagagc cggccgttta aactctttct                                      30

<210> SEQ ID NO 31
<211> LENGTH: 20
<212> TYPE: DNA
<213> ORGANISM: Artificial Sequence
<220> FEATURE:
<223> OTHER INFORMATION: Artificial Forward Primer

<400> SEQUENCE: 31
gccaccgtcc gaataacaga                                                 20

<210> SEQ ID NO 32
<211> LENGTH: 20
<212> TYPE: DNA
<213> ORGANISM: Artificial Sequence
<220> FEATURE:
<223> OTHER INFORMATION: Artificial Reverse Primer

<400> SEQUENCE: 32
catgcaccgc cactatgttg                                                 20

<210> SEQ ID NO 33
<211> LENGTH: 20
<212> TYPE: DNA
<213> ORGANISM: Artificial Sequence
<220> FEATURE:
<223> OTHER INFORMATION: Artificial Forward Primer

<400> SEQUENCE: 33
ggagtcaacg gatttggtcg                                                 20

<210> SEQ ID NO 34
<211> LENGTH: 20
<212> TYPE: DNA
<213> ORGANISM: Artificial Sequence
<220> FEATURE:
<223> OTHER INFORMATION: Artificial Reverse Primer

<400> SEQUENCE: 34
atcgccccac ttgattttgg                                                 20

<210> SEQ ID NO 35
<211> LENGTH: 19
<212> TYPE: DNA
<213> ORGANISM: Homo sapien

<400> SEQUENCE: 35
gcattcaacc tacaggaat                                                  19

<210> SEQ ID NO 36
<211> LENGTH: 19
<212> TYPE: DNA
<213> ORGANISM: Homo sapien

<400> SEQUENCE: 36
ccgacattct gttgtacaa                                                  19

<210> SEQ ID NO 37
<211> LENGTH: 19
<212> TYPE: DNA
```

```
<213> ORGANISM: Homo sapien

<400> SEQUENCE: 37
gctggacaag gaccattta                                                    19

<210> SEQ ID NO 38
<211> LENGTH: 51
<212> TYPE: DNA
<213> ORGANISM: Homo sapien
<220> FEATURE:
<221> NAME/KEY: misc_feature
<222> LOCATION: 26
<223> OTHER INFORMATION: n = C or G

<400> SEQUENCE: 38
ttcatattct gtcgagacac ccatcnccct gtgtttcact tgtctgatta c                51

<210> SEQ ID NO 39
<211> LENGTH: 35
<212> TYPE: DNA
<213> ORGANISM: Rattus

<400> SEQUENCE: 39
acccacagct actgcggctc cccaggtaac ccgag                                  35

<210> SEQ ID NO 40
<211> LENGTH: 20
<212> TYPE: DNA
<213> ORGANISM: Artificial Sequence
<220> FEATURE:
<223> OTHER INFORMATION: Artificial Primer

<400> SEQUENCE: 40
gtgagtgctg gcgcttcatc                                                   20

<210> SEQ ID NO 41
<211> LENGTH: 20
<212> TYPE: DNA
<213> ORGANISM: Artificial Sequence
<220> FEATURE:
<223> OTHER INFORMATION: Artificial Primer

<400> SEQUENCE: 41
ggcctaaagc agaaggtcgg                                                   20

<210> SEQ ID NO 42
<211> LENGTH: 21
<212> TYPE: DNA
<213> ORGANISM: Artificial Sequence
<220> FEATURE:
<223> OTHER INFORMATION: Artificial Forward Primer

<400> SEQUENCE: 42
tttccagcag tctcaggtgt c                                                 21

<210> SEQ ID NO 43
<211> LENGTH: 20
<212> TYPE: DNA
<213> ORGANISM: Artificial Sequence
<220> FEATURE:
<223> OTHER INFORMATION: Artificial Reverse Primer

<400> SEQUENCE: 43
tacagggtat gtgagcaggc                                                   20
```

-continued

```
<210> SEQ ID NO 44
<211> LENGTH: 20
<212> TYPE: DNA
<213> ORGANISM: Artificial Sequence
<220> FEATURE:
<223> OTHER INFORMATION: Artificial Forward Primer

<400> SEQUENCE: 44
aaagggtcat catctccgcc                                              20

<210> SEQ ID NO 45
<211> LENGTH: 20
<212> TYPE: DNA
<213> ORGANISM: Artificial Sequence
<220> FEATURE:
<223> OTHER INFORMATION: Artificial Reverse Primer

<400> SEQUENCE: 45
ccttccacga tgccaaagtt                                              20

<210> SEQ ID NO 46
<211> LENGTH: 19
<212> TYPE: RNA
<213> ORGANISM: Artificial Sequence
<220> FEATURE:
<223> OTHER INFORMATION: siRNA Sense Strand

<400> SEQUENCE: 46
ugguuuacau gucgacuuu                                               19

<210> SEQ ID NO 47
<211> LENGTH: 19
<212> TYPE: RNA
<213> ORGANISM: Artificial Sequence
<220> FEATURE:
<223> OTHER INFORMATION: siRNA Antisense Strand

<400> SEQUENCE: 47
agucgacaug uaaaccauu                                               19

<210> SEQ ID NO 48
<211> LENGTH: 19
<212> TYPE: RNA
<213> ORGANISM: Artificial Sequence
<220> FEATURE:
<223> OTHER INFORMATION: siRNA Sense Strand

<400> SEQUENCE: 48
gcuccaauca gaagugauu                                               19

<210> SEQ ID NO 49
<211> LENGTH: 19
<212> TYPE: RNA
<213> ORGANISM: Artificial Sequence
<220> FEATURE:
<223> OTHER INFORMATION: siRNA Antisense Strand

<400> SEQUENCE: 49
ucacuucuga uuggagcuu                                               19

<210> SEQ ID NO 50
<211> LENGTH: 19
<212> TYPE: RNA
<213> ORGANISM: Artificial Sequence
<220> FEATURE:
<223> OTHER INFORMATION: siRNA Sense Strand
```

```
<400> SEQUENCE: 50
gcauucaacc uacaggaau                                                    19

<210> SEQ ID NO 51
<211> LENGTH: 19
<212> TYPE: RNA
<213> ORGANISM: Artificial Sequence
<220> FEATURE:
<223> OTHER INFORMATION: siRNA Antisense Strand

<400> SEQUENCE: 51
auuccuguag guugaaugc                                                    19

<210> SEQ ID NO 52
<211> LENGTH: 19
<212> TYPE: RNA
<213> ORGANISM: Artificial Sequence
<220> FEATURE:
<223> OTHER INFORMATION: siRNA Sense Strand

<400> SEQUENCE: 52
ccgacauucu guuguacaa                                                    19

<210> SEQ ID NO 53
<211> LENGTH: 19
<212> TYPE: RNA
<213> ORGANISM: Artificial Sequence
<220> FEATURE:
<223> OTHER INFORMATION: siRNA Antisense Strand

<400> SEQUENCE: 53
uuguacaaca gaaugucgg                                                    19

<210> SEQ ID NO 54
<211> LENGTH: 19
<212> TYPE: RNA
<213> ORGANISM: Artificial Sequence
<220> FEATURE:
<223> OTHER INFORMATION: siRNA Sense Strand

<400> SEQUENCE: 54
gcuggacaag gaccauuua                                                    19

<210> SEQ ID NO 55
<211> LENGTH: 19
<212> TYPE: RNA
<213> ORGANISM: Artificial Sequence
<220> FEATURE:
<223> OTHER INFORMATION: siRNA Antisense Strand

<400> SEQUENCE: 55
uaaauggucc uuguccagc                                                    19
```